12) United States Patent
Casemiro et al.

(10) Patent No.: US 12,281,151 B2
(45) Date of Patent: Apr. 22, 2025

(54) CD6 TARGETED CHIMERIC ANTIGEN RECEPTORS FOR TREATMENT OF CERTAIN AUTOIMMUNE DISORDERS

(71) Applicant: City of Hope, Duarte, CA (US)

(72) Inventors: Jose Enrique Montero Casemiro, Duarte, CA (US); Bart Otto Roep, Duarte, CA (US); Christine E. Brown, Duarte, CA (US)

(73) Assignee: City of Hope, Duarte, CA (US)

(*) Notice: Subject to any disclaimer, the term of this patent is extended or adjusted under 35 U.S.C. 154(b) by 844 days.

(21) Appl. No.: 17/256,788

(22) PCT Filed: Jul. 1, 2019

(86) PCT No.: PCT/US2019/040185
§ 371 (c)(1),
(2) Date: Dec. 29, 2020

(87) PCT Pub. No.: WO2020/006568
PCT Pub. Date: Jan. 2, 2020

(65) Prior Publication Data
US 2021/0395329 A1 Dec. 23, 2021

Related U.S. Application Data

(60) Provisional application No. 62/692,609, filed on Jun. 29, 2018.

(51) Int. Cl.
C07K 14/725 (2006.01)
A61K 35/17 (2015.01)
A61K 39/00 (2006.01)
C07K 14/705 (2006.01)
C07K 14/73 (2006.01)
C07K 16/28 (2006.01)
C07K 16/46 (2006.01)
A61K 38/00 (2006.01)

(52) U.S. Cl.
CPC ...... C07K 14/7051 (2013.01); A61K 39/4611 (2023.05); A61K 39/4621 (2023.05); A61K 39/4631 (2023.05); A61K 39/46433 (2023.05); C07K 14/70514 (2013.01); C07K 14/70517 (2013.01); C07K 14/70521 (2013.01); C07K 16/2896 (2013.01); A61K 38/00 (2013.01); C07K 2317/53 (2013.01); C07K 2317/56 (2013.01); C07K 2317/565 (2013.01); C07K 2317/622 (2013.01); C07K 2319/02 (2013.01); C07K 2319/03 (2013.01); C07K 2319/30 (2013.01); C07K 2319/33 (2013.01)

(58) Field of Classification Search
CPC ............ C07K 16/2896; C07K 2317/56; C07K 2317/565; C07K 2317/622; C07K 14/70517; C07K 14/70521; C07K 2317/53; C07K 2319/03; C07K 2319/33; A61K 39/46433; A61K 35/17; A61K 2039/5156; A61K 2039/5158; A61K 39/4611; A61K 39/4631

See application file for complete search history.

(56) References Cited

U.S. PATENT DOCUMENTS

| | | |
|---|---|---|
| 4,676,980 A | 6/1987 | Segal et al. |
| 4,816,567 A | 3/1989 | Cabilly et al. |
| 4,946,778 A | 8/1990 | Ladner et al. |
| 5,530,101 A | 6/1996 | Queen et al. |
| 5,545,806 A | 8/1996 | Lonberg et al. |
| 5,545,807 A | 8/1996 | Surani et al. |
| 5,569,825 A | 10/1996 | Lonberg et al. |
| 5,585,089 A | 12/1996 | Queen et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,693,761 A | 12/1997 | Queen et al. |
| 5,693,762 A | 12/1997 | Queen et al. |
| 5,777,085 A | 7/1998 | Co et al. |
| 5,859,205 A | 1/1999 | Adair et al. |
| 6,180,370 B1 | 1/2001 | Queen et al. |
| 6,210,671 B1 | 4/2001 | Co et al. |
| 6,329,511 B1 | 12/2001 | Vasquez et al. |
| 6,572,857 B1 | 6/2003 | Casimiro et al. |
| 9,574,014 B2 | 2/2017 | Williams et al. |
| 2015/0307623 A1 | 10/2015 | Abbot et al. |
| 2017/0362331 A1* | 12/2017 | Lin ........................ A61P 37/06 |
| 2021/0395329 A1 | 12/2021 | Casimiro et al. |
| 2023/0076643 A1 | 3/2023 | Casimiro et al. |

FOREIGN PATENT DOCUMENTS

| | | |
|---|---|---|
| EP | 0173494 | 3/1986 |
| EP | 2993186 | 3/2016 |
| JP | 2011-513479 | 4/2011 |
| JP | 2016-507499 | 3/2016 |
| JP | 2016-525538 | 8/2016 |

(Continued)

OTHER PUBLICATIONS

Butler et al., Frontiers in Bioengineering and Biotechnology, 2023, 11:1101122, pp. 1-9.*
Schett et al., Lancet, 2023, 402:2034-44.*
Garner et al., Immunology, 2018, 155:273-282.*
Altschul et al., "Basic local alignment search tool," J Mal. Biol., 1990, 215:403-410.
Altschul et al., "Gapped BLAST and PSI-BLAST: a new generation of protein database search programs," Nuc. Acids Res., 1977, 25:3389-3402.
Bluestone et al., "Type 1 diabetes immunotherapy using polyclonal regulatory T cells," Sci Transl Med., Nov. 25, 2015, 7(315):315ral89.
Choi et al., "Human regulatory T cells kill tumor cells through granzyme-dependent cytotoxicity upon retargeting with a bispecific antibody," Cancer Immunol Res., 2013 1(3):163.

(Continued)

Primary Examiner — Hong Sang
(74) Attorney, Agent, or Firm — Fish & Richardson P.C.

(57) ABSTRACT

Provided herein are, inter alia, CD6 targeting CAR-T cell compositions and methods useful for treating autoimmune diseases (e.g., Type I diabetes).

35 Claims, 10 Drawing Sheets
Specification includes a Sequence Listing.

(56) References Cited

FOREIGN PATENT DOCUMENTS

| WO | WO 86/02364 | 4/1986 |
| --- | --- | --- |
| WO | WO 87/02671 | 5/1987 |
| WO | WO 91/00360 | 1/1991 |
| WO | WO 92/20373 | 11/1992 |
| WO | WO 93/08829 | 5/1993 |
| WO | WO 2016/044811 | 3/2016 |
| WO | WO 2016/179319 | 11/2016 |
| WO | WO 2018/083071 | 5/2018 |

OTHER PUBLICATIONS

Duggleby et al., "Clinical Grade Regulatory CD4(+) T Cells (Tregs): Moving Toward Cellular-Based Immunomodulatory Therapies," Front Immunol., 2018, 9:252.
Feldhaus et al., "Flow-cytometric isolation of human antibodies from a nonimmune *Saccharomyces cerevisiae* surface display library," Nature Biotechnology, 2003, 21:163-170.
Fishwild et al., "High-avidity human IgG kappa monoclonal antibodies from a novel strain of minilocus transgenic mice," Nature Biotechnology, 1996, 14:845-851.
Ford et al., "Protein transduction: an alternative to genetic intervention?," Gene Therapy, 2001, 8:1-4.
Fuchs et al. "Minimum Information about T Regulatory Cells: A Step toward Reproducibility and Standardization," Front Immunol., Jan. 15, 2017, 8:1844.
Gangemi et al., "Anti-T12, an anti-CD6 monoclonal antibody, can activate human T lymphocytes," J Immunol., 1989, 143(8):2439-2447 (Abstract Only).
Garcia et al., "Human Treg cells are characterized by low/negative CD6 expression," Cytometry, 2014, 85(10):901-908.
Garner et al., "CD6 monoclonal antibodies differ in epitope, kinetics and mechanism of action," Immunology, 2018, 155:273-282.
Henikoff & Henikoff, "Amino acid substitution matrices from protein blocks," Proc Natl Acad Sci USA., 1992, 89:10915-10919.
International Search Report and Written Opinion in International Application No. PCT/US2019/040185, dated Nov. 14, 2019, 14 pages.
International Preliminary Report on Patentability in International Application No. PCT/US2019/040185, dated Jan. 7, 2021, 8 pages.
Jones et al., "Replacing the complementarity-determining regions in a human antibody with those from a mouse," Nature, 1986, 321:522-525.
Junghans et al., "Anti-Tac-H, a humanized antibody to the interleukin 2 receptor with new features for immunotherapy in malignant and immune disorders," Cancer Res., 1990, 50:1495-1502.
Karlin and Altschul, "Applications and statistics for multiple high-scoring segments in molecular sequences," Proc Natl Acad Sci., 1993, 90(12):5873-5877.
Kohler & Milstein, "Continuous cultures of fused cells secreting antibody of predefined specificity," Nature, 1975, 256:495-497.
Kozbor et al., "The production of monoclonal antibodies from human lymphocytes," Immunology Today., 1983, 4:72-79.
Lonberg & Huszar, "Human antibodies from transgenic mice," Intern Rev Immunol., 1995, 13:65-93.
Lonberg et al., "Antigen-specific human antibodies from mice comprising four distinct genetic modifications," Nature, 1994, 368:856-859.
Marks et al., "By-Passing Immunization: Building High Affinity Human Antibodies by Chain Shuffling," Bio/Technology, 1992, 10:779-783.
McCafferty et al., "Phage antibodies: filamentous phage displaying antibody variable domains," Nature, 1990, 348:552-554.
Milone et al., "Chimeric receptors containing CD137 signal transduction domains mediate enhanced survival of T cells and increased antileukemic efficacy in vivo," Mol Ther., Aug. 2009, 17(8):1453-1464.
Morrison and Oi, "Genetically engineered antibody molecules," Adv Immunol., 1988, 44:65-92.
Morrison et al., "Chimeric human antibody molecules: mouse antigen-binding domains with human constant region domains," PNAS USA., 1984, 81:6851-6855.
Morrison, "Success in specification," Nature, 1994, 368:812-813.
Needleman et al., "A general method applicable to the search for similarities in the amino acid sequence of two proteins," J Mol Biol., Mar. 1970, 48(3):443-453.
Neuberger, "Generating high-avidity human Mabs in mice," Nature Biotechnology, 1996, 14:826.
Padlan, "Anatomy of the antibody molecule," Molec Immun., 1994, 31(3):169-217.
Padlan, "A possible procedure for reducing the immunogenicity of antibody variable domains while preserving their ligand-binding properties," Molec Immun., 1991, 28:489-498.
Pearson and Lipman, "Improved tools for biological sequence comparison," Proc. Nat'l. Acad. Sci. USA., 1988, 85:2444-2448.
Presta, "Antibody engineering," Curr Op Struct Biol., 1992, 2:593-596.
Prochiantz, "For protein transduction, chemistry can win over biology," Nat Methods., 2007, 4:119-120.
Putnam et al., "Expansion of human regulatory T-cells from patients with type 1 diabetes," Diabetes, 2009, 58(3):652-662.
Riechmann et al., "Reshaping human antibodies for therapy," Nature, 1988, 332:323-327.
Smith and Waterman, "Comparison of Biosequences," Adv Appl Math., 1970 2:482-489.
Suresh et al., "Bispecific monoclonal antibodies from hybrid hybridomas," Methods in Enzymology, 1986, 121:210-228.
Thorpe et al., "The Preparation and Cytotoxic Properties of Antibody-Toxin Conjugates," Immunol Rev., 1982, 62:119-158.
Traunecker et al., "Bispecific single chain molecules (Janusins) target cytotoxic lymphocytes on HIV infected cells," EMBO J., 1991, 10:3655-3659.
Verhoeyen et al., "Reshaping human antibodies: grafting an antilysozyme activity," Science, 1988, 239:1534-1536.
Winter and Milstein, "Man-made antibodies," Nature, 1991, 349:293-299.
Zomiak et al., "Yeast display biopanning identifies human antibodies targeting glioblastoma stem-like cells," Scientific Reports, 2017, 7:15840.
NCBI sequence reference NM_000734.3, "*Homo sapiens* CD247 molecule (CD247), transcript variant 2, mRNA," dated Apr. 16, 2019, 4 pages.
NCBI sequence reference NM_001145873.1, "*Homo sapiens* CD8a molecule (CD8A), transcript variant 3, mRNA," dated Jun. 12, 2022, 4 pages.
NCBI sequence reference NM_001178100.1, "*Homo sapiens* CD8b molecule (CD8B), transcript variant 6, mRNA," dated Feb. 23, 2019, 3 pages.
NCBI sequence reference NM_001195017.2, "*Homo sapiens* CD4 molecule (CD4), transcript variant 5, mRNA," dated Mar. 25, 2019, 4 pages.
NCBI sequence reference NM_001243077.1, "*Homo sapiens* CD28 molecule (CD28), transcript variant 2, mRNA," dated May 2, 2019, 4 pages.
NCBI sequence reference NM_001243078.1, "*Homo sapiens* CD28 molecule (CD28), transcript variant 3, mRNA," dated Jun. 7, 2020, 4 pages.
NCBI sequence reference NM_001768.6, "*Homo sapiens* CD8a molecule (CD8A), transcript variant 1, mRNA," dated Feb. 26, 2020, 4 pages.
NCBI sequence reference NM_004195.2, "*Homo sapiens* TNF receptor superfamily member 18 (TNFRSF18), transcript variant 1, mRNA," dated Sep. 15, 2018, 4 pages.
NCBI sequence reference NM_004931.4, "*Homo sapiens* CD8b molecule (CD8B), transcript variant 5, mRNA," dated May 4, 2019, 3 pages.
NCBI sequence reference NM_006139.3, "*Homo sapiens* CD28 molecule (CD28), transcript variant 1, mRNA," dated Nov. 18, 2018, 4 pages.
NCBI sequence reference NM_148901.1, "*Homo sapiens* TNF receptor superfamily member 18 (TNFRSF18), transcript variant 2, mRNA," dated Apr. 16, 2019, 3 pages.

(56) References Cited

OTHER PUBLICATIONS

NCBI sequence reference NM_148902.1, "*Homo sapiens* TNF receptor superfamily member 18 (TNFRSF18), transcript variant 3, mRNA," dated Apr. 15, 2019, 3 pages.
NCBI sequence reference NM_172101.3, "*Homo sapiens* CD8b molecule (CD8B), transcript variant 3, mRNA," dated Feb. 23, 2019, 3 pages.
NCBI sequence reference NM_172102.3, "*Homo sapiens* CD8b molecule (CD8B), transcript variant 4, mRNA," dated Feb. 23, 2019, 3 pages.
NCBI sequence reference NM_172213.3, "*Homo sapiens* CD8b molecule (CD8B), transcript variant 2, mRNA," dated Feb. 22, 2019, 3 pages.
NCBI sequence reference NM_198053.2, "*Homo sapiens* CD247 molecule (CD247), transcript variant 1, mRNA," dated Jan. 13, 2020, 4 pages.
NCBI sequence reference NM_000616.4, "*Homo sapiens* CD4 molecule (CD4), transcript variant 1, mRNA," dated Nov. 4, 2018, 4 pages.
NCBI sequence reference NM_001037631.3, "*Homo sapiens* cytotoxic T-lymphocyte associated protein 4 (CTLA4), transcript variant 2, mRNA," dated May 22, 2022, 3 pages.
NCBI sequence reference NM_001561.5, "*Homo sapiens* TNF receptor superfamily member 9 (TNFRSF9), mRNA," dated Jul. 23, 2019, 5 pages.
NCBI sequence reference NM_003327.3, "*Homo sapiens* TNF receptor superfamily member 4 (TNFRSF4), mRNA," dated Oct. 21, 2018, 4 pages.
NCBI sequence reference NM_005018.2, "*Homo sapiens* programmed cell death 1 (PDCD1), mRNA," dated Nov. 4, 2018, 3 pages.
NCBI sequence reference NM_005214.5, "*Homo sapiens* cytotoxic T-lymphocyte associated protein 4 (CTLA4), transcript variant 1, mRNA," dated May 22, 2022, 4 pages.
NCBI sequence reference NM_001195014.2, "*Homo sapiens* CD4 molecule (CD4), transcript variant 2, mRNA," dated Mar. 25, 2019, 4 pages.
NCBI sequence reference NM_001195015.2, "*Homo sapiens* CD4 molecule (CD4), transcript variant 3, mRNA," dated Mar. 25, 2019, 4 pages.
NCBI sequence reference NM_001195016.2, "*Homo sapiens* CD4 molecule (CD4), transcript variant 4, mRNA," dated Mar. 25, 2019, 4 pages.
NCBI sequence reference NM_012092.3, "*Homo sapiens* inducible T cell costimulator (ICOS), mRNA," dated Jun. 7, 2019, 4 pages.
NCBI sequence reference NM_171827.3, "*Homo sapiens* CD8a molecule (CD8A), transcript variant 2, mRNA," dated Apr. 26, 2020, 4 pages.
NCBI sequence reference NP_001139345.1, "T-cell surface glycoprotein CD8 alpha chain isoform 1 precursor [*Homo sapiens*]," dated Jun. 12, 2022, 3 pages.
NCBI sequence reference NP_001171571.1, "T-cell surface glycoprotein CD8 beta chain isoform 6 precursor [*Homo sapien*]," dated Jan. 30, 2022, 2 pages.
NCBI sequence reference NP_001181944.1, "T-cell surface glycoprotein CD4 isoform 3 [*Homo sapiens*]," dated Jun. 12, 2022, 3 pages.
NCBI sequence reference NP_001552.2, "tumor necrosis factor receptor superfamily member 9 precursor [*Homo sapiens*]," dated Jul. 24, 2022, 3 pages.
NCBI sequence reference NP_001759.3, "T-cell surface glycoprotein CD8 alpha chain isoform 1 precursor [*Homo sapiens*]," dated Jun. 12, 2022, 3 pages.
NCBI sequence reference NP_003318.1, "tumor necrosis factor receptor superfamily member 4 precursor [*Homo sapiens*]," dated Jul. 18, 2022, 3 pages.
NCBI sequence reference NP_006716.3, "T-cell differentiation antigen CD6 isoform 1 precursor [*Homo sapiens*]," dated Jun. 12, 2022, 3 pages.
NCBI sequence reference NP_742100.1, "T-cell surface glycoprotein CD8 beta chain isoform 4 precursor [*Homo sapiens*]," dated Apr. 17, 2022, 3 pages.
NCBI sequence reference NP_757362.1, "T-cell surface glycoprotein CD8 beta chain isoform 2 precursor [*Homo sapiens*]," dated Apr. 17, 2022, 2 pages.
NCBI sequence reference NP_932170.1, "T-cell surface glycoprotein CD3 zeta chain isoform 1 precursor [*Homo sapiens*]," dated Jul. 5, 2022, 3 pages.
NCBI sequence reference NP_000607.1, "T-cell surface glycoprotein CD4 isoform 1 precursor [*Homo sapiens*]," dated Jun. 12, 2022, 4 pages.
NCBI sequence reference NP_000725.1, "T-cell surface glycoprotein CD3 zeta chain isoform 2 precursor [*Homo sapiens*]," dated Jul. 5, 2022, 3 pages.
NCBI sequence reference NP_001032720.1, "cytotoxic T-lymphocyte protein 4 isoform CTLA-4del™[*Homo sapiens*]," dated May 22, 2022, 2 pages.
NCBI sequence reference NP_001181943.1, "T-cell surface glycoprotein CD4 isoform 2 [*Homo sapiens*]," dated Jun. 12, 2022, 2 pages.
NCBI sequence reference NP_001181945.1, "T-cell surface glycoprotein CD4 isoform 3 [*Homo sapiens*]," dated Jun. 12, 2022, 2 pages.
NCBI sequence reference NP_001181946.1, "T-cell surface glycoprotein CD4 isoform 3 [*Homo sapiens*]," dated Jun. 12, 2022, 3 pages.
NCBI sequence reference NP_001230006.1, "T-cell-specific surface glycoprotein CD28 isoform 2 precursor [*Homo sapiens*]," dated May 22, 2022, 2 pages.
NCBI sequence reference NP_001230007.1, "T-cell-specific surface glycoprotein CD28 isoform 3 precursor [*Homo sapiens*]," dated May 23, 2022, 2 pages.
NCBI sequence reference NP_001241679.1, "T-cell differentiation antigen CD6 isoform 2 precursor [*Homo sapiens*]," dated Jun. 12, 2022, 2 pages.
NCBI sequence reference NP_001241680.1, "T-cell differentiation antigen CD6 isoform 3 precursor [*Homo sapiens*]," dated Jun. 12, 2022, 2 pages.
NCBI sequence reference NP_004186.1, "tumor necrosis factor receptor superfamily member 18 isoform 1 precursor [*Homo sapiens*]," dated Apr. 17, 2022, 3 pages.
NCBI sequence reference NP_004922.1, "T-cell surface glycoprotein CD8 beta chain isoform 5 precursor [*Homo sapiens*]," dated Jan. 30, 2022, 3 pages.
NCBI sequence reference NP_005009.2, "programmed cell death protein 1 precursor [*Homo sapiens*]," dated Jul. 24, 2022, 3 pages.
NCBI sequence reference NP_005205.2, "cytotoxic T-lymphocyte protein 4 isoform CTLA4-™ precursor [*Homo sapiens*]," dated May 22, 2022, 3 pages.
NCBI sequence reference NP_006130.1, "T-cell-specific surface glycoprotein CD28 isoform 1 precursor [*Homo sapiens*]," dated May 22, 2022, 3 pages.
NCBI sequence reference NP_036224.1, "inducible T-cell costimulator precursor [*Homo sapiens*]," dated Apr. 17, 2022, 3 pages.
NCBI sequence reference NP_683699.1, "tumor necrosis factor receptor superfamily member 18 isoform 2 precursor [*Homo sapiens*]," dated Apr. 17, 2022, 3 pages.
NCBI sequence reference NP_683700.1, "tumor necrosis factor receptor superfamily member 18 isoform 3 precursor [*Homo sapiens*]," dated Apr. 18, 2022, 3 pages.
NCBI sequence reference NP_741969.1, "T-cell surface glycoprotein CD8 alpha chain isoform 2 precursor [*Homo sapiens*]," dated Jun. 12, 2022, 2 pages.
NCBI sequence reference NP_742099.1, "T-cell surface glycoprotein CD8 beta chain isoform 3 precursor [*Homo sapiens*]," dated Apr. 17, 2022, 2 pages.
NCBI sequence reference NR_027353.1, "*Homo sapiens* CD8a molecule (CD8A), transcript variant 4, non-coding RNA," dated Jun. 7, 2020, 3 pages.
NCBI sequence reference XM_011533164.2, "Predicted: *Homo sapiens* CD8b molecule (CD8B), transcript variant X1, mRNA," dated Nov. 22, 2021, 2 pages.
NCBI sequence reference XP_011531466.1, "T-cell surface glycoprotein CD8 beta chain isoform X1 [*Homo sapiens*]," dated Apr. 5, 2022, 2 pages.

(56) References Cited

OTHER PUBLICATIONS

JP Office Action in Japanese Appln. No. 2021-500042, mailed on Jun. 13, 2023, 7 pages (with English translation).

* cited by examiner pF03496 - CD6scFvop(VH_VL)-IgG4(L235E,N297Q)op-CTLA4-Zetaop

<u>MLLLVTSLLLCELPHPAFLLI</u><u>PEVQLVESGGGLVKPGGSLKLSCAASGFKFSRYAMSWVRQAPGKRLEWVATISSGGSYIY</u>
<u>Signal Sequence</u>            CD6scFv(Vh-Vl)

<u>YPDSVKGRFTISRDNVKNTLYLQMSSLRSEDTAMYYCARRDYDLDYFDSWGQGTLVTVSSGSTSGGGSGGGSGGGS</u>

<u>SDIQMTQSPSSLSASVGDRVTITCKASRDIRSYLTWYQQKPGKAPKTLIYYATSLADGVPSRFSGSGSGQDYSLTISSLESD</u>

<u>DTATYYCLQHGESPFTFGSGTKLEIKRA</u><u>ESKYGPPCPPCPAPEFEGGPSVFLFPPKPKDTLMISRTPEVTCVVVDVSQEDP</u>
                            IgG4op(L235E,N297Q)

<u>EVQFNWYVDGVEVHNAKTKPREEQFQSTYRVVSVLTVLHQDWLNGKEYKCKVSNKGLPSSIEKTISKAKGQPREPQVY</u>

<u>TLPPSQEEMTKNQVSLTCLVKGFYPSDIAVEWESNGQPENNYKTTPPVLDSDGSFFLYSRLTVDKSRWQEGNVFSCSV</u>

<u>MHEALHNHYTQKSLSLSLGKMALIVLGGVAGLLLFIGLGIFF</u><u>AVSLSKMLKKRSPLTTGVYVKMPPTEPECEKQFQPYFIPI</u>
                CD4 TM                          CTLA-4

<u>NGGGRVKFSRSADAPAYQQGQNQLYNELNLGRREEYDVLDKRRGRDPEMGGKPRRKNPQEGLYNELQKDKMAEAY</u>
  Link <u>CD3ζ</u>

<u>SEIGMKGERRRGKGHDGLYQGLSTATKDTYDALHMQALPPR</u>

FIG. 1 pF03497 - CD6scFvop(VL_VH)-IgG4(L235E,N297Q)op-CTLA4-Zetaop

<u>MLLLVTSLLLCELPHPAFLLIP</u><u>DIQMTQSPSSLSASVGDRVTITCKASRDIRSYLTWYQQKPGKAPKTLIYYATSLADGVPS</u>

<u>Signal Sequence</u>　　　　　　　CD6scFv(Vl-Vh)

<u>RFSGSGSGQDYSLTISSLESDDTATYYCLQHGESPFTFGSGTKLEIKRAGSTSGGGSGGGSGGGGSSEVQLVESGGGLVK</u>

<u>PGGSLKLSCAASGFKFSRYAMSWVRQAPGKRLEWVATISSGGSYIYYPDSVKGRFTISRDNVKNTLYLQMSSLRSEDTA</u>

<u>MYYCARRDYDLDYFDSWGQGTLVTVSS</u><u>ESKYGPPCPPCPAPEFEGGPSVFLPPKPKDTLMISRTPEVTCVVVDVSQED</u>

IgG4(L235E,N297Q)op

<u>PEVQFNWYVDGVEVHNAKTKPREEQFQSTYRVVSVLTVLHQDWLNGKEYKCKVSNKGLPSSIEKTISKAKGQPREPQV</u>

<u>YTLPPSQEEMTKNQVSLTCLVKGFYPSDIAVEWESNGQPENNYKTTPPVLDSDGSFFLYSRLTVDKSRWQEGNVFSCSV</u>

<u>MHEALHNHYTQKSLSLSLGKMALIVLGGVAGLLLFIGLGIFF</u><u>AVSLSKMLKKRSPLTTGVYVKMPPTEPECEKQFQPYFIPI</u>

CD4 TM　　　　　　　　CTLA-4

<u>NGGGR</u><u>VKFSRSADAPAYQQGQNQLYNELNLGRREEYDVLDKRRGRDPEMGGKPRRKNPQEGLYNELQKDKMAEAY</u>

Link　<u>CD3ζ</u>

<u>SEIGMKGERRRGKGHDGLYQGLSTATKDTYDALHMQALPPR</u>

FIG. 2 pF03488 - CD6scFv(VH-VL)-IgG4op(L235E, N297Q)-41BB-Zetaop

<u>MLLLVTSLLLCELPHPAFLL</u><u>IPEVQLVESGGGLVKPGGSLKLSCAASGFKFSRYAMSWVRQAPGKRLEWVATISSGGSYIY</u>
<u>Signal Sequence</u>     CD6scFv(Vh-Vl)

<u>YPDSVKGRFTISRDNVKNTLYLQMSSLRSEDTAMYYCARRDYDLDYFDSWGQGTLVTVSSGSTSGGGSGGGSGGGGS</u>

<u>SDIQMTQSPSSLSASVGDRVTITCKASRDIRSYLTWYQQKPGKAPKTLIYYATSLADGVPSRFSGSGSGQDYSLTISSLESD</u>

<u>DTATYYCLQHGESPFTFGSGTKLEIKRA</u><u>ESKYGPPCPPCPAPEFEGGPSVFLFPPKPKDTLMISRTPEVTCVVVDVSQEDP</u>
                            IgG4op(L235E, N297Q)

<u>EVQFNWYVDGVEVHNAKTKPREEQFQSTYRVVSVLTVLHQDWLNGKEYKCKVSNKGLPSSIEKTISKAKGQPREPQVY</u>

<u>TLPPSQEEMTKNQVSLTCLVKGFYPSDIAVEWESNGQPENNYKTTPPVLDSDGSFFLYSRLTVDKSRWQEGNVFSCSV</u>

<u>MHEALHNHYTQKSLSLSLGKMALIVLGGVAGLLLFIGLGIFF</u><u>KRGRKKLLYIFKQPFMRPVQTTQEEDGCSCRFPEEEEGG</u>
             CD4 TM                        41BB
<u>CELGGGRVKFSRSADAPAYQQGQNQLYNELNLGRREEYDVLDKRRGRDPEMGGKPRRKNPQEGLYNELQKDKMAEA</u>
  Link  CD3ζ
<u>YSEIGMKGERRRGKGHDGLYQGLSTATKDTYDALHMQALPPR</u>

FIG. 3 pF03491 - CD6scFv(VL-VH)-IgG4op(L235E, N297Q)-41BB-Zetaop

<u>MLLLVTSLLLCELPHPAFLLIP</u><u>DIQMTQSPSSLSASVGDRVTITCKASRDIRSYLTWYQQKPGKAPKTLIYYATSLADGVPS</u>

<u>Signal Sequence</u>        CD6scFv(Vl-Vh)

<u>RFSGSGSGQDYSLTISSLESDDTATYYCLQHGESPFTFGSGTKLEIKRAGSTSGGGSGGGSGGGGSSEVQLVESGGGLVK</u>

<u>PGGSLKLSCAASGFKFSRYAMSWVRQAPGKRLEWVATISSGGSYIYYPDSVKGRFTISRDNVKNTLYLQMSSLRSEDTA</u>

<u>MYYCARRDYDLDYFDSWGQGTLVTVSS</u><u>ESKYGPPCPPCPAPEFEGGPSVFLPPKPKDTLMISRTPEVTCVVVDVSQED</u>

<u>IgG4op(L235E, N297Q)</u>

<u>PEVQFNWYVDGVEVHNAKTKPREEQFQSTYRVVSVLTVLHQDWLNGKEYKCKVSNKGLPSSIEKTISKAKGQPREPQV</u>

<u>YTLPPSQEEMTKNQVSLTCLVKGFYPSDIAVEWESNGQPENNYKTTPPVLDSDGSFFLYSRLTVDKSRWQEGNVFSCSV</u>

<u>MHEALHNHYTQKSLSLSLGKMALIVLGGVAGLLLFIGLGIFF</u><u>KRGRKKLLYIFKQPFMRPVQTTQEEDGCSCRFPEEEEGG</u>

CD4 TM                  41BB

<u>CELGGGRVKFSRSADAPAYQQGQNQLYNELNLGRREEYDVLDKRRGRDPEMGGKPRRKNPQEGLYNELQKDKMAEA</u>

Link    <u>CD3ζ</u>

<u>YSEIGMKGERRRGKGHDGLYQGLSTATKDTYDALHMQALPPR</u>

FIG. 4

EVQLVESGGGLVKPGGSLKLSCAASGFKFSRYAMSWVRQAPGKGLEWVATISSGGSYIYYPDSV
Heavy chain
KGRFTISRDNVKNTLYLQMSSLRSEDTAMYYCARRDYDLDYFDSWGQGTLVTVSSGSTSGGGSG
                                                   Linker
GGSGGGGSGDIQMTQSPSSLSASVGDRVTITCKASRDIRSYLTWYQQKPGKAPKTLIYYATSLA
   Light chain
DGVPSRFSGSGSGQDYSLTISSLESDDTATYYCLQHGESPFTFGSGTKMEIK
(SEQ ID NO:73)

2H2 scFv (CD6 scFv mutant, from pF03496)
Mutations in bold + large font

FIG. 10

SEQUENCE LISTING

<160> NUMBER OF SEQ IDS NOS: 93

<210> SEQ ID NO 1
<211> LENGTH: 668
<212> TYPE: PRT
<213> ORGANISM: Homo sapiens

<400> SEQUENCE: 1

Met Trp Leu Phe Phe Gly Ile Thr Gly Leu Leu Thr Ala Ala Leu Ser
1               5                   10                  15

Gly His Pro Ser Pro Ala Pro Pro Asp Gln Leu Asn Thr Ser Ser Ala
            20                  25                  30

Glu Ser Glu Leu Trp Glu Pro Gly Glu Arg Leu Pro Val Arg Leu Thr
        35                  40                  45

Asn Gly Ser Ser Ser Cys Ser Gly Thr Val Glu Val Arg Leu Glu Ala
    50                  55                  60

```
Ser Trp Glu Pro Ala Cys Gly Ala Leu Trp Asp Ser Arg Ala Ala Glu
 65                  70                  75                  80

Ala Val Cys Arg Ala Leu Gly Cys Gly Gly Ala Glu Ala Ala Ser Gln
                 85                  90                  95

Leu Ala Pro Pro Thr Pro Glu Leu Pro Pro Pro Ala Ala Gly Asn
            100                 105                 110

Thr Ser Val Ala Ala Asn Ala Thr Leu Ala Gly Ala Pro Ala Leu Leu
            115                 120                 125

Cys Ser Gly Ala Glu Trp Arg Leu Cys Glu Val Val Glu His Ala Cys
        130                 135                 140

Arg Ser Asp Gly Arg Arg Ala Arg Val Thr Cys Ala Glu Asn Arg Ala
145                 150                 155                 160

Leu Arg Leu Val Asp Gly Gly Ala Cys Ala Gly Arg Val Glu Met
                165                 170                 175

Leu Glu His Gly Glu Trp Gly Ser Val Cys Asp Asp Thr Trp Asp Leu
            180                 185                 190

Glu Asp Ala His Val Val Cys Arg Gln Leu Gly Cys Gly Trp Ala Val
        195                 200                 205

Gln Ala Leu Pro Gly Leu His Phe Thr Pro Gly Arg Gly Pro Ile His
    210                 215                 220

Arg Asp Gln Val Asn Cys Ser Gly Ala Glu Ala Tyr Leu Trp Asp Cys
225                 230                 235                 240

Pro Gly Leu Pro Gly Gln His Tyr Cys Gly His Lys Glu Asp Ala Gly
                245                 250                 255

Ala Val Cys Ser Glu His Gln Ser Trp Arg Leu Thr Gly Gly Ala Asp
            260                 265                 270

Arg Cys Glu Gly Gln Val Glu Val His Phe Arg Gly Val Trp Asn Thr
        275                 280                 285

Val Cys Asp Ser Glu Trp Tyr Pro Ser Glu Ala Lys Val Leu Cys Gln
    290                 295                 300

Ser Leu Gly Cys Gly Thr Ala Val Glu Arg Pro Lys Gly Leu Pro His
305                 310                 315                 320

Ser Leu Ser Gly Arg Met Tyr Tyr Ser Cys Asn Gly Glu Glu Leu Thr
                325                 330                 335

Leu Ser Asn Cys Ser Trp Arg Phe Asn Asn Ser Asn Leu Cys Ser Gln
            340                 345                 350

Ser Leu Ala Ala Arg Val Leu Cys Ser Ala Ser Arg Ser Leu His Asn
        355                 360                 365

Leu Ser Thr Pro Glu Val Pro Ala Ser Val Gln Thr Val Thr Ile Glu
    370                 375                 380

Ser Ser Val Thr Val Lys Ile Glu Asn Lys Glu Ser Arg Glu Leu Met
385                 390                 395                 400

Leu Leu Ile Pro Ser Ile Val Leu Gly Ile Leu Leu Gly Ser Leu
                405                 410                 415

Ile Phe Ile Ala Phe Ile Leu Leu Arg Ile Lys Gly Lys Tyr Ala Leu
            420                 425                 430

Pro Val Met Val Asn His Gln His Leu Pro Thr Thr Ile Pro Ala Gly
        435                 440                 445

Ser Asn Ser Tyr Gln Pro Pro Ile Thr Ile Pro Lys Glu Val Phe
    450                 455                 460

Met Leu Pro Ile Gln Val Gln Ala Pro Pro Glu Asp Ser Asp Ser
465                 470                 475                 480

Gly Ser Asp Ser Asp Tyr Glu His Tyr Asp Phe Ser Ala Gln Pro Pro
```

```
                485                 490                 495
Val Ala Leu Thr Thr Phe Tyr Asn Ser Gln Arg His Arg Val Thr Asp
            500                 505                 510

Glu Glu Val Gln Gln Ser Arg Phe Gln Met Pro Pro Leu Glu Glu Gly
        515                 520                 525

Leu Glu Glu Leu His Ala Ser His Ile Pro Thr Ala Asn Pro Gly His
    530                 535                 540

Cys Ile Thr Asp Pro Pro Ser Leu Gly Pro Gln Tyr His Pro Arg Ser
545                 550                 555                 560

Asn Ser Glu Ser Ser Thr Ser Ser Gly Glu Asp Tyr Cys Asn Ser Pro
            565                 570                 575

Lys Ser Lys Leu Pro Pro Trp Asn Pro Gln Val Phe Ser Ser Glu Arg
        580                 585                 590

Ser Ser Phe Leu Glu Gln Pro Pro Asn Leu Glu Leu Ala Gly Thr Gln
    595                 600                 605

Pro Ala Phe Ser Ala Gly Pro Pro Ala Asp Asp Ser Ser Ser Thr Ser
            610                 615                 620

Ser Gly Glu Trp Tyr Gln Asn Phe Gln Pro Pro Gln Pro Pro Ser
625                 630                 635                 640

Glu Glu Gln Phe Gly Cys Pro Gly Ser Pro Ser Pro Gln Pro Asp Ser
            645                 650                 655

Thr Asp Asn Asp Asp Tyr Asp Asp Ile Ser Ala Ala
        660                 665

<210> SEQ ID NO 2
<211> LENGTH: 601
<212> TYPE: PRT
<213> ORGANISM: Homo sapiens

<400> SEQUENCE: 2

Met Trp Leu Phe Phe Gly Ile Thr Gly Leu Leu Thr Ala Ala Leu Ser
1               5                   10                  15

Gly His Pro Ser Pro Ala Pro Pro Asp Gln Leu Asn Thr Ser Ser Ala
            20                  25                  30

Glu Ser Glu Leu Trp Glu Pro Gly Glu Arg Leu Pro Val Arg Leu Thr
        35                  40                  45

Asn Gly Ser Ser Ser Cys Ser Gly Thr Val Glu Val Arg Leu Glu Ala
    50                  55                  60

Ser Trp Glu Pro Ala Cys Gly Ala Leu Trp Asp Ser Arg Ala Ala Glu
65                  70                  75                  80

Ala Val Cys Arg Ala Leu Gly Cys Gly Gly Ala Glu Ala Ala Ser Gln
                85                  90                  95

Leu Ala Pro Pro Thr Pro Glu Leu Pro Pro Pro Ala Ala Gly Asn
            100                 105                 110

Thr Ser Val Ala Ala Asn Ala Thr Leu Ala Gly Ala Pro Ala Leu Leu
        115                 120                 125

Cys Ser Gly Ala Glu Trp Arg Leu Cys Glu Val Val Glu His Ala Cys
    130                 135                 140

Arg Ser Asp Gly Arg Arg Ala Arg Val Thr Cys Ala Glu Asn Arg Ala
145                 150                 155                 160

Leu Arg Leu Val Asp Gly Gly Gly Ala Cys Ala Gly Arg Val Glu Met
                165                 170                 175

Leu Glu His Gly Glu Trp Gly Ser Val Cys Asp Asp Thr Trp Asp Leu
            180                 185                 190
```

```
Glu Asp Ala His Val Val Cys Arg Gln Leu Gly Cys Gly Trp Ala Val
            195                 200                 205
Gln Ala Leu Pro Gly Leu His Phe Thr Pro Gly Arg Gly Pro Ile His
    210                 215                 220
Arg Asp Gln Val Asn Cys Ser Gly Ala Glu Ala Tyr Leu Trp Asp Cys
225                 230                 235                 240
Pro Gly Leu Pro Gly Gln His Tyr Cys Gly His Lys Glu Asp Ala Gly
                245                 250                 255
Ala Val Cys Ser Glu His Gln Ser Trp Arg Leu Thr Gly Gly Ala Asp
            260                 265                 270
Arg Cys Glu Gly Gln Val Glu Val His Phe Arg Gly Val Trp Asn Thr
    275                 280                 285
Val Cys Asp Ser Glu Trp Tyr Pro Ser Glu Ala Lys Val Leu Cys Gln
290                 295                 300
Ser Leu Gly Cys Gly Thr Ala Val Glu Arg Pro Lys Gly Leu Pro His
305                 310                 315                 320
Ser Leu Ser Gly Arg Met Tyr Tyr Ser Cys Asn Gly Glu Glu Leu Thr
                325                 330                 335
Leu Ser Asn Cys Ser Trp Arg Phe Asn Asn Ser Asn Leu Cys Ser Gln
            340                 345                 350
Ser Leu Ala Ala Arg Val Leu Cys Ser Ala Ser Arg Ser Leu His Asn
    355                 360                 365
Leu Ser Thr Pro Glu Val Pro Ala Ser Val Gln Thr Val Thr Ile Glu
370                 375                 380
Ser Ser Val Thr Val Lys Ile Glu Asn Lys Glu Ser Arg Glu Leu Met
385                 390                 395                 400
Leu Leu Ile Pro Ser Ile Val Leu Gly Ile Leu Leu Gly Ser Leu
                405                 410                 415
Ile Phe Ile Ala Phe Ile Leu Leu Arg Ile Lys Gly Lys Tyr Val Phe
            420                 425                 430
Met Leu Pro Ile Gln Val Gln Ala Pro Pro Glu Asp Ser Asp Ser
    435                 440                 445
Gly Ser Asp Ser Asp Tyr Glu His Tyr Asp Phe Ser Ala Gln Pro Pro
450                 455                 460
Val Ala Leu Thr Thr Phe Tyr Asn Ser Gln Arg His Arg Val Thr Asp
465                 470                 475                 480
Glu Glu Val Gln Gln Ser Arg Phe Gln Met Pro Pro Leu Glu Glu Gly
                485                 490                 495
Leu Glu Glu Leu His Ala Ser His Ile Pro Thr Ala Asn Pro Gly His
            500                 505                 510
Cys Ile Thr Asp Pro Pro Ser Leu Gly Pro Gln Tyr His Pro Arg Ser
    515                 520                 525
Asn Ser Glu Ser Ser Thr Ser Ser Gly Glu Asp Tyr Cys Asn Ser Pro
530                 535                 540
Lys Ser Lys Leu Pro Pro Trp Asn Pro Gln Val Phe Ser Ser Glu Arg
545                 550                 555                 560
Ser Ser Phe Leu Glu Gln Pro Pro Asn Leu Glu Leu Ala Gly Thr Gln
                565                 570                 575
Pro Ala Phe Ser Gly Ser Pro Ser Pro Gln Pro Asp Ser Thr Asp Asn
            580                 585                 590
Asp Asp Tyr Asp Asp Ile Ser Ala Ala
    595                 600
```

-continued

```
<210> SEQ ID NO 3
<211> LENGTH: 601
<212> TYPE: PRT
<213> ORGANISM: Homo sapiens

<400> SEQUENCE: 3

Met Trp Leu Phe Phe Gly Ile Thr Gly Leu Leu Thr Ala Ala Leu Ser
1               5                   10                  15

Gly His Pro Ser Pro Ala Pro Asp Gln Leu Asn Thr Ser Ser Ala
            20                  25                  30

Glu Ser Glu Leu Trp Glu Pro Gly Glu Arg Leu Pro Val Arg Leu Thr
            35                  40                  45

Asn Gly Ser Ser Ser Cys Ser Gly Thr Val Glu Val Arg Leu Glu Ala
50                  55                  60

Ser Trp Glu Pro Ala Cys Gly Ala Leu Trp Asp Ser Arg Ala Ala Glu
65                  70                  75                  80

Ala Val Cys Arg Ala Leu Gly Cys Gly Gly Ala Glu Ala Ala Ser Gln
                85                  90                  95

Leu Ala Pro Pro Thr Pro Glu Leu Pro Pro Pro Ala Ala Gly Asn
            100                 105                 110

Thr Ser Val Ala Ala Asn Ala Thr Leu Ala Gly Ala Pro Ala Leu Leu
            115                 120                 125

Cys Ser Gly Ala Glu Trp Arg Leu Cys Glu Val Val Glu His Ala Cys
130                 135                 140

Arg Ser Asp Gly Arg Arg Ala Arg Val Thr Cys Ala Glu Asn Arg Ala
145                 150                 155                 160

Leu Arg Leu Val Asp Gly Gly Gly Ala Cys Ala Gly Arg Val Glu Met
                165                 170                 175

Leu Glu His Gly Glu Trp Gly Ser Val Cys Asp Asp Thr Trp Asp Leu
            180                 185                 190

Glu Asp Ala His Val Val Cys Arg Gln Leu Gly Cys Gly Trp Ala Val
            195                 200                 205

Gln Ala Leu Pro Gly Leu His Phe Thr Pro Gly Arg Gly Pro Ile His
        210                 215                 220

Arg Asp Gln Val Asn Cys Ser Gly Ala Glu Ala Tyr Leu Trp Asp Cys
225                 230                 235                 240

Pro Gly Leu Pro Gly Gln His Tyr Cys Gly His Lys Glu Asp Ala Gly
                245                 250                 255

Ala Val Cys Ser Glu His Gln Ser Trp Arg Leu Thr Gly Gly Ala Asp
            260                 265                 270

Arg Cys Glu Gly Gln Val Glu Val His Phe Arg Gly Val Trp Asn Thr
            275                 280                 285

Val Cys Asp Ser Glu Trp Tyr Pro Ser Glu Ala Lys Val Leu Cys Gln
290                 295                 300

Ser Leu Gly Cys Gly Thr Ala Val Glu Arg Pro Lys Gly Leu Pro His
305                 310                 315                 320

Ser Leu Ser Gly Arg Met Tyr Tyr Ser Cys Asn Gly Glu Glu Leu Thr
                325                 330                 335

Leu Ser Asn Cys Ser Trp Arg Phe Asn Asn Ser Asn Leu Cys Ser Gln
            340                 345                 350

Ser Leu Ala Ala Arg Val Leu Cys Ser Ala Ser Arg Ser Leu His Asn
            355                 360                 365

Leu Ser Thr Pro Glu Val Pro Ala Ser Val Gln Thr Val Thr Ile Glu
        370                 375                 380
```

Ser Ser Val Thr Val Lys Ile Glu Asn Lys Ser Arg Glu Leu Met
385                 390                 395                 400

Leu Leu Ile Pro Ser Ile Val Leu Gly Ile Leu Leu Leu Gly Ser Leu
            405                 410                 415

Ile Phe Ile Ala Phe Ile Leu Leu Arg Ile Lys Gly Lys Tyr Val Phe
            420                 425                 430

Met Leu Pro Ile Gln Val Gln Ala Pro Pro Glu Asp Ser Asp Ser
        435                 440                 445

Gly Ser Asp Ser Asp Tyr Glu His Tyr Asp Phe Ser Ala Gln Pro Pro
    450                 455                 460

Val Ala Leu Thr Thr Phe Tyr Asn Ser Gln Arg His Arg Val Thr Asp
465                 470                 475                 480

Glu Glu Val Gln Gln Ser Arg Phe Gln Met Pro Pro Leu Glu Glu Gly
                485                 490                 495

Leu Glu Glu Leu His Ala Ser His Ile Pro Thr Ala Asn Pro Gly His
                500                 505                 510

Cys Ile Thr Asp Pro Pro Ser Leu Gly Pro Gln Tyr His Pro Arg Ser
            515                 520                 525

Asn Ser Glu Ser Ser Thr Ser Ser Gly Glu Asp Tyr Cys Asn Ser Pro
530                 535                 540

Lys Ser Lys Leu Pro Pro Trp Asn Pro Gln Val Phe Ser Ser Glu Arg
545                 550                 555                 560

Ser Ser Phe Leu Glu Gln Pro Asn Leu Glu Leu Ala Gly Thr Gln
            565                 570                 575

Pro Ala Phe Ser Gly Ser Pro Ser Pro Gln Pro Asp Ser Thr Asp Asn
            580                 585                 590

Asp Asp Tyr Asp Asp Ile Ser Ala Ala
            595                 600

<210> SEQ ID NO 4
<211> LENGTH: 123
<212> TYPE: PRT
<213> ORGANISM: Homo sapiens

<400> SEQUENCE: 4

Met Leu Arg Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Trp Lys His Leu Cys Pro Ser Pro Leu
        35                  40                  45

Phe Pro Gly Pro Ser Lys Pro Phe Trp Val Leu Val Val Val Gly Gly
    50                  55                  60

Val Leu Ala Cys Tyr Ser Leu Leu Val Thr Val Ala Phe Ile Ile Phe
65                  70                  75                  80

Trp Val Arg Ser Lys Arg Ser Arg Leu Leu His Ser Asp Tyr Met Asn
                85                  90                  95

Met Thr Pro Arg Arg Pro Gly Pro Thr Arg Lys His Tyr Gln Pro Tyr
            100                 105                 110

Ala Pro Pro Arg Asp Phe Ala Ala Tyr Arg Ser
        115                 120

<210> SEQ ID NO 5
<211> LENGTH: 101
<212> TYPE: PRT
<213> ORGANISM: Homo sapiens -continued

<400> SEQUENCE: 5

Met Leu Arg Leu Leu Leu Ala Leu Asn Leu Phe Pro Ser Ile Gln Val
1               5                   10                  15

Thr Gly Lys His Leu Cys Pro Ser Pro Leu Phe Pro Gly Pro Ser Lys
            20                  25                  30

Pro Phe Trp Val Leu Val Val Val Gly Gly Val Leu Ala Cys Tyr Ser
        35                  40                  45

Leu Leu Val Thr Val Ala Phe Ile Ile Phe Trp Val Arg Ser Lys Arg
    50                  55                  60

Ser Arg Leu Leu His Ser Asp Tyr Met Asn Met Thr Pro Arg Arg Pro
65                  70                  75                  80

Gly Pro Thr Arg Lys His Tyr Gln Pro Tyr Ala Pro Pro Arg Asp Phe
                85                  90                  95

Ala Ala Tyr Arg Ser
            100

<210> SEQ ID NO 6
<211> LENGTH: 220
<212> TYPE: PRT
<213> ORGANISM: Homo sapiens

<400> SEQUENCE: 6

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220

<210> SEQ ID NO 7
<211> LENGTH: 41
<212> TYPE: PRT
<213> ORGANISM: Homo sapiens

<400> SEQUENCE: 7

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 8
<211> LENGTH: 41
<212> TYPE: PRT
<213> ORGANISM: Homo sapiens

<400> SEQUENCE: 8

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 9
<211> LENGTH: 458
<212> TYPE: PRT
<213> ORGANISM: Homo sapiens

<400> SEQUENCE: 9

Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Leu Ala Phe Gln Lys Ala Ser
        195                 200                 205

Ser Ile Val Tyr Lys Lys Glu Gly Glu Gln Val Glu Phe Ser Phe Pro
    210                 215                 220

```
Leu Ala Phe Thr Val Glu Lys Leu Thr Gly Ser Gly Glu Leu Trp Trp
225                 230                 235                 240

Gln Ala Glu Arg Ala Ser Ser Lys Ser Trp Ile Thr Phe Asp Leu
            245                 250                 255

Lys Asn Lys Glu Val Ser Val Lys Arg Val Thr Gln Asp Pro Lys Leu
            260                 265                 270

Gln Met Gly Lys Lys Leu Pro Leu His Leu Thr Leu Pro Gln Ala Leu
            275                 280                 285

Pro Gln Tyr Ala Gly Ser Gly Asn Leu Thr Leu Ala Leu Glu Ala Lys
            290                 295                 300

Thr Gly Lys Leu His Gln Glu Val Asn Leu Val Val Met Arg Ala Thr
305                 310                 315                 320

Gln Leu Gln Lys Asn Leu Thr Cys Glu Val Trp Gly Pro Thr Ser Pro
            325                 330                 335

Lys Leu Met Leu Ser Leu Lys Leu Glu Asn Lys Glu Ala Lys Val Ser
            340                 345                 350

Lys Arg Glu Lys Ala Val Trp Val Leu Asn Pro Glu Ala Gly Met Trp
            355                 360                 365

Gln Cys Leu Leu Ser Asp Ser Gly Gln Val Leu Leu Glu Ser Asn Ile
            370                 375                 380

Lys Val Leu Pro Thr Trp Ser Thr Pro Val Gln Pro Met Ala Leu Ile
385                 390                 395                 400

Val Leu Gly Gly Val Ala Gly Leu Leu Leu Phe Ile Gly Leu Gly Ile
                405                 410                 415

Phe Phe Cys Val Arg Cys Arg His Arg Arg Arg Gln Ala Glu Arg Met
                420                 425                 430

Ser Gln Ile Lys Arg Leu Leu Ser Glu Lys Lys Thr Cys Gln Cys Pro
            435                 440                 445

His Arg Phe Gln Lys Thr Cys Ser Pro Ile
            450                 455

<210> SEQ ID NO 10
<211> LENGTH: 279
<212> TYPE: PRT
<213> ORGANISM: Homo sapiens

<400> SEQUENCE: 10

Met Pro Thr Pro Leu Val His Pro His Leu Pro Ile Ser Ser Pro Arg
1               5                   10                  15

Val Ser Pro Phe Pro Pro Ala Phe Gln Lys Ala Ser Ser Ile Val
            20                  25                  30

Tyr Lys Lys Glu Gly Glu Gln Val Glu Phe Ser Phe Pro Leu Ala Phe
            35                  40                  45

Thr Val Glu Lys Leu Thr Gly Ser Gly Glu Leu Trp Trp Gln Ala Glu
        50                  55                  60

Arg Ala Ser Ser Lys Ser Trp Ile Thr Phe Asp Leu Lys Asn Lys
65                  70                  75                  80

Glu Val Ser Val Lys Arg Val Thr Gln Asp Pro Lys Leu Gln Met Gly
                85                  90                  95

Lys Lys Leu Pro Leu His Leu Thr Leu Pro Gln Ala Leu Pro Gln Tyr
            100                 105                 110

Ala Gly Ser Gly Asn Leu Thr Leu Ala Leu Glu Ala Lys Thr Gly Lys
        115                 120                 125

Leu His Gln Glu Val Asn Leu Val Val Met Arg Ala Thr Gln Leu Gln
130                 135                 140
```

```
Lys Asn Leu Thr Cys Glu Val Trp Gly Pro Thr Ser Pro Lys Leu Met
145                 150                 155                 160

Leu Ser Leu Lys Leu Glu Asn Lys Glu Ala Lys Val Ser Lys Arg Glu
                165                 170                 175

Lys Ala Val Trp Val Leu Asn Pro Glu Ala Gly Met Trp Gln Cys Leu
            180                 185                 190

Leu Ser Asp Ser Gly Gln Val Leu Glu Ser Asn Ile Lys Val Leu
                195                 200                 205

Pro Thr Trp Ser Thr Pro Val Gln Pro Met Ala Leu Ile Val Leu Gly
        210                 215                 220

Gly Val Ala Gly Leu Leu Leu Phe Ile Gly Leu Gly Ile Phe Phe Cys
225                 230                 235                 240

Val Arg Cys Arg His Arg Arg Arg Gln Ala Glu Arg Met Ser Gln Ile
                245                 250                 255

Lys Arg Leu Leu Ser Glu Lys Lys Thr Cys Gln Cys Pro His Arg Phe
            260                 265                 270

Gln Lys Thr Cys Ser Pro Ile
            275
```

<210> SEQ ID NO 11
<211> LENGTH: 185
<212> TYPE: PRT
<213> ORGANISM: Homo sapiens

<400> SEQUENCE: 11

```
Met Gly Lys Lys Leu Pro Leu His Leu Thr Leu Pro Gln Ala Leu Pro
1               5                   10                  15

Gln Tyr Ala Gly Ser Gly Asn Leu Thr Leu Ala Leu Glu Ala Lys Thr
            20                  25                  30

Gly Lys Leu His Gln Glu Val Asn Leu Val Val Met Arg Ala Thr Gln
        35                  40                  45

Leu Gln Lys Asn Leu Thr Cys Glu Val Trp Gly Pro Thr Ser Pro Lys
    50                  55                  60

Leu Met Leu Ser Leu Lys Leu Glu Asn Lys Glu Ala Lys Val Ser Lys
65                  70                  75                  80

Arg Glu Lys Ala Val Trp Val Leu Asn Pro Glu Ala Gly Met Trp Gln
                85                  90                  95

Cys Leu Leu Ser Asp Ser Gly Gln Val Leu Glu Ser Asn Ile Lys
            100                 105                 110

Val Leu Pro Thr Trp Ser Thr Pro Val Gln Pro Met Ala Leu Ile Val
            115                 120                 125

Leu Gly Gly Val Ala Gly Leu Leu Leu Phe Ile Gly Leu Gly Ile Phe
130                 135                 140

Phe Cys Val Arg Cys Arg His Arg Arg Arg Gln Ala Glu Arg Met Ser
145                 150                 155                 160

Gln Ile Lys Arg Leu Leu Ser Glu Lys Lys Thr Cys Gln Cys Pro His
                165                 170                 175

Arg Phe Gln Lys Thr Cys Ser Pro Ile
            180                 185
```

<210> SEQ ID NO 12
<211> LENGTH: 185
<212> TYPE: PRT
<213> ORGANISM: Homo sapiens

<400> SEQUENCE: 12

```
Met Gly Lys Lys Leu Pro Leu His Leu Thr Leu Pro Gln Ala Leu Pro
1               5                   10                  15

Gln Tyr Ala Gly Ser Gly Asn Leu Thr Leu Ala Leu Glu Ala Lys Thr
            20                  25                  30

Gly Lys Leu His Gln Glu Val Asn Leu Val Val Met Arg Ala Thr Gln
            35                  40                  45

Leu Gln Lys Asn Leu Thr Cys Glu Val Trp Gly Pro Thr Ser Pro Lys
    50                  55                  60

Leu Met Leu Ser Leu Lys Leu Glu Asn Lys Glu Ala Lys Val Ser Lys
65                  70                  75                  80

Arg Glu Lys Ala Val Trp Val Leu Asn Pro Glu Ala Gly Met Trp Gln
                85                  90                  95

Cys Leu Leu Ser Asp Ser Gly Gln Val Leu Leu Glu Ser Asn Ile Lys
                100                 105                 110

Val Leu Pro Thr Trp Ser Thr Pro Val Gln Pro Met Ala Leu Ile Val
            115                 120                 125

Leu Gly Gly Val Ala Gly Leu Leu Leu Phe Ile Gly Leu Gly Ile Phe
    130                 135                 140

Phe Cys Val Arg Cys Arg His Arg Arg Gln Ala Glu Arg Met Ser
145                 150                 155                 160

Gln Ile Lys Arg Leu Leu Ser Glu Lys Lys Thr Cys Gln Cys Pro His
                165                 170                 175

Arg Phe Gln Lys Thr Cys Ser Pro Ile
            180                 185

<210> SEQ ID NO 13
<211> LENGTH: 185
<212> TYPE: PRT
<213> ORGANISM: Homo sapiens

<400> SEQUENCE: 13

Met Gly Lys Lys Leu Pro Leu His Leu Thr Leu Pro Gln Ala Leu Pro
1               5                   10                  15

Gln Tyr Ala Gly Ser Gly Asn Leu Thr Leu Ala Leu Glu Ala Lys Thr
            20                  25                  30

Gly Lys Leu His Gln Glu Val Asn Leu Val Val Met Arg Ala Thr Gln
            35                  40                  45

Leu Gln Lys Asn Leu Thr Cys Glu Val Trp Gly Pro Thr Ser Pro Lys
    50                  55                  60

Leu Met Leu Ser Leu Lys Leu Glu Asn Lys Glu Ala Lys Val Ser Lys
65                  70                  75                  80

Arg Glu Lys Ala Val Trp Val Leu Asn Pro Glu Ala Gly Met Trp Gln
                85                  90                  95

Cys Leu Leu Ser Asp Ser Gly Gln Val Leu Leu Glu Ser Asn Ile Lys
                100                 105                 110

Val Leu Pro Thr Trp Ser Thr Pro Val Gln Pro Met Ala Leu Ile Val
            115                 120                 125

Leu Gly Gly Val Ala Gly Leu Leu Leu Phe Ile Gly Leu Gly Ile Phe
    130                 135                 140

Phe Cys Val Arg Cys Arg His Arg Arg Gln Ala Glu Arg Met Ser
145                 150                 155                 160

Gln Ile Lys Arg Leu Leu Ser Glu Lys Lys Thr Cys Gln Cys Pro His
                165                 170                 175

Arg Phe Gln Lys Thr Cys Ser Pro Ile
```

180                 185

<210> SEQ ID NO 14
<211> LENGTH: 42
<212> TYPE: PRT
<213> ORGANISM: Homo sapiens

<400> SEQUENCE: 14

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Gly Gly Cys Glu Leu
        35                  40

<210> SEQ ID NO 15
<211> LENGTH: 255
<212> TYPE: PRT
<213> ORGANISM: Homo sapiens

<400> SEQUENCE: 15

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Gly Gly Cys Glu Leu
                245                 250                 255

<210> SEQ ID NO 16
<211> LENGTH: 199
<212> TYPE: PRT

<213> ORGANISM: Homo sapiens

<400> SEQUENCE: 16

Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

Gln Gln Phe Lys Met Gln Leu Leu Lys Gly Gln Ile Leu Cys Asp
    50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Asn Ser Val Ser Phe Phe Leu
                85                  90                  95

Tyr Asn Leu Asp His Ser His Ala Asn Tyr Tyr Phe Cys Asn Leu Ser
            100                 105                 110

Ile Phe Asp Pro Pro Phe Lys Val Thr Leu Thr Gly Gly Tyr Leu
        115                 120                 125

His Ile Tyr Glu Ser Gln Leu Cys Cys Gln Leu Lys Phe Trp Leu Pro
    130                 135                 140

Ile Gly Cys Ala Ala Phe Val Val Cys Ile Leu Gly Cys Ile Leu
145                 150                 155                 160

Ile Cys Trp Leu Thr Lys Lys Lys Tyr Ser Ser Ser Val His Asp Pro
                165                 170                 175

Asn Gly Glu Tyr Met Phe Met Arg Ala Val Asn Thr Ala Lys Lys Ser
            180                 185                 190

Arg Leu Thr Asp Val Thr Leu
        195

<210> SEQ ID NO 17
<211> LENGTH: 41
<212> TYPE: PRT
<213> ORGANISM: Homo sapiens

<400> SEQUENCE: 17

Ala Val Ser Leu Ser Lys Met Leu Lys Lys Arg Ser Pro Leu Thr Thr
1               5                   10                  15

Gly Val Tyr Val Lys Met Pro Pro Thr Glu Pro Glu Cys Glu Lys Gln
            20                  25                  30

Phe Gln Pro Tyr Phe Ile Pro Ile Asn
        35                  40

<210> SEQ ID NO 18
<211> LENGTH: 327
<212> TYPE: DNA
<213> ORGANISM: Artificial Sequence
<220> FEATURE:
<223> OTHER INFORMATION: portion of antibody

<400> SEQUENCE: 18
gacatccaaa tgacacaaag tcctagctct ctctcagcaa gtgttggcga ccgtgtgacc    60
atcacatgta aagcttcaag ggatattcgc agctacctga cttggtacca acaaaagccc   120
ggaaaagcgc ctaaaacgct tatttactat gccaccagcc tcgcagatgg tgtcccctcc   180
agattttctg gatcgggatc agggcaagat tatagtctta cgatatcgag tcttgagtcg   240
gacgatactg ccacatacta ctgcttacag cacggggaaa gcccattcac attcggaagt   300

```
ggtacgaaac tcgagatcaa acgggca                                         327

<210> SEQ ID NO 19
<211> LENGTH: 357
<212> TYPE: DNA
<213> ORGANISM: Artificial
<220> FEATURE:
<223> OTHER INFORMATION: portion of antibody

<400> SEQUENCE: 19
gaagtccaat tggtcgagag cggaggtggg cttgttaaac caggaggcag tttaaaatta     60
tcatgtgctg cctcgggttt caagttctcg cggtatgcta tgtcctgggt acgccaagca    120
cctggaaagc gtttagaatg ggtggccaca attagtagtg gtggttcata tatatattat    180
cccgactccg tcaaggaag gttcacgatt tcaaggaca atgtgaagaa caccctctac      240
ttacagatga gtagtctgcg ttctgaggat accgctatgt actactgtgc tcggagagat    300
tacgatctgg attatttcga cagctggggt cagggcacac tcgttacagt atcctcg       357

<210> SEQ ID NO 20
<211> LENGTH: 60
<212> TYPE: DNA
<213> ORGANISM: Artificial Sequence
<220> FEATURE:
<223> OTHER INFORMATION: portion of antibody

<400> SEQUENCE: 20
gtccaacttg ttgaatcagg tgggggctg gtcaaacccg ggggctctct gaaactaagt      60

<210> SEQ ID NO 21
<211> LENGTH: 45
<212> TYPE: DNA
<213> ORGANISM: Artificial Sequence
<220> FEATURE:
<223> OTHER INFORMATION: portion of antibody

<400> SEQUENCE: 21
ttctctcggt acgctatgtc gtgggtcaga caagcgcccg gcaaa                      45

<210> SEQ ID NO 22
<211> LENGTH: 57
<212> TYPE: DNA
<213> ORGANISM: Artificial Sequence
<220> FEATURE:
<223> OTHER INFORMATION: portion of antibody

<400> SEQUENCE: 22
cgtgattatg atctagacta ctttgactcc tggggtcaag gtacgctcgt gacggtt        57

<210> SEQ ID NO 23
<211> LENGTH: 22
<212> TYPE: PRT
<213> ORGANISM: Homo sapiens

<400> SEQUENCE: 23

Met Ala Leu Ile Val Leu Gly Gly Val Ala Gly Leu Leu Leu Phe Ile
1               5                   10                  15

Gly Leu Gly Ile Phe Phe
            20

<210> SEQ ID NO 24
<211> LENGTH: 66
<212> TYPE: DNA
```

<213> ORGANISM: Homo sapiens

<400> SEQUENCE: 24
atggccctga ttgtgctggg gggcgtcgcc ggcctcctgc ttttcattgg gctaggcatc    60
ttcttc    66

<210> SEQ ID NO 25
<211> LENGTH: 21
<212> TYPE: PRT
<213> ORGANISM: Artificial Sequence
<220> FEATURE:
<223> OTHER INFORMATION: linker

<400> SEQUENCE: 25

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 26
<211> LENGTH: 54
<212> TYPE: DNA
<213> ORGANISM: Artificial Sequence
<220> FEATURE:
<223> OTHER INFORMATION: linker

<400> SEQUENCE: 26
gggtcaacgt cgggcggggg ttccggtgga ggaagtggag gtggtggaag ttct    54

<210> SEQ ID NO 27
<211> LENGTH: 60
<212> TYPE: DNA
<213> ORGANISM: Artificial Sequence
<220> FEATURE:
<223> OTHER INFORMATION: linker

<400> SEQUENCE: 27
ggcggcggcg gaagtggcgg cggcggctca ggcggggggg gttctggggg cggcggttca    60

<210> SEQ ID NO 28
<211> LENGTH: 20
<212> TYPE: PRT
<213> ORGANISM: Artificial Sequence
<220> FEATURE:
<223> OTHER INFORMATION: portion of antibody

<400> SEQUENCE: 28

Val Gln Leu Val Glu Ser Gly Gly Gly Leu Val Lys Pro Gly Gly Ser
1               5                   10                  15

Leu Lys Leu Ser
            20

<210> SEQ ID NO 29
<211> LENGTH: 15
<212> TYPE: PRT
<213> ORGANISM: Artificial Sequence
<220> FEATURE:
<223> OTHER INFORMATION: portion of antibody

<400> SEQUENCE: 29

Phe Ser Arg Tyr Ala Met Ser Trp Val Arg Gln Ala Pro Gly Lys
1               5                   10                  15

<210> SEQ ID NO 30

```
<211> LENGTH: 19
<212> TYPE: PRT
<213> ORGANISM: Artificial Sequence
<220> FEATURE:
<223> OTHER INFORMATION: portion of antibody

<400> SEQUENCE: 30

Arg Asp Tyr Asp Leu Asp Tyr Phe Asp Ser Trp Gly Gln Gly Thr Leu
1               5                   10                  15

Val Thr Val

<210> SEQ ID NO 31
<211> LENGTH: 38
<212> TYPE: PRT
<213> ORGANISM: Artificial Sequence
<220> FEATURE:
<223> OTHER INFORMATION: portion of antibody

<400> SEQUENCE: 31

Cys Trp Leu Thr Lys Lys Lys Tyr Ser Ser Val His Asp Pro Asn
1               5                   10                  15

Gly Glu Tyr Met Phe Met Arg Ala Val Asn Thr Ala Lys Lys Ser Arg
                20                  25                  30

Leu Thr Asp Val Thr Leu
        35

<210> SEQ ID NO 32
<211> LENGTH: 42
<212> TYPE: PRT
<213> ORGANISM: Artificial Sequence
<220> FEATURE:
<223> OTHER INFORMATION: portion of antibody

<400> SEQUENCE: 32

Ala Leu Tyr Leu Leu Arg Arg Asp Gln Arg Leu Pro Pro Asp Ala His
1               5                   10                  15

Lys Pro Pro Gly Gly Gly Ser Phe Arg Thr Pro Ile Gln Glu Glu Gln
                20                  25                  30

Ala Asp Ala His Ser Thr Leu Ala Lys Ile
        35                  40

<210> SEQ ID NO 33
<211> LENGTH: 97
<212> TYPE: PRT
<213> ORGANISM: Artificial Sequence
<220> FEATURE:
<223> OTHER INFORMATION: portion of antibody

<400> SEQUENCE: 33

Cys Ser Arg Ala Ala Arg Gly Thr Ile Gly Ala Arg Arg Thr Gly Gln
1               5                   10                  15

Pro Leu Lys Glu Asp Pro Ser Ala Val Pro Val Phe Ser Val Asp Tyr
                20                  25                  30

Gly Glu Leu Asp Phe Gln Trp Arg Glu Lys Thr Pro Glu Pro Pro Val
        35                  40                  45

Pro Cys Val Pro Glu Gln Thr Glu Tyr Ala Thr Ile Val Phe Pro Ser
    50                  55                  60

Gly Met Gly Thr Ser Ser Pro Ala Arg Arg Gly Ser Ala Asp Gly Pro
65                  70                  75                  80

Arg Ser Ala Gln Pro Leu Arg Pro Glu Asp Gly His Cys Ser Trp Pro
                85                  90                  95
```

Leu

```
<210> SEQ ID NO 34
<211> LENGTH: 109
<212> TYPE: PRT
<213> ORGANISM: Artificial Sequence
<220> FEATURE:
<223> OTHER INFORMATION: portion of antibody

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Ile Arg Ser Tyr
            20                  25                  30

Leu Thr Trp Tyr Gln Gln Lys Pro Gly Lys Ala Pro Lys Thr Leu Ile
        35                  40                  45

Tyr Tyr Ala Thr Ser Leu Ala Asp Gly Val Pro Ser Arg Phe Ser Gly
    50                  55                  60

Ser Gly Ser Gly Gln Asp Tyr Ser Leu Thr Ile Ser Ser Leu Glu Ser
65                  70                  75                  80

Asp Asp Thr Ala Thr Tyr Tyr Cys Leu Gln His Gly Glu Ser Pro Phe
                85                  90                  95

Thr Phe Gly Ser Gly Thr Lys Leu Glu Ile Lys Arg Ala
            100                 105

<210> SEQ ID NO 35
<211> LENGTH: 119
<212> TYPE: PRT
<213> ORGANISM: Artificial Sequence
<220> FEATURE:
<223> OTHER INFORMATION: portion of antibody

<400> SEQUENCE: 35

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Lys Phe Ser Arg Tyr
            20                  25                  30

Ala Met Ser Trp Val Arg Gln Ala Pro Gly Lys Arg Leu Glu Trp Val
        35                  40                  45

Ala Thr Ile Ser Ser Gly Gly Ser Tyr Ile Tyr Tyr Pro Asp Ser Val
    50                  55                  60

Lys Gly Arg Phe Thr Ile Ser Arg Asp Asn Val Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Arg Asp Tyr Asp Leu Asp Tyr Phe Asp Ser Trp Gly Gln Gly
            100                 105                 110

Thr Leu Val Thr Val Ser Ser
        115

<210> SEQ ID NO 36
<211> LENGTH: 18
<212> TYPE: PRT
<213> ORGANISM: Artificial Sequence
<220> FEATURE:
<223> OTHER INFORMATION: linker

<400> SEQUENCE: 36

Gly Ser Thr Ser Gly Gly Gly Ser Gly Gly Gly Ser Gly Gly Gly Gly
1               5                   10                  15
```

Ser Ser

<210> SEQ ID NO 37
<211> LENGTH: 20
<212> TYPE: PRT
<213> ORGANISM: Artificial Sequence
<220> FEATURE:
<223> OTHER INFORMATION: linker

<400> SEQUENCE: 37

Gly Gly Gly Gly Ser Gly Gly Gly Ser Gly Gly Gly Ser Gly
1               5                   10                  15

Gly Gly Gly Ser
            20

<210> SEQ ID NO 38
<211> LENGTH: 246
<212> TYPE: PRT
<213> ORGANISM: Artificial Sequence
<220> FEATURE:
<223> OTHER INFORMATION: portion of antibody

<400> SEQUENCE: 38

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Lys Phe Ser Arg Tyr
            20                  25                  30

Ala Met Ser Trp Val Arg Gln Ala Pro Gly Lys Arg Leu Glu Trp Val
        35                  40                  45

Ala Thr Ile Ser Ser Gly Gly Ser Tyr Ile Tyr Tyr Pro Asp Ser Val
    50                  55                  60

Lys Gly Arg Phe Thr Ile Ser Arg Asp Asn Val Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Arg Asp Tyr Asp Leu Asp Tyr Phe Asp Ser Trp Gly Gln Gly
            100                 105                 110

Thr Leu Val Thr Val Ser Ser Gly Ser Thr Ser Gly Gly Gly Ser Gly
        115                 120                 125

Gly Gly Ser Gly Gly Gly Ser Ser Asp Ile Gln Met Thr Gln Ser
    130                 135                 140

Pro Ser Ser Leu Ser Ala Ser Val Gly Asp Arg Val Thr Ile Thr Cys
145                 150                 155                 160

Lys Ala Ser Arg Asp Ile Arg Ser Tyr Leu Thr Trp Tyr Gln Gln Lys
                165                 170                 175

Pro Gly Lys Ala Pro Lys Thr Leu Ile Tyr Tyr Ala Thr Ser Leu Ala
            180                 185                 190

Asp Gly Val Pro Ser Arg Phe Ser Gly Ser Gly Ser Gly Gln Asp Tyr
        195                 200                 205

Ser Leu Thr Ile Ser Ser Leu Glu Ser Asp Asp Thr Ala Thr Tyr Tyr
    210                 215                 220

Cys Leu Gln His Gly Glu Ser Pro Phe Thr Phe Gly Ser Gly Thr Lys
225                 230                 235                 240

Leu Glu Ile Lys Arg Ala
                245

<210> SEQ ID NO 39

```
<211> LENGTH: 248
<212> TYPE: PRT
<213> ORGANISM: Artificial Sequence
<220> FEATURE:
<223> OTHER INFORMATION: portion of antibody

<400> SEQUENCE: 39

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Lys Phe Ser Arg Tyr
            20                  25                  30

Ala Met Ser Trp Val Arg Gln Ala Pro Gly Lys Arg Leu Glu Trp Val
        35                  40                  45

Ala Thr Ile Ser Ser Gly Gly Ser Tyr Ile Tyr Tyr Pro Asp Ser Val
    50                  55                  60

Lys Gly Arg Phe Thr Ile Ser Arg Asp Asn Val Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Arg Asp Tyr Asp Leu Asp Tyr Phe Asp Ser Trp Gly Gln Gly
            100                 105                 110

Thr Leu Val Thr Val Ser Ser Gly Gly Gly Ser Gly Gly Gly Gly Gly
        115                 120                 125

Ser Gly Gly Gly Ser Gly Gly Gly Ser Asp Ile Gln Met Thr
130                 135                 140

Gln Ser Pro Ser Ser Leu Ser Ala Ser Val Gly Asp Arg Val Thr Ile
145                 150                 155                 160

Thr Cys Lys Ala Ser Arg Asp Ile Arg Ser Tyr Leu Thr Trp Tyr Gln
                165                 170                 175

Gln Lys Pro Gly Lys Ala Pro Lys Thr Leu Ile Tyr Tyr Ala Thr Ser
            180                 185                 190

Leu Ala Asp Gly Val Pro Ser Arg Phe Ser Gly Ser Gly Ser Gly Gln
        195                 200                 205

Asp Tyr Ser Leu Thr Ile Ser Ser Leu Glu Ser Asp Asp Thr Ala Thr
    210                 215                 220

Tyr Tyr Cys Leu Gln His Gly Glu Ser Pro Phe Thr Phe Gly Ser Gly
225                 230                 235                 240

Thr Lys Leu Glu Ile Lys Arg Ala
                245

<210> SEQ ID NO 40
<211> LENGTH: 246
<212> TYPE: PRT
<213> ORGANISM: Artificial Sequence
<220> FEATURE:
<223> OTHER INFORMATION: portion of antibody

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Ile Arg Ser Tyr
            20                  25                  30

Leu Thr Trp Tyr Gln Gln Lys Pro Gly Lys Ala Pro Lys Thr Leu Ile
        35                  40                  45

Tyr Tyr Ala Thr Ser Leu Ala Asp Gly Val Pro Ser Arg Phe Ser Gly
    50                  55                  60

Ser Gly Ser Gly Gln Asp Tyr Ser Leu Thr Ile Ser Ser Leu Glu Ser
```

```
65                  70                  75                  80
Asp Asp Thr Ala Thr Tyr Tyr Cys Leu Gln His Gly Glu Ser Pro Phe
                85                  90                  95

Thr Phe Gly Ser Gly Thr Lys Leu Glu Ile Lys Arg Ala Gly Ser Thr
            100                 105                 110

Ser Gly Gly Gly Ser Gly Gly Ser Gly Gly Gly Ser Ser Glu
            115                 120                 125

Val Gln Leu Val Glu Ser Gly Gly Leu Val Lys Pro Gly Ser
    130                 135                 140

Leu Lys Leu Ser Cys Ala Ala Ser Gly Phe Lys Phe Ser Arg Tyr Ala
145                 150                 155                 160

Met Ser Trp Val Arg Gln Ala Pro Gly Lys Arg Leu Glu Trp Val Ala
                165                 170                 175

Thr Ile Ser Ser Gly Gly Ser Tyr Ile Tyr Tyr Pro Asp Ser Val Lys
            180                 185                 190

Gly Arg Phe Thr Ile Ser Arg Asp Asn Val Lys Asn Thr Leu Tyr Leu
            195                 200                 205

Gln Met Ser Ser Leu Arg Ser Glu Asp Thr Ala Met Tyr Tyr Cys Ala
    210                 215                 220

Arg Arg Asp Tyr Asp Leu Asp Tyr Phe Asp Ser Trp Gly Gln Gly Thr
225                 230                 235                 240

Leu Val Thr Val Ser Ser
                245

<210> SEQ ID NO 41
<211> LENGTH: 248
<212> TYPE: PRT
<213> ORGANISM: Artificial Sequence
<220> FEATURE:
<223> OTHER INFORMATION: portion of antibody

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Ile Arg Ser Tyr
            20                  25                  30

Leu Thr Trp Tyr Gln Gln Lys Pro Gly Lys Ala Pro Lys Thr Leu Ile
        35                  40                  45

Tyr Tyr Ala Thr Ser Leu Ala Asp Gly Val Pro Ser Arg Phe Ser Gly
    50                  55                  60

Ser Gly Ser Gly Gln Asp Tyr Ser Leu Thr Ile Ser Ser Leu Glu Ser
65                  70                  75                  80

Asp Asp Thr Ala Thr Tyr Tyr Cys Leu Gln His Gly Glu Ser Pro Phe
                85                  90                  95

Thr Phe Gly Ser Gly Thr Lys Leu Glu Ile Lys Arg Ala Gly Gly Gly
            100                 105                 110

Gly Ser Gly Gly Gly Gly Ser Gly Gly Gly Ser Gly Gly Gly
        115                 120                 125

Ser Glu Val Gln Leu Val Glu Ser Gly Gly Leu Val Lys Pro Gly
    130                 135                 140

Gly Ser Leu Lys Leu Ser Cys Ala Ala Ser Gly Phe Lys Phe Ser Arg
145                 150                 155                 160

Tyr Ala Met Ser Trp Val Arg Gln Ala Pro Gly Lys Arg Leu Glu Trp
                165                 170                 175

Val Ala Thr Ile Ser Ser Gly Gly Ser Tyr Ile Tyr Tyr Pro Asp Ser
```

```
                180             185             190
Val Lys Gly Arg Phe Thr Ile Ser Arg Asp Asn Val Lys Asn Thr Leu
        195                 200                 205

Tyr Leu Gln Met Ser Ser Leu Arg Ser Glu Asp Thr Ala Met Tyr Tyr
        210                 215                 220

Cys Ala Arg Arg Asp Tyr Asp Leu Asp Tyr Phe Asp Ser Trp Gly Gln
225                 230                 235                 240

Gly Thr Leu Val Thr Val Ser Ser
                245

<210> SEQ ID NO 42
<211> LENGTH: 738
<212> TYPE: DNA
<213> ORGANISM: Artificial Sequence
<220> FEATURE:
<223> OTHER INFORMATION: portion of antibody

<400> SEQUENCE: 42
gaagtccaat tggtcgagag cggaggtggg cttgttaaac caggaggcag tttaaaatta      60
tcatgtgctg cctcgggttt caagttctcg cggtatgcta tgtcctgggt acgccaagca    120
cctggaaagc gtttagaatg ggtggccaca attagtagtg gtggttcata tatatattat    180
cccgactccg tcaaaggaag gttcacgatt tcaagggaca atgtgaagaa caccctctac    240
ttacagatga gtagtctgcg ttctgaggat accgctatgt actactgtgc tcggagagat    300
tacgatctgg attatttcga cagctggggt cagggcacac tcgttacagt atcctcgggg    360
tcaacgtcgg gcggggggttc cggtggagga agtggaggtg gtggaagttc tgacatccaa    420
atgacacaaa gtcctagctc tctctcagca agtgttggcg accgtgtgac catcacatgt    480
aaagcttcaa gggatattcg cagctacctg acttggtacc aacaaaagcc cggaaaagcg    540
cctaaaacgc ttatttacta tgccaccagc ctcgcagatg gtgtcccctc agattttct    600 ggatcgggat cagggcaaga ttatagtctt acgatatcga gtcttgagtc ggacgatact    660
gccacatact actgcttaca gcacggggaa agcccattca cattcggaag tggtacgaaa    720
ctcgagatca aacgggca                                                   738

<210> SEQ ID NO 43
<211> LENGTH: 744
<212> TYPE: DNA
<213> ORGANISM: Artificial Sequence
<220> FEATURE:
<223> OTHER INFORMATION: portion of antibody

<400> SEQUENCE: 43
gaagtccaat tggtcgagag cggaggtggg cttgttaaac caggaggcag tttaaaatta      60
tcatgtgctg cctcgggttt caagttctcg cggtatgcta tgtcctgggt acgccaagca    120
cctggaaagc gtttagaatg ggtggccaca attagtagtg gtggttcata tatatattat    180
cccgactccg tcaaaggaag gttcacgatt tcaagggaca atgtgaagaa caccctctac    240
ttacagatga gtagtctgcg ttctgaggat accgctatgt actactgtgc tcggagagat    300
tacgatctgg attatttcga cagctggggt cagggcacac tcgttacagt atcctcgggc    360
ggcggcggaa gtggcggcgg cggctcaggc ggggggggtt ctggggggcgg cggttcagac    420 atccaaatga cacaaagtcc tagctctctc tcagcaagtg ttggcgaccg tgtgaccatc    480
acatgtaaag cttcaaggga tattcgcagc tacctgactt ggtaccaaca aaagcccgga    540
aaagcgccta aaacgcttat ttactatgcc accagcctcg cagatggtgt cccctccaga    600
```

| | |
|---|---|
| ttttctggat cgggatcagg gcaagattat agtcttacga tatcgagtct tgagtcggac | 660 |
| gatactgcca catactactg cttacagcac ggggaaagcc cattcacatt cggaagtggt | 720 |
| acgaaactcg agatcaaacg ggca | 744 |

<210> SEQ ID NO 44
<211> LENGTH: 738
<212> TYPE: DNA
<213> ORGANISM: Artificial Sequence
<220> FEATURE:
<223> OTHER INFORMATION: portion of antibody

<400> SEQUENCE: 44

| | |
|---|---|
| gacatccaaa tgacacaaag tcctagctct ctctcagcaa gtgttggcga ccgtgtgacc | 60 |
| atcacatgta aagcttcaag ggatattcgc agctacctga cttggtacca acaaaagccc | 120 |
| ggaaaagcgc ctaaaacgct tatttactat gccaccagcc tcgcagatgg tgtcccctcc | 180 |
| agattttctg gatcgggatc agggcaagat tatagtctta cgatatcgag tcttgagtcg | 240 |
| gacgatactg ccacatacta ctgcttacag cacggggaaa gcccattcac attcggaagt | 300 |
| ggtacgaaac tcgagatcaa acgggcaggg tcaacgtcgg cgggggttc cggtggagga | 360 |
| agtggaggtg gtggaagttc tgaagtccaa ttggtcgaga gcggaggtgg gcttgttaaa | 420 |
| ccaggaggca gtttaaaatt atcatgtgct gcctcgggtt tcaagttctc gcggtatgct | 480 |
| atgtcctggg tacgccaagc acctggaaag cgtttagaat gggtggccac aattagtagt | 540 |
| ggtggttcat atatatatta tcccgactcc gtcaaaggaa ggttcacgat ttcaagggac | 600 |
| aatgtgaaga acaccctcta cttacagatg agtagtctgc gttctgagga taccgctatg | 660 |
| tactactgtg ctcggagaga ttacgatctg gattatttcg acagctgggg tcagggcaca | 720 |
| ctcgttacag tatcctcg | 738 |

<210> SEQ ID NO 45
<211> LENGTH: 744
<212> TYPE: DNA
<213> ORGANISM: Artificial Sequence
<220> FEATURE:
<223> OTHER INFORMATION: portion of antibody

<400> SEQUENCE: 45

| | |
|---|---|
| gacatccaaa tgacacaaag tcctagctct ctctcagcaa gtgttggcga ccgtgtgacc | 60 |
| atcacatgta aagcttcaag ggatattcgc agctacctga cttggtacca acaaaagccc | 120 |
| ggaaaagcgc ctaaaacgct tatttactat gccaccagcc tcgcagatgg tgtcccctcc | 180 |
| agattttctg gatcgggatc agggcaagat tatagtctta cgatatcgag tcttgagtcg | 240 |
| gacgatactg ccacatacta ctgcttacag cacggggaaa gcccattcac attcggaagt | 300 |
| ggtacgaaac tcgagatcaa acgggcaggc ggcggcggaa gtggcggcgg cggctcaggc | 360 |
| gggggggtt ctggggcgg cggttcagaa gtccaattgg tcgagagcgg aggtgggctt | 420 |
| gttaaaccag gaggcagttt aaaattatca tgtgctgcct cgggtttcaa gttctcgcgg | 480 |
| tatgctatgt cctgggtacg ccaagcacct ggaaagcgtt tagaatgggt ggccacaatt | 540 |
| agtagtggtg gttcatatat atattatccc gactccgtca aaggaaggtt cacgatttca | 600 |
| agggacaatg tgaagaacac cctctactta cagatgagta gtctgcgttc tgaggatacc | 660 |
| gctatgtact actgtgctcg gagagattac gatctggatt atttcgacag ctggggtcag | 720 |
| ggcacactcg ttacagtatc ctcg | 744 |

<210> SEQ ID NO 46
<211> LENGTH: 235
<212> TYPE: PRT
<213> ORGANISM: Homo sapiens

<400> SEQUENCE: 46

Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Asn His
        195                 200                 205

Arg Asn Arg Arg Arg Val Cys Lys Cys Pro Arg Pro Val Val Lys Ser
210                 215                 220

Gly Asp Lys Pro Ser Leu Ser Ala Arg Tyr Val
225                 230                 235

<210> SEQ ID NO 47
<211> LENGTH: 198
<212> TYPE: PRT
<213> ORGANISM: Homo sapiens

<400> SEQUENCE: 47

Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

```
Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
            115                 120                 125

Val Pro Val Phe Leu Pro Ala Lys Pro Thr Thr Thr Pro Ala Pro Arg
            130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Gly Asn Arg Arg Arg
                165                 170                 175

Val Cys Lys Cys Pro Arg Pro Val Val Lys Ser Gly Asp Lys Pro Ser
            180                 185                 190

Leu Ser Ala Arg Tyr Val
            195

<210> SEQ ID NO 48
<211> LENGTH: 235
<212> TYPE: PRT
<213> ORGANISM: Homo sapiens

<400> SEQUENCE: 48

Met Ala Leu Pro Val Thr Ala Leu Leu Leu Pro Leu Ala Leu Leu Leu
1                   5                   10                  15

His Ala Ala Arg Pro Ser Gln Phe Arg Val Ser Pro Leu Asp Arg Thr
                20                  25                  30

Trp Asn Leu Gly Glu Thr Val Glu Leu Lys Cys Gln Val Leu Leu Ser
            35                  40                  45

Asn Pro Thr Ser Gly Cys Ser Trp Leu Phe Gln Pro Arg Gly Ala Ala
50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
            115                 120                 125

Val Pro Val Phe Leu Pro Ala Lys Pro Thr Thr Thr Pro Ala Pro Arg
            130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Asn His
            195                 200                 205

Arg Asn Arg Arg Arg Val Cys Lys Cys Pro Arg Pro Val Val Lys Ser
        210                 215                 220

Gly Asp Lys Pro Ser Leu Ser Ala Arg Tyr Val
225                 230                 235

<210> SEQ ID NO 49
<211> LENGTH: 246
<212> TYPE: PRT
<213> ORGANISM: Homo sapiens
```

<400> SEQUENCE: 49

```
Met Arg Pro Arg Leu Trp Leu Leu Leu Ala Ala Gln Leu Thr Val Leu
1               5                   10                  15

His Gly Asn Ser Val Leu Gln Gln Thr Pro Ala Tyr Ile Lys Val Gln
            20                  25                  30

Thr Asn Lys Met Val Met Leu Ser Cys Glu Ala Lys Ile Ser Leu Ser
        35                  40                  45

Asn Met Arg Ile Tyr Trp Leu Arg Gln Arg Gln Ala Pro Ser Ser Asp
50                  55                  60

Ser His His Glu Phe Leu Ala Leu Trp Asp Ser Ala Lys Gly Thr Ile
65                  70                  75                  80

His Gly Glu Glu Val Glu Gln Glu Lys Ile Ala Val Phe Arg Asp Ala
                85                  90                  95

Ser Arg Phe Ile Leu Asn Leu Thr Ser Val Lys Pro Glu Asp Ser Gly
            100                 105                 110

Ile Tyr Phe Cys Met Ile Val Gly Ser Pro Glu Leu Thr Phe Gly Lys
        115                 120                 125

Gly Thr Gln Leu Ser Val Val Asp Phe Leu Pro Thr Thr Ala Gln Pro
130                 135                 140

Thr Lys Lys Ser Thr Leu Lys Lys Arg Val Cys Arg Leu Pro Arg Pro
145                 150                 155                 160

Glu Thr Gln Lys Gly Pro Leu Cys Ser Pro Ile Thr Leu Gly Leu Leu
                165                 170                 175

Val Ala Gly Val Leu Val Leu Leu Val Ser Leu Gly Val Ala Ile His
            180                 185                 190

Leu Cys Cys Arg Arg Arg Arg Ala Arg Leu Arg Phe Met Lys Gln Lys
        195                 200                 205

Phe Asn Ile Val Cys Leu Lys Ile Ser Gly Phe Thr Thr Cys Cys Cys
210                 215                 220

Phe Gln Ile Leu Gln Met Ser Arg Glu Tyr Gly Phe Gly Val Leu Leu
225                 230                 235                 240

Gln Lys Asp Ile Gly Gln
                245
```

<210> SEQ ID NO 50
<211> LENGTH: 198
<212> TYPE: PRT
<213> ORGANISM: Homo sapiens

<400> SEQUENCE: 50

```
Met Arg Pro Arg Leu Trp Leu Leu Leu Ala Ala Gln Leu Thr Val Leu
1               5                   10                  15

His Gly Asn Ser Val Leu Gln Gln Thr Pro Ala Tyr Ile Lys Val Gln
            20                  25                  30

Thr Asn Lys Met Val Met Leu Ser Cys Glu Ala Lys Ile Ser Leu Ser
        35                  40                  45

Asn Met Arg Ile Tyr Trp Leu Arg Gln Arg Gln Ala Pro Ser Ser Asp
50                  55                  60

Ser His His Glu Phe Leu Ala Leu Trp Asp Ser Ala Lys Gly Thr Ile
65                  70                  75                  80

His Gly Glu Glu Val Glu Gln Glu Lys Ile Ala Val Phe Arg Asp Ala
                85                  90                  95

Ser Arg Phe Ile Leu Asn Leu Thr Ser Val Lys Pro Glu Asp Ser Gly
            100                 105                 110
```

```
Ile Tyr Phe Cys Met Ile Val Gly Ser Pro Glu Leu Thr Phe Gly Lys
            115                 120                 125

Gly Thr Gln Leu Ser Val Val Asp Phe Leu Pro Thr Thr Ala Gln Pro
    130                 135                 140

Thr Lys Lys Ser Thr Leu Lys Lys Arg Val Cys Arg Leu Pro Arg Pro
145                 150                 155                 160

Glu Thr Gln Lys Gly Leu Lys Gly Lys Val Tyr Gln Glu Pro Leu Ser
                165                 170                 175

Pro Asn Ala Cys Met Asp Thr Thr Ala Ile Leu Gln Pro His Arg Ser
            180                 185                 190

Cys Leu Thr His Gly Ser
        195

<210> SEQ ID NO 51
<211> LENGTH: 243
<212> TYPE: PRT
<213> ORGANISM: Homo sapiens

<400> SEQUENCE: 51

Met Arg Pro Arg Leu Trp Leu Leu Leu Ala Ala Gln Leu Thr Val Leu
1               5                   10                  15

His Gly Asn Ser Val Leu Gln Gln Thr Pro Ala Tyr Ile Lys Val Gln
                20                  25                  30

Thr Asn Lys Met Val Met Leu Ser Cys Glu Ala Lys Ile Ser Leu Ser
            35                  40                  45

Asn Met Arg Ile Tyr Trp Leu Arg Gln Arg Gln Ala Pro Ser Ser Asp
50                  55                  60

Ser His His Glu Phe Leu Ala Leu Trp Asp Ser Ala Lys Gly Thr Ile
65                  70                  75                  80

His Gly Glu Glu Val Glu Gln Glu Lys Ile Ala Val Phe Arg Asp Ala
                85                  90                  95

Ser Arg Phe Ile Leu Asn Leu Thr Ser Val Lys Pro Glu Asp Ser Gly
            100                 105                 110

Ile Tyr Phe Cys Met Ile Val Gly Ser Pro Glu Leu Thr Phe Gly Lys
            115                 120                 125

Gly Thr Gln Leu Ser Val Val Asp Phe Leu Pro Thr Thr Ala Gln Pro
    130                 135                 140

Thr Lys Lys Ser Thr Leu Lys Lys Arg Val Cys Arg Leu Pro Arg Pro
145                 150                 155                 160

Glu Thr Gln Lys Gly Pro Leu Cys Ser Pro Ile Thr Leu Gly Leu Leu
                165                 170                 175

Val Ala Gly Val Leu Val Leu Leu Val Ser Leu Gly Val Ala Ile His
            180                 185                 190

Leu Cys Cys Arg Arg Arg Ala Arg Leu Arg Phe Met Lys Gln Pro
        195                 200                 205

Gln Gly Glu Gly Ile Ser Gly Thr Phe Val Pro Gln Cys Leu His Gly
            210                 215                 220

Tyr Tyr Ser Asn Thr Thr Thr Ser Gln Lys Leu Leu Asn Pro Trp Ile
225                 230                 235                 240

Leu Lys Thr

<210> SEQ ID NO 52
<211> LENGTH: 213
<212> TYPE: PRT
<213> ORGANISM: Homo sapiens
```

```
<400> SEQUENCE: 52

Met Arg Pro Arg Leu Trp Leu Leu Leu Ala Ala Gln Leu Thr Val Leu
1               5                   10                  15

His Gly Asn Ser Val Leu Gln Gln Thr Pro Ala Tyr Ile Lys Val Gln
                20                  25                  30

Thr Asn Lys Met Val Met Leu Ser Cys Glu Ala Lys Ile Ser Leu Ser
            35                  40                  45

Asn Met Arg Ile Tyr Trp Leu Arg Gln Arg Gln Ala Pro Ser Ser Asp
    50                  55                  60

Ser His His Glu Phe Leu Ala Leu Trp Asp Ser Ala Lys Gly Thr Ile
65                  70                  75                  80

His Gly Glu Glu Val Glu Gln Glu Lys Ile Ala Val Phe Arg Asp Ala
                85                  90                  95

Ser Arg Phe Ile Leu Asn Leu Thr Ser Val Lys Pro Glu Asp Ser Gly
                100                 105                 110

Ile Tyr Phe Cys Met Ile Val Gly Ser Pro Glu Leu Thr Phe Gly Lys
            115                 120                 125

Gly Thr Gln Leu Ser Val Val Asp Phe Leu Pro Thr Thr Ala Gln Pro
130                 135                 140

Thr Lys Lys Ser Thr Leu Lys Lys Arg Val Cys Arg Leu Pro Arg Pro
145                 150                 155                 160

Glu Thr Gln Lys Gly Arg Arg Arg Ala Arg Leu Arg Phe Met Lys
                165                 170                 175

Gln Pro Gln Gly Glu Gly Ile Ser Gly Thr Phe Val Pro Gln Cys Leu
            180                 185                 190

His Gly Tyr Tyr Ser Asn Thr Thr Thr Ser Gln Lys Leu Leu Asn Pro
                195                 200                 205

Trp Ile Leu Lys Thr
            210

<210> SEQ ID NO 53
<211> LENGTH: 221
<212> TYPE: PRT
<213> ORGANISM: Homo sapiens

<400> SEQUENCE: 53

Met Arg Pro Arg Leu Trp Leu Leu Leu Ala Ala Gln Leu Thr Val Leu
1               5                   10                  15

His Gly Asn Ser Val Leu Gln Gln Thr Pro Ala Tyr Ile Lys Val Gln
                20                  25                  30

Thr Asn Lys Met Val Met Leu Ser Cys Glu Ala Lys Ile Ser Leu Ser
            35                  40                  45

Asn Met Arg Ile Tyr Trp Leu Arg Gln Arg Gln Ala Pro Ser Ser Asp
    50                  55                  60

Ser His His Glu Phe Leu Ala Leu Trp Asp Ser Ala Lys Gly Thr Ile
65                  70                  75                  80

His Gly Glu Glu Val Glu Gln Glu Lys Ile Ala Val Phe Arg Asp Ala
                85                  90                  95

Ser Arg Phe Ile Leu Asn Leu Thr Ser Val Lys Pro Glu Asp Ser Gly
                100                 105                 110

Ile Tyr Phe Cys Met Ile Val Gly Ser Pro Glu Leu Thr Phe Gly Lys
            115                 120                 125

Gly Thr Gln Leu Ser Val Val Asp Phe Leu Pro Thr Thr Ala Gln Pro
130                 135                 140
```

```
Thr Lys Lys Ser Thr Leu Lys Lys Arg Val Cys Arg Leu Pro Arg Pro
145                 150                 155                 160

Glu Thr Gln Lys Gly Pro Leu Cys Ser Pro Ile Thr Leu Gly Leu Leu
            165                 170                 175

Val Ala Gly Val Leu Val Leu Leu Val Ser Leu Gly Val Ala Ile His
        180                 185                 190

Leu Cys Cys Arg Arg Arg Arg Ala Arg Leu Arg Phe Met Lys Gln Leu
    195                 200                 205

Arg Leu His Pro Leu Glu Lys Cys Ser Arg Met Asp Tyr
210                 215                 220

<210> SEQ ID NO 54
<211> LENGTH: 210
<212> TYPE: PRT
<213> ORGANISM: Homo sapiens

<400> SEQUENCE: 54

Met Arg Pro Arg Leu Trp Leu Leu Leu Ala Ala Gln Leu Thr Val Leu
1               5                   10                  15

His Gly Asn Ser Val Leu Gln Gln Thr Pro Ala Tyr Ile Lys Val Gln
            20                  25                  30

Thr Asn Lys Met Val Met Leu Ser Cys Glu Ala Lys Ile Ser Leu Ser
        35                  40                  45

Asn Met Arg Ile Tyr Trp Leu Arg Gln Arg Gln Ala Pro Ser Ser Asp
    50                  55                  60

Ser His His Glu Phe Leu Ala Leu Trp Asp Ser Ala Lys Gly Thr Ile
65                  70                  75                  80

His Gly Glu Glu Val Glu Gln Glu Lys Ile Ala Val Phe Arg Asp Ala
                85                  90                  95

Ser Arg Phe Ile Leu Asn Leu Thr Ser Val Lys Pro Glu Asp Ser Gly
            100                 105                 110

Ile Tyr Phe Cys Met Ile Val Gly Ser Pro Glu Leu Thr Phe Gly Lys
        115                 120                 125

Gly Thr Gln Leu Ser Val Val Asp Phe Leu Pro Thr Thr Ala Gln Pro
130                 135                 140

Thr Lys Lys Ser Thr Leu Lys Lys Arg Val Cys Arg Leu Pro Arg Pro
145                 150                 155                 160

Glu Thr Gln Lys Gly Pro Leu Cys Ser Pro Ile Thr Leu Gly Leu Leu
            165                 170                 175

Val Ala Gly Val Leu Val Leu Leu Val Ser Leu Gly Val Ala Ile His
        180                 185                 190

Leu Cys Cys Arg Arg Arg Arg Ala Arg Leu Arg Phe Met Lys Gln Phe
    195                 200                 205

Tyr Lys
210

<210> SEQ ID NO 55
<211> LENGTH: 163
<212> TYPE: PRT
<213> ORGANISM: Homo sapiens

<400> SEQUENCE: 55

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30
```

-continued

Tyr Leu Leu Asp Gly Ile Leu Phe Ile Tyr Gly Val Ile Leu Thr Ala
            35                  40                  45

Leu Phe Leu Arg Val Lys Phe Ser Arg Ser Ala Asp Ala Pro Ala Tyr
 50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Arg Arg Lys Asn Pro Gln Glu Gly Leu Tyr Asn Glu
            100                 105                 110

Leu Gln Lys Asp Lys Met Ala Glu Ala Tyr Ser Glu Ile Gly Met Lys
            115                 120                 125

Gly Glu Arg Arg Arg Gly Lys Gly His Asp Gly Leu Tyr Gln Gly Leu
            130                 135                 140

Ser Thr Ala Thr Lys Asp Thr Tyr Asp Ala Leu His Met Gln Ala Leu
145                 150                 155                 160

Pro Pro Arg

<210> SEQ ID NO 56
<211> LENGTH: 164
<212> TYPE: PRT
<213> ORGANISM: Homo sapiens

<400> SEQUENCE: 56

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
            35                  40                  45

Leu Phe Leu Arg Val Lys Phe Ser Arg Ser Ala Asp Ala Pro Ala Tyr
 50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
            115                 120                 125

Lys Gly Glu Arg Arg Arg Gly Lys Gly His Asp Gly Leu Tyr Gln Gly
            130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 57
<211> LENGTH: 123
<212> TYPE: PRT
<213> ORGANISM: Homo sapiens

<400> SEQUENCE: 57

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr

```
                20              25              30
Asp Asn Ala Val Asn Leu Ser Trp Lys His Leu Cys Pro Ser Pro Leu
            35              40              45

Phe Pro Gly Pro Ser Lys Pro Phe Trp Val Leu Val Val Gly Gly
        50              55              60

Val Leu Ala Cys Tyr Ser Leu Leu Val Thr Val Ala Phe Ile Ile Phe
65              70              75              80

Trp Val Arg Ser Lys Arg Ser Arg Leu Leu His Ser Asp Tyr Met Asn
                85              90              95

Met Thr Pro Arg Arg Pro Gly Pro Thr Arg Lys His Tyr Gln Pro Tyr
            100             105             110

Ala Pro Pro Arg Asp Phe Ala Ala Tyr Arg Ser
            115             120

<210> SEQ ID NO 58
<211> LENGTH: 101
<212> TYPE: PRT
<213> ORGANISM: Homo sapiens

<400> SEQUENCE: 58

Met Leu Arg Leu Leu Ala Leu Asn Leu Phe Pro Ser Ile Gln Val
1               5               10              15

Thr Gly Lys His Leu Cys Pro Ser Pro Leu Phe Pro Gly Pro Ser Lys
            20              25              30

Pro Phe Trp Val Leu Val Val Gly Gly Val Leu Ala Cys Tyr Ser
            35              40              45

Leu Leu Val Thr Val Ala Phe Ile Ile Phe Trp Val Arg Ser Lys Arg
    50              55              60

Ser Arg Leu Leu His Ser Asp Tyr Met Asn Met Thr Pro Arg Arg Pro
65              70              75              80

Gly Pro Thr Arg Lys His Tyr Gln Pro Tyr Ala Pro Pro Arg Asp Phe
                85              90              95

Ala Ala Tyr Arg Ser
            100

<210> SEQ ID NO 59
<211> LENGTH: 220
<212> TYPE: PRT
<213> ORGANISM: Homo sapiens

<400> SEQUENCE: 59

Met Leu Arg Leu Leu Ala Leu Asn Leu Phe Pro Ser Ile Gln Val
1               5               10              15

Thr Gly Asn Lys Ile Leu Val Lys Gln Ser Pro Met Leu Val Ala Tyr
            20              25              30

Asp Asn Ala Val Asn Leu Ser Cys Lys Tyr Ser Tyr Asn Leu Phe Ser
            35              40              45

Arg Glu Phe Arg Ala Ser Leu His Lys Gly Leu Asp Ser Ala Val Glu
        50              55              60

Val Cys Val Val Tyr Gly Asn Tyr Ser Gln Gln Leu Gln Val Tyr Ser
65              70              75              80

Lys Thr Gly Phe Asn Cys Asp Gly Lys Leu Gly Asn Glu Ser Val Thr
                85              90              95

Phe Tyr Leu Gln Asn Leu Tyr Val Asn Gln Thr Asp Ile Tyr Phe Cys
            100             105             110

Lys Ile Glu Val Met Tyr Pro Pro Pro Tyr Leu Asp Asn Glu Lys Ser
```

```
                  115                 120                 125
Asn Gly Thr Ile Ile His Val Lys Gly Lys His Leu Cys Pro Ser Pro
        130                 135                 140

Leu Phe Pro Gly Pro Ser Lys Pro Phe Trp Val Leu Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
                180                 185                 190

Asn Met Thr Pro Arg Arg Pro Gly Pro Thr Arg Lys His Tyr Gln Pro
            195                 200                 205

Tyr Ala Pro Pro Arg Asp Phe Ala Ala Tyr Arg Ser
        210                 215                 220

<210> SEQ ID NO 60
<211> LENGTH: 277
<212> TYPE: PRT
<213> ORGANISM: Homo sapiens

<400> SEQUENCE: 60

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
                20                  25                  30

Gly Asp Thr Tyr Pro Ser Asn Asp Arg Cys Cys His Glu Cys Arg Pro
            35                  40                  45

Gly Asn Gly Met Val Ser Arg Cys Ser Arg Ser Gln Asn Thr Val Cys
        50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
                100                 105                 110

Thr Gln Pro Leu Asp Ser Tyr Lys Pro Gly Val Asp Cys Ala Pro Cys
            115                 120                 125

Pro Pro Gly His Phe Ser Pro Gly Asp Asn Gln Ala Cys Lys Pro Trp
        130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270
```

```
Thr Leu Ala Lys Ile
    275

<210> SEQ ID NO 61
<211> LENGTH: 174
<212> TYPE: PRT
<213> ORGANISM: Homo sapiens

<400> SEQUENCE: 61

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Ala Lys Glu Lys Pro Ser Tyr
145                 150                 155                 160

Asn Arg Gly Leu Cys Glu Asn Ala Pro Asn Arg Ala Arg Met
            165                 170

<210> SEQ ID NO 62
<211> LENGTH: 223
<212> TYPE: PRT
<213> ORGANISM: Homo sapiens

<400> SEQUENCE: 62

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140
```

-continued

```
Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
                180                 185                 190

Arg Ser Pro Leu Thr Thr Gly Val Tyr Val Lys Met Pro Pro Thr Glu
                195                 200                 205

Pro Glu Cys Glu Lys Gln Phe Gln Pro Tyr Phe Ile Pro Ile Asn
    210                 215                 220
```

<210> SEQ ID NO 63
<211> LENGTH: 288
<212> TYPE: PRT
<213> ORGANISM: Homo sapiens

<400> SEQUENCE: 63

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
                35                  40                  45

Asn Ala Thr Phe Thr Cys Ser Phe Ser Asn Thr Ser Glu Ser Phe Val
50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
                100                 105                 110

Ala Arg Arg Asn Asp Ser Gly Thr Tyr Leu Cys Gly Ala Ile Ser Leu
                115                 120                 125

Ala Pro Lys Ala Gln Ile Lys Glu Ser Leu Arg Ala Glu Leu Arg Val
                130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
                180                 185                 190

Ser Arg Ala Ala Arg Gly Thr Ile Gly Ala Arg Arg Thr Gly Gln Pro
                195                 200                 205

Leu Lys Glu Asp Pro Ser Ala Val Pro Val Phe Ser Val Asp Tyr Gly
                210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
                260                 265                 270

Ser Ala Gln Pro Leu Arg Pro Glu Asp Gly His Cys Ser Trp Pro Leu
                275                 280                 285
```

<210> SEQ ID NO 64

<211> LENGTH: 241
<212> TYPE: PRT
<213> ORGANISM: Homo sapiens

<400> SEQUENCE: 64

Met Ala Gln His Gly Ala Met Gly Ala Phe Arg Ala Leu Cys Gly Leu
1               5                   10                  15

Ala Leu Leu Cys Ala Leu Ser Leu Gly Gln Arg Pro Thr Gly Gly Pro
            20                  25                  30

Gly Cys Gly Pro Gly Arg Leu Leu Gly Thr Gly Thr Asp Ala Arg
        35                  40                  45

Cys Cys Arg Val His Thr Thr Arg Cys Cys Arg Asp Tyr Pro Gly Glu
50                  55                  60

Glu Cys Cys Ser Glu Trp Asp Cys Met Cys Val Gln Pro Glu Phe His
65                  70                  75                  80

Cys Gly Asp Pro Cys Cys Thr Thr Cys Arg His His Pro Cys Pro Pro
                85                  90                  95

Gly Gln Gly Val Gln Ser Gln Gly Lys Phe Ser Phe Gly Phe Gln Cys
            100                 105                 110

Ile Asp Cys Ala Ser Gly Thr Phe Ser Gly Gly His Glu Gly His Cys
        115                 120                 125

Lys Pro Trp Thr Asp Cys Thr Gln Phe Gly Phe Leu Thr Val Phe Pro
130                 135                 140

Gly Asn Lys Thr His Asn Ala Val Cys Val Pro Gly Ser Pro Pro Ala
145                 150                 155                 160

Glu Pro Leu Gly Trp Leu Thr Val Val Leu Leu Ala Val Ala Ala Cys
                165                 170                 175

Val Leu Leu Leu Thr Ser Ala Gln Leu Gly Leu His Ile Trp Gln Leu
            180                 185                 190

Arg Ser Gln Cys Met Trp Pro Arg Glu Thr Gln Leu Leu Leu Glu Val
        195                 200                 205

Pro Pro Ser Thr Glu Asp Ala Arg Ser Cys Gln Phe Pro Glu Glu Glu
    210                 215                 220

Arg Gly Glu Arg Ser Ala Glu Glu Lys Gly Arg Leu Gly Asp Leu Trp
225                 230                 235                 240

Val

<210> SEQ ID NO 65
<211> LENGTH: 255
<212> TYPE: PRT
<213> ORGANISM: Homo sapiens

<400> SEQUENCE: 65

Met Ala Gln His Gly Ala Met Gly Ala Phe Arg Ala Leu Cys Gly Leu
1               5                   10                  15

Ala Leu Leu Cys Ala Leu Ser Leu Gly Gln Arg Pro Thr Gly Gly Pro
            20                  25                  30

Gly Cys Gly Pro Gly Arg Leu Leu Gly Thr Gly Thr Asp Ala Arg
        35                  40                  45

Cys Cys Arg Val His Thr Thr Arg Cys Cys Arg Asp Tyr Pro Gly Glu
50                  55                  60

Glu Cys Cys Ser Glu Trp Asp Cys Met Cys Val Gln Pro Glu Phe His
65                  70                  75                  80

Cys Gly Asp Pro Cys Cys Thr Thr Cys Arg His His Pro Cys Pro Pro
                85                  90                  95

```
Gly Gln Gly Val Gln Ser Gln Gly Lys Phe Ser Phe Gly Phe Gln Cys
            100                 105                 110

Ile Asp Cys Ala Ser Gly Thr Phe Ser Gly Gly His Glu Gly His Cys
            115                 120                 125

Lys Pro Trp Thr Asp Cys Cys Trp Arg Cys Arg Arg Arg Pro Lys Thr
            130                 135                 140

Pro Glu Ala Ala Ser Ser Pro Arg Lys Ser Gly Ala Ser Asp Arg Gln
145                 150                 155                 160

Arg Arg Arg Gly Gly Trp Glu Thr Cys Gly Cys Glu Pro Gly Arg Pro
                165                 170                 175

Pro Gly Pro Pro Thr Ala Ala Ser Pro Ser Pro Gly Ala Pro Gln Ala
            180                 185                 190

Ala Gly Ala Leu Arg Ser Ala Leu Gly Arg Ala Leu Leu Pro Trp Gln
            195                 200                 205

Gln Lys Trp Val Gln Glu Gly Gly Ser Asp Gln Arg Pro Gly Pro Cys
            210                 215                 220

Ser Ser Ala Ala Ala Ala Gly Pro Cys Arg Arg Glu Arg Glu Thr Gln
225                 230                 235                 240

Ser Trp Pro Pro Ser Ser Leu Ala Gly Pro Asp Gly Val Gly Ser
                245                 250                 255

<210> SEQ ID NO 66
<211> LENGTH: 234
<212> TYPE: PRT
<213> ORGANISM: Homo sapiens

<400> SEQUENCE: 66

Met Ala Gln His Gly Ala Met Gly Ala Phe Arg Ala Leu Cys Gly Leu
1               5                   10                  15

Ala Leu Leu Cys Ala Leu Ser Leu Gly Gln Arg Pro Thr Gly Gly Pro
            20                  25                  30

Gly Cys Gly Pro Gly Arg Leu Leu Leu Gly Thr Gly Thr Asp Ala Arg
            35                  40                  45

Cys Cys Arg Val His Thr Thr Arg Cys Cys Arg Asp Tyr Pro Gly Glu
        50                  55                  60

Glu Cys Cys Ser Glu Trp Asp Cys Met Cys Val Gln Pro Glu Phe His
65                  70                  75                  80

Cys Gly Asp Pro Cys Cys Thr Thr Cys Arg His His Pro Cys Pro Pro
                85                  90                  95

Gly Gln Gly Val Gln Ser Gln Gly Lys Phe Ser Phe Gly Phe Gln Cys
            100                 105                 110

Ile Asp Cys Ala Ser Gly Thr Phe Ser Gly Gly His Glu Gly His Cys
            115                 120                 125

Lys Pro Trp Thr Asp Cys Thr Gln Phe Gly Phe Leu Thr Val Phe Pro
            130                 135                 140

Gly Asn Lys Thr His Asn Ala Val Cys Val Pro Gly Ser Pro Pro Ala
145                 150                 155                 160

Glu Pro Leu Gly Trp Leu Thr Val Val Leu Leu Ala Val Ala Ala Cys
                165                 170                 175

Val Leu Leu Leu Thr Ser Ala Gln Leu Gly Leu His Ile Trp Gln Leu
            180                 185                 190

Arg Lys Thr Gln Leu Leu Leu Glu Val Pro Pro Ser Thr Glu Asp Ala
            195                 200                 205

Arg Ser Cys Gln Phe Pro Glu Glu Glu Arg Gly Glu Arg Ser Ala Glu
            210                 215                 220
```

Glu Lys Gly Arg Leu Gly Asp Leu Trp Val
225                 230

<210> SEQ ID NO 67
<211> LENGTH: 57
<212> TYPE: PRT
<213> ORGANISM: Homo sapiens

<400> SEQUENCE: 67

Gln Leu Gly Leu His Ile Trp Gln Leu Arg Ser Gln Cys Met Trp Pro
1               5                   10                  15

Arg Glu Thr Gln Leu Leu Leu Glu Val Pro Pro Ser Thr Glu Asp Ala
            20                  25                  30

Arg Ser Cys Gln Phe Pro Glu Glu Glu Arg Gly Glu Arg Ser Ala Glu
        35                  40                  45

Glu Lys Gly Arg Leu Gly Asp Leu Trp
    50                  55

<210> SEQ ID NO 68
<211> LENGTH: 118
<212> TYPE: PRT
<213> ORGANISM: Artificial Sequence
<220> FEATURE:
<223> OTHER INFORMATION: portion of antibody

<400> SEQUENCE: 68

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Lys Phe Ser Arg Tyr
            20                  25                  30

Ala Met Ser Trp Val Arg Gln Thr Pro Glu Lys Arg Leu Glu Trp Val
        35                  40                  45

Ala Thr Ile Ser Ser Gly Gly Ser Tyr Ile Tyr Tyr Pro Asp Ser Val
    50                  55                  60

Lys Gly Arg Phe Thr Ile Ser Arg Asp Asn Val Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Arg Asp Tyr Asp Leu Asp Tyr Phe Asp Ser Trp Gly Gln Gly
            100                 105                 110

Thr Thr Leu Thr Val Ser
        115

<210> SEQ ID NO 69
<211> LENGTH: 109
<212> TYPE: PRT
<213> ORGANISM: Artificial Sequence
<220> FEATURE:
<223> OTHER INFORMATION: portion of antibody

<400> SEQUENCE: 69

Asp Ile Lys Met Thr Gln Ser Pro Ser Ser Met Tyr Ala Ser Leu Gly
1               5                   10                  15

Glu Arg Val Thr Ile Thr Cys Lys Ala Ser Arg Asp Ile Arg Ser Tyr
            20                  25                  30

Leu Thr Trp Tyr Gln Gln Lys Pro Trp Lys Ser Pro Lys Thr Leu Ile
        35                  40                  45

Tyr Tyr Ala Thr Ser Leu Ala Asp Gly Val Pro Ser Arg Phe Ser Gly
    50                  55                  60

```
Ser Gly Ser Gly Gln Asp Tyr Ser Leu Thr Ile Ser Ser Leu Glu Ser
 65                  70                  75                  80

Asp Asp Thr Ala Thr Tyr Tyr Cys Leu Gln His Gly Glu Ser Pro Phe
                 85                  90                  95

Thr Phe Gly Ser Gly Thr Lys Leu Glu Ile Lys Arg Ala
            100                 105

<210> SEQ ID NO 70
<211> LENGTH: 22
<212> TYPE: PRT
<213> ORGANISM: Artificial Sequence
<220> FEATURE:
<223> OTHER INFORMATION: portion of antibody

<400> SEQUENCE: 70

Met Leu Leu Leu Val Thr Ser Leu Leu Cys Glu Leu Pro His Pro
 1               5                  10                  15

Ala Phe Leu Leu Ile Pro
            20

<210> SEQ ID NO 71
<211> LENGTH: 24
<212> TYPE: PRT
<213> ORGANISM: Homo sapiens

<400> SEQUENCE: 71

Leu Glu Gly Gly Gly Glu Gly Arg Gly Ser Leu Leu Thr Cys Gly Asp
 1               5                  10                  15

Val Glu Glu Asn Pro Gly Pro Arg
            20

<210> SEQ ID NO 72

<400> SEQUENCE: 72

000

<210> SEQ ID NO 73
<211> LENGTH: 323
<212> TYPE: PRT
<213> ORGANISM: Homo sapiens

<400> SEQUENCE: 73

Met Pro Pro Pro Arg Leu Leu Phe Phe Leu Leu Phe Leu Thr Pro Met
 1               5                  10                  15

Glu Val Arg Pro Glu Glu Pro Leu Val Val Lys Val Glu Glu Gly Asp
                20                  25                  30

Asn Ala Val Leu Gln Cys Leu Lys Gly Thr Ser Asp Gly Pro Thr Gln
             35                  40                  45

Gln Leu Thr Trp Ser Arg Glu Ser Pro Leu Lys Pro Phe Leu Lys Leu
         50                  55                  60

Ser Leu Gly Leu Pro Gly Leu Gly Ile His Met Arg Pro Leu Ala Ile
 65                  70                  75                  80

Trp Leu Phe Ile Phe Asn Val Ser Gln Gln Met Gly Gly Phe Tyr Leu
                 85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125
```

```
Leu Gly Gly Leu Gly Cys Gly Leu Lys Asn Arg Ser Ser Glu Gly Pro
    130             135                 140

Ser Ser Pro Ser Gly Lys Leu Met Ser Pro Lys Leu Tyr Val Trp Ala
145             150                 155                 160

Lys Asp Arg Pro Glu Ile Trp Glu Gly Glu Pro Pro Cys Val Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225             230                 235                 240

Val Met Glu Thr Gly Leu Leu Pro Arg Ala Thr Ala Gln Asp Ala
                245                 250                 255

Gly Lys Tyr Tyr Cys His Arg Gly Asn Leu Thr Met Ser Phe His Leu
                260                 265                 270

Glu Ile Thr Ala Arg Pro Val Leu Trp His Trp Leu Leu Arg Thr Gly
                275                 280                 285

Gly Trp Lys Val Ser Ala Val Thr Leu Ala Tyr Leu Ile Phe Cys Leu
        290                 295                 300

Cys Ser Leu Val Gly Ile Leu His Leu Gln Arg Ala Leu Val Leu Arg
305                 310                 315                 320

Arg Lys Arg

<210> SEQ ID NO 74

<400> SEQUENCE: 74

000

<210> SEQ ID NO 75
<211> LENGTH: 68
<212> TYPE: PRT
<213> ORGANISM: Homo sapiens

<400> SEQUENCE: 75

Ile Gln Met Thr Gln Ser Pro Ser Ser Leu Ser Ala Ser Val Gly Asp
1               5                   10                  15

Arg Val Thr Ile Thr Cys Lys Ala Ser Arg Asp Ile Arg Ser Tyr Leu
                20                  25                  30

Thr Trp Tyr Gln Gln Lys Pro Gly Lys Ala Pro Lys Thr Leu Ile Tyr
            35                  40                  45

Tyr Ala Thr Ser Leu Ala Asp Gly Val Pro Ser Arg Phe Ser Gly Ser
        50                  55                  60

Gly Ser Gly Gln
65

<210> SEQ ID NO 76
<211> LENGTH: 32
<212> TYPE: PRT
<213> ORGANISM: Artificial Sequence
<220> FEATURE:
<223> OTHER INFORMATION: portion of antibody

<400> SEQUENCE: 76

Asp Ile Gln Met Thr Gln Ser Pro Ser Ser Leu Ser Ala Ser Val Gly
```

```
                1               5                  10                 15
Asp Arg Val Thr Ile Thr Cys Lys Ala Ser Arg Asp Ile Arg Ser Tyr
                20                 25                 30
```

<210> SEQ ID NO 77
<211> LENGTH: 65
<212> TYPE: PRT
<213> ORGANISM: Artificial Sequence
<220> FEATURE:
<223> OTHER INFORMATION: portion of antibody

<400> SEQUENCE: 77

```
Leu Thr Trp Tyr Gln Gln Lys Pro Gly Lys Ala Pro Lys Thr Leu Ile
1               5                  10                 15

Tyr Tyr Ala Thr Ser Leu Ala Asp Gly Val Pro Ser Arg Phe Ser Gly
                20                 25                 30

Ser Gly Ser Gly Gln Asp Tyr Ser Leu Thr Ile Ser Ser Leu Glu Ser
                35                 40                 45

Asp Asp Thr Ala Thr Tyr Tyr Cys Leu Gln His Gly Glu Ser Pro Phe
        50                 55                 60

Thr
65
```

<210> SEQ ID NO 78
<211> LENGTH: 12
<212> TYPE: PRT
<213> ORGANISM: Artificial Sequence
<220> FEATURE:
<223> OTHER INFORMATION: portion of antibody

<400> SEQUENCE: 78

```
Phe Gly Ser Gly Thr Lys Leu Glu Ile Lys Arg Ala
1               5                  10
```

<210> SEQ ID NO 79
<211> LENGTH: 35
<212> TYPE: PRT
<213> ORGANISM: Artificial Sequence
<220> FEATURE:
<223> OTHER INFORMATION: portion of antibody

<400> SEQUENCE: 79

```
Glu Val Gln Leu Val Glu Ser Gly Gly Gly Leu Val Lys Pro Gly Gly
1               5                  10                 15

Ser Leu Lys Leu Ser Cys Ala Ala Ser Gly Phe Lys Phe Ser Arg Tyr
                20                 25                 30

Ala Met Ser
        35
```

<210> SEQ ID NO 80
<211> LENGTH: 20
<212> TYPE: PRT
<213> ORGANISM: Artificial Sequence
<220> FEATURE:
<223> OTHER INFORMATION: portion of antibody

<400> SEQUENCE: 80

```
Trp Val Arg Gln Ala Pro Gly Lys Arg Leu Glu Trp Val Ala Thr Ile
1               5                  10                 15

Ser Ser Gly Gly
        20
```

-continued

<210> SEQ ID NO 81
<211> LENGTH: 53
<212> TYPE: PRT
<213> ORGANISM: Artificial Sequence
<220> FEATURE:
<223> OTHER INFORMATION: portion of antibody

<400> SEQUENCE: 81

Ser Tyr Ile Tyr Tyr Pro Asp Ser Val Lys Gly Arg Phe Thr Ile Ser
1               5                   10                  15

Arg Asp Asn Val Lys Asn Thr Leu Tyr Leu Gln Met Ser Ser Leu Arg
            20                  25                  30

Ser Glu Asp Thr Ala Met Tyr Tyr Cys Ala Arg Arg Asp Tyr Asp Leu
        35                  40                  45

Asp Tyr Phe Asp Ser
    50

<210> SEQ ID NO 82
<211> LENGTH: 11
<212> TYPE: PRT
<213> ORGANISM: Artificial Sequence
<220> FEATURE:
<223> OTHER INFORMATION: portion of antibody

<400> SEQUENCE: 82

Trp Gly Gln Gly Thr Leu Val Thr Val Ser Ser
1               5                   10

<210> SEQ ID NO 83
<211> LENGTH: 653
<212> TYPE: PRT
<213> ORGANISM: Artificial Sequence
<220> FEATURE:
<223> OTHER INFORMATION: chimeric antigen receptor

<400> SEQUENCE: 83

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Lys Phe Ser Arg Tyr
            20                  25                  30

Ala Met Ser Trp Val Arg Gln Ala Pro Gly Lys Arg Leu Glu Trp Val
        35                  40                  45

Ala Thr Ile Ser Ser Gly Gly Ser Tyr Ile Tyr Tyr Pro Asp Ser Val
    50                  55                  60

Lys Gly Arg Phe Thr Ile Ser Arg Asp Asn Val Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Arg Asp Tyr Asp Leu Asp Tyr Phe Asp Ser Trp Gly Gln Gly
            100                 105                 110

Thr Leu Val Thr Val Ser Ser Gly Ser Thr Ser Gly Gly Gly Ser Gly
        115                 120                 125

Gly Gly Ser Gly Gly Gly Ser Ser Asp Ile Gln Met Thr Gln Ser
    130                 135                 140

Pro Ser Ser Leu Ser Ala Ser Val Gly Asp Arg Val Thr Ile Thr Cys
145                 150                 155                 160

Lys Ala Ser Arg Asp Ile Arg Ser Tyr Leu Thr Trp Tyr Gln Gln Lys
                165                 170                 175

Pro Gly Lys Ala Pro Lys Thr Leu Ile Tyr Tyr Ala Thr Ser Leu Ala
            180                 185                 190

-continued

Asp Gly Val Pro Ser Arg Phe Ser Gly Ser Gly Gln Asp Tyr
        195                 200                 205

Ser Leu Thr Ile Ser Ser Leu Glu Ser Asp Asp Thr Ala Thr Tyr Tyr
    210                 215                 220

Cys Leu Gln His Gly Glu Ser Pro Phe Thr Phe Gly Ser Gly Thr Lys
225                 230                 235                 240

Leu Glu Ile Lys Arg Ala Glu Ser Lys Tyr Gly Pro Pro Cys Pro Pro
            245                 250                 255

Cys Pro Ala Pro Glu Phe Glu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser Gln Glu Asp Pro Glu Val Gln Phe Asn
290                 295                 300

Trp Tyr Val Asp Gly Val Glu Val His Asn Ala Lys Thr Lys Pro Arg
305                 310                 315                 320

Glu Glu Gln Phe Gln Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Gly Leu Pro Ser Ser Ile Glu Lys Thr Ile Ser Lys Ala Lys
        355                 360                 365

Gly Gln Pro Arg Glu Pro Gln Val Tyr Thr Leu Pro Pro Ser Gln Glu
    370                 375                 380

Glu Met Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
            405                 410                 415

Asn Asn Tyr Lys Thr Thr Pro Pro Val Leu Asp Ser Asp Gly Ser Phe
        420                 425                 430

Phe Leu Tyr Ser Arg Leu Thr Val Asp Lys Ser Arg Trp Gln Glu Gly
    435                 440                 445

Asn Val Phe Ser Cys Ser Val Met His Glu Ala Leu His Asn His Tyr
450                 455                 460

Thr Gln Lys Ser Leu Ser Leu Ser Leu Gly Lys Met Ala Leu Ile Val
465                 470                 475                 480

Leu Gly Gly Val Ala Gly Leu Leu Phe Ile Gly Leu Gly Ile Phe
            485                 490                 495

Phe Ala Val Ser Leu Ser Lys Met Leu Lys Lys Arg Ser Pro Leu Thr
            500                 505                 510

Thr Gly Val Tyr Val Lys Met Pro Pro Thr Glu Pro Glu Cys Glu Lys
        515                 520                 525

Gln Phe Gln Pro Tyr Phe Ile Pro Ile Asn Gly Gly Arg Val Lys
    530                 535                 540

Phe Ser Arg Ser Ala Asp Ala Pro Ala Tyr Gln Gln Gly Gln Asn Gln
545                 550                 555                 560

Leu Tyr Asn Glu Leu Asn Leu Gly Arg Arg Glu Glu Tyr Asp Val Leu
            565                 570                 575

Asp Lys Arg Arg Gly Arg Asp Pro Glu Met Gly Gly Lys Pro Arg Arg
            580                 585                 590

Lys Asn Pro Gln Glu Gly Leu Tyr Asn Glu Leu Gln Lys Asp Lys Met
        595                 600                 605

```
Ala Glu Ala Tyr Ser Glu Ile Gly Met Lys Gly Glu Arg Arg Arg Gly
610                 615                 620

Lys Gly His Asp Gly Leu Tyr Gln Gly Leu Ser Thr Ala Thr Lys Asp
625                 630                 635                 640

Thr Tyr Asp Ala Leu His Met Gln Ala Leu Pro Pro Arg
                645                 650

<210> SEQ ID NO 84
<211> LENGTH: 675
<212> TYPE: PRT
<213> ORGANISM: Artificial Sequence
<220> FEATURE:
<223> OTHER INFORMATION: chimeric antigen receptor

<400> SEQUENCE: 84

Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
                20                  25                  30

Leu Val Lys Pro Gly Gly Ser Leu Lys Leu Ser Cys Ala Ala Ser Gly
            35                  40                  45

Phe Lys Phe Ser Arg Tyr Ala Met Ser Trp Val Arg Gln Ala Pro Gly
50                  55                  60

Lys Arg Leu Glu Trp Val Ala Thr Ile Ser Ser Gly Gly Ser Tyr Ile
65                  70                  75                  80

Tyr Tyr Pro Asp Ser Val Lys Gly Arg Phe Thr Ile Ser Arg Asp Asn
                85                  90                  95

Val Lys Asn Thr Leu Tyr Leu Gln Met Ser Ser Leu Arg Ser Glu Asp
            100                 105                 110

Thr Ala Met Tyr Tyr Cys Ala Arg Arg Asp Tyr Asp Leu Asp Tyr Phe
        115                 120                 125

Asp Ser Trp Gly Gln Gly Thr Leu Val Thr Val Ser Ser Gly Ser Thr
130                 135                 140

Ser Gly Gly Gly Ser Gly Gly Gly Ser Gly Gly Gly Ser Ser Asp
145                 150                 155                 160

Ile Gln Met Thr Gln Ser Pro Ser Ser Leu Ser Ala Ser Val Gly Asp
                165                 170                 175

Arg Val Thr Ile Thr Cys Lys Ala Ser Arg Asp Ile Arg Ser Tyr Leu
            180                 185                 190

Thr Trp Tyr Gln Gln Lys Pro Gly Lys Ala Pro Lys Thr Leu Ile Tyr
        195                 200                 205

Tyr Ala Thr Ser Leu Ala Asp Gly Val Pro Ser Arg Phe Ser Gly Ser
210                 215                 220

Gly Ser Gly Gln Asp Tyr Ser Leu Thr Ile Ser Ser Leu Glu Ser Asp
225                 230                 235                 240

Asp Thr Ala Thr Tyr Tyr Cys Leu Gln His Gly Glu Ser Pro Phe Thr
                245                 250                 255

Phe Gly Ser Gly Thr Lys Leu Glu Ile Lys Arg Ala Glu Ser Lys Tyr
            260                 265                 270

Gly Pro Pro Cys Pro Pro Cys Pro Ala Pro Glu Phe Glu Gly Gly Pro
        275                 280                 285

Ser Val Phe Leu Phe Pro Pro Lys Pro Lys Asp Thr Leu Met Ile Ser
290                 295                 300

Arg Thr Pro Glu Val Thr Cys Val Val Val Asp Val Ser Gln Glu Asp
305                 310                 315                 320
```

Pro Glu Val Gln Phe Asn Trp Tyr Val Asp Gly Val Glu Val His Asn
            325                 330                 335

Ala Lys Thr Lys Pro Arg Glu Glu Gln Phe Gln Ser Thr Tyr Arg Val
            340                 345                 350

Val Ser Val Leu Thr Val Leu His Gln Asp Trp Leu Asn Gly Lys Glu
            355                 360                 365

Tyr Lys Cys Lys Val Ser Asn Lys Gly Leu Pro Ser Ser Ile Glu Lys
            370                 375                 380

Thr Ile Ser Lys Ala Lys Gly Gln Pro Arg Glu Pro Gln Val Tyr Thr
385                 390                 395                 400

Leu Pro Pro Ser Gln Glu Glu Met Thr Lys Asn Gln Val Ser Leu Thr
            405                 410                 415

Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
            435                 440                 445

Asp Ser Asp Gly Ser Phe Phe Leu Tyr Ser Arg Leu Thr Val Asp Lys
            450                 455                 460

Ser Arg Trp Gln Glu Gly Asn Val Phe Ser Cys Ser Val Met His Glu
465                 470                 475                 480

Ala Leu His Asn His Tyr Thr Gln Lys Ser Leu Ser Leu Ser Leu Gly
            485                 490                 495

Lys Met Ala Leu Ile Val Leu Gly Gly Val Ala Gly Leu Leu Leu Phe
            500                 505                 510

Ile Gly Leu Gly Ile Phe Phe Ala Val Ser Leu Ser Lys Met Leu Lys
            515                 520                 525

Lys Arg Ser Pro Leu Thr Thr Gly Val Tyr Val Lys Met Pro Pro Thr
            530                 535                 540

Glu Pro Glu Cys Glu Lys Gln Phe Gln Pro Tyr Phe Ile Pro Ile Asn
545                 550                 555                 560

Gly Gly Gly Arg Val Lys Phe Ser Arg Ser Ala Asp Ala Pro Ala Tyr
            565                 570                 575

Gln Gln Gly Gln Asn Gln Leu Tyr Asn Glu Leu Asn Leu Gly Arg Arg
            580                 585                 590

Glu Glu Tyr Asp Val Leu Asp Lys Arg Arg Gly Arg Asp Pro Glu Met
            595                 600                 605

Gly Gly Lys Pro Arg Arg Lys Asn Pro Gln Glu Gly Leu Tyr Asn Glu
            610                 615                 620

Leu Gln Lys Asp Lys Met Ala Glu Ala Tyr Ser Glu Ile Gly Met Lys
625                 630                 635                 640

Gly Glu Arg Arg Arg Gly Lys Gly His Asp Gly Leu Tyr Gln Gly Leu
            645                 650                 655

Ser Thr Ala Thr Lys Asp Thr Tyr Asp Ala Leu His Met Gln Ala Leu
            660                 665                 670

Pro Pro Arg
        675

<210> SEQ ID NO 85
<211> LENGTH: 653
<212> TYPE: PRT
<213> ORGANISM: Artificial Sequence
<220> FEATURE:
<223> OTHER INFORMATION: chimeric antigen receptor

<400> SEQUENCE: 85

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Ile Arg Ser Tyr
            20                  25                  30

Leu Thr Trp Tyr Gln Gln Lys Pro Gly Lys Ala Pro Lys Thr Leu Ile
        35                  40                  45

Tyr Tyr Ala Thr Ser Leu Ala Asp Gly Val Pro Ser Arg Phe Ser Gly
50                  55                  60

Ser Gly Ser Gly Gln Asp Tyr Ser Leu Thr Ile Ser Ser Leu Glu Ser
65              70                  75                  80

Asp Asp Thr Ala Thr Tyr Tyr Cys Leu Gln His Gly Glu Ser Pro Phe
                85                  90                  95

Thr Phe Gly Ser Gly Thr Lys Leu Glu Ile Lys Arg Ala Gly Ser Thr
            100                 105                 110

Ser Gly Gly Gly Ser Gly Gly Gly Ser Gly Gly Gly Ser Ser Glu
            115                 120                 125

Val Gln Leu Val Glu Ser Gly Gly Leu Val Lys Pro Gly Gly Ser
        130                 135                 140

Leu Lys Leu Ser Cys Ala Ala Ser Gly Phe Lys Phe Ser Arg Tyr Ala
145                 150                 155                 160

Met Ser Trp Val Arg Gln Ala Pro Gly Lys Arg Leu Glu Trp Val Ala
            165                 170                 175

Thr Ile Ser Ser Gly Gly Ser Tyr Ile Tyr Tyr Pro Asp Ser Val Lys
            180                 185                 190

Gly Arg Phe Thr Ile Ser Arg Asp Asn Val Lys Asn Thr Leu Tyr Leu
        195                 200                 205

Gln Met Ser Ser Leu Arg Ser Glu Asp Thr Ala Met Tyr Tyr Cys Ala
    210                 215                 220

Arg Arg Asp Tyr Asp Leu Asp Tyr Phe Asp Ser Trp Gly Gln Gly Thr
225                 230                 235                 240

Leu Val Thr Val Ser Ser Glu Ser Lys Tyr Gly Pro Pro Cys Pro Pro
            245                 250                 255

Cys Pro Ala Pro Glu Phe Glu Gly Gly Pro Ser Val Phe Leu Phe Pro
        260                 265                 270

Pro Lys Pro Lys Asp Thr Leu Met Ile Ser Arg Thr Pro Glu Val Thr
        275                 280                 285

Cys Val Val Val Asp Val Ser Gln Glu Asp Pro Glu Val Gln Phe Asn
        290                 295                 300

Trp Tyr Val Asp Gly Val Glu Val His Asn Ala Lys Thr Lys Pro Arg
305                 310                 315                 320

Glu Glu Gln Phe Gln Ser Thr Tyr Arg Val Val Ser Val Leu Thr Val
                325                 330                 335

Leu His Gln Asp Trp Leu Asn Gly Lys Glu Tyr Lys Cys Lys Val Ser
                340                 345                 350

Asn Lys Gly Leu Pro Ser Ser Ile Glu Lys Thr Ile Ser Lys Ala Lys
            355                 360                 365

Gly Gln Pro Arg Glu Pro Gln Val Tyr Thr Leu Pro Pro Ser Gln Glu
        370                 375                 380

Glu Met Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
```

```
                    420                 425                 430
Phe Leu Tyr Ser Arg Leu Thr Val Asp Lys Ser Arg Trp Gln Glu Gly
                435                 440                 445

Asn Val Phe Ser Cys Ser Val Met His Glu Ala Leu His Asn His Tyr
            450                 455                 460

Thr Gln Lys Ser Leu Ser Leu Ser Leu Gly Lys Met Ala Leu Ile Val
465                 470                 475                 480

Leu Gly Gly Val Ala Gly Leu Leu Phe Ile Gly Leu Gly Ile Phe
                485                 490                 495

Phe Ala Val Ser Leu Ser Lys Met Leu Lys Lys Arg Ser Pro Leu Thr
            500                 505                 510

Thr Gly Val Tyr Val Lys Met Pro Pro Thr Glu Pro Glu Cys Glu Lys
            515                 520                 525

Gln Phe Gln Pro Tyr Phe Ile Pro Ile Asn Gly Gly Arg Val Lys
            530                 535                 540

Phe Ser Arg Ser Ala Asp Ala Pro Ala Tyr Gln Gln Gly Gln Asn Gln
545                 550                 555                 560

Leu Tyr Asn Glu Leu Asn Leu Gly Arg Arg Glu Glu Tyr Asp Val Leu
                565                 570                 575

Asp Lys Arg Arg Gly Arg Asp Pro Glu Met Gly Gly Lys Pro Arg Arg
            580                 585                 590

Lys Asn Pro Gln Glu Gly Leu Tyr Asn Glu Leu Gln Lys Asp Lys Met
            595                 600                 605

Ala Glu Ala Tyr Ser Glu Ile Gly Met Lys Gly Glu Arg Arg Arg Gly
            610                 615                 620

Lys Gly His Asp Gly Leu Tyr Gln Gly Leu Ser Thr Ala Thr Lys Asp
625                 630                 635                 640

Thr Tyr Asp Ala Leu His Met Gln Ala Leu Pro Pro Arg
                645                 650

<210> SEQ ID NO 86
<211> LENGTH: 675
<212> TYPE: PRT
<213> ORGANISM: Artificial Sequence
<220> FEATURE:
<223> OTHER INFORMATION: chimeric antigen receptor

<400> SEQUENCE: 86

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Ser Pro Ser Ser
            20                  25                  30

Leu Ser Ala Ser Val Gly Asp Arg Val Thr Ile Thr Cys Lys Ala Ser
        35                  40                  45

Arg Asp Ile Arg Ser Tyr Leu Thr Trp Tyr Gln Gln Lys Pro Gly Lys
    50                  55                  60

Ala Pro Lys Thr Leu Ile Tyr Tyr Ala Thr Ser Leu Ala Asp Gly Val
65                  70                  75                  80

Pro Ser Arg Phe Ser Gly Ser Gly Ser Gly Gln Asp Tyr Ser Leu Thr
                85                  90                  95

Ile Ser Ser Leu Glu Ser Asp Asp Thr Ala Thr Tyr Tyr Cys Leu Gln
            100                 105                 110

His Gly Glu Ser Pro Phe Thr Phe Gly Ser Gly Thr Lys Leu Glu Ile
        115                 120                 125

Lys Arg Ala Gly Ser Thr Ser Gly Gly Gly Ser Gly Gly Gly Ser Gly
```

```
                130             135              140
Gly Gly Gly Ser Ser Glu Val Gln Leu Val Glu Ser Gly Gly Leu
145             150              155              160

Val Lys Pro Gly Gly Ser Leu Lys Leu Ser Cys Ala Ala Ser Gly Phe
                165              170              175

Lys Phe Ser Arg Tyr Ala Met Ser Trp Val Arg Gln Ala Pro Gly Lys
                180              185              190

Arg Leu Glu Trp Val Ala Thr Ile Ser Ser Gly Gly Ser Tyr Ile Tyr
            195              200              205

Tyr Pro Asp Ser Val Lys Gly Arg Phe Thr Ile Ser Arg Asp Asn Val
210             215              220

Lys Asn Thr Leu Tyr Leu Gln Met Ser Ser Leu Arg Ser Glu Asp Thr
225             230              235              240

Ala Met Tyr Tyr Cys Ala Arg Arg Asp Tyr Asp Leu Asp Tyr Phe Asp
                245              250              255

Ser Trp Gly Gln Gly Thr Leu Val Thr Val Ser Ser Glu Ser Lys Tyr
                260              265              270

Gly Pro Pro Cys Pro Pro Cys Pro Ala Pro Glu Phe Glu Gly Gly Pro
                275              280              285

Ser Val Phe Leu Phe Pro Pro Lys Pro Lys Asp Thr Leu Met Ile Ser
            290              295              300

Arg Thr Pro Glu Val Thr Cys Val Val Val Asp Val Ser Gln Glu Asp
305             310              315              320

Pro Glu Val Gln Phe Asn Trp Tyr Val Asp Gly Val Glu Val His Asn
                325              330              335

Ala Lys Thr Lys Pro Arg Glu Glu Gln Phe Gln Ser Thr Tyr Arg Val
                340              345              350

Val Ser Val Leu Thr Val Leu His Gln Asp Trp Leu Asn Gly Lys Glu
            355              360              365

Tyr Lys Cys Lys Val Ser Asn Lys Gly Leu Pro Ser Ser Ile Glu Lys
            370              375              380

Thr Ile Ser Lys Ala Lys Gly Gln Pro Arg Glu Pro Gln Val Tyr Thr
385             390              395              400

Leu Pro Pro Ser Gln Glu Glu Met Thr Lys Asn Gln Val Ser Leu Thr
                405              410              415

Cys Leu Val Lys Gly Phe Tyr Pro Ser Asp Ile Ala Val Glu Trp Glu
                420              425              430

Ser Asn Gly Gln Pro Glu Asn Asn Tyr Lys Thr Thr Pro Pro Val Leu
            435              440              445

Asp Ser Asp Gly Ser Phe Phe Leu Tyr Ser Arg Leu Thr Val Asp Lys
450             455              460

Ser Arg Trp Gln Glu Gly Asn Val Phe Ser Cys Ser Val Met His Glu
465             470              475              480

Ala Leu His Asn His Tyr Thr Gln Lys Ser Leu Ser Leu Ser Leu Gly
                485              490              495

Lys Met Ala Leu Ile Val Leu Gly Gly Val Ala Gly Leu Leu Leu Phe
                500              505              510

Ile Gly Leu Gly Ile Phe Phe Ala Val Ser Leu Ser Lys Met Leu Lys
            515              520              525

Lys Arg Ser Pro Leu Thr Thr Gly Val Tyr Val Lys Met Pro Pro Thr
            530              535              540

Glu Pro Glu Cys Glu Lys Gln Phe Gln Pro Tyr Phe Ile Pro Ile Asn
545             550              555              560
```

```
Gly Gly Gly Arg Val Lys Phe Ser Arg Ser Ala Asp Ala Pro Ala Tyr
            565                 570                 575

Gln Gln Gly Gln Asn Gln Leu Tyr Asn Glu Leu Asn Leu Gly Arg Arg
            580                 585                 590

Glu Glu Tyr Asp Val Leu Asp Lys Arg Arg Gly Arg Asp Pro Glu Met
            595                 600                 605

Gly Gly Lys Pro Arg Arg Lys Asn Pro Gln Glu Gly Leu Tyr Asn Glu
            610                 615                 620

Leu Gln Lys Asp Lys Met Ala Glu Ala Tyr Ser Glu Ile Gly Met Lys
625                 630                 635                 640

Gly Glu Arg Arg Arg Gly Lys Gly His Asp Gly Leu Tyr Gln Gly Leu
                645                 650                 655

Ser Thr Ala Thr Lys Asp Thr Tyr Asp Ala Leu His Met Gln Ala Leu
                660                 665                 670

Pro Pro Arg
        675

<210> SEQ ID NO 87
<211> LENGTH: 654
<212> TYPE: PRT
<213> ORGANISM: Artificial Sequence
<220> FEATURE:
<223> OTHER INFORMATION: chimeric antigen receptor

<400> SEQUENCE: 87

Glu Val Gln Leu Val Glu Ser Gly Gly Leu Val Lys Pro Gly Gly
1               5                   10                  15

Ser Leu Lys Leu Ser Cys Ala Ala Ser Gly Phe Lys Phe Ser Arg Tyr
                20                  25                  30

Ala Met Ser Trp Val Arg Gln Ala Pro Gly Lys Arg Leu Glu Trp Val
            35                  40                  45

Ala Thr Ile Ser Ser Gly Gly Ser Tyr Ile Tyr Tyr Pro Asp Ser Val
        50                  55                  60

Lys Gly Arg Phe Thr Ile Ser Arg Asp Asn Val Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Arg Asp Tyr Asp Leu Asp Tyr Phe Asp Ser Trp Gly Gln Gly
            100                 105                 110

Thr Leu Val Thr Val Ser Ser Gly Ser Thr Ser Gly Gly Gly Ser Gly
        115                 120                 125

Gly Gly Ser Gly Gly Gly Gly Ser Ser Asp Ile Gln Met Thr Gln Ser
    130                 135                 140

Pro Ser Ser Leu Ser Ala Ser Val Gly Asp Arg Val Thr Ile Thr Cys
145                 150                 155                 160

Lys Ala Ser Arg Asp Ile Arg Ser Tyr Leu Thr Trp Tyr Gln Gln Lys
                165                 170                 175

Pro Gly Lys Ala Pro Lys Thr Leu Ile Tyr Tyr Ala Thr Ser Leu Ala
            180                 185                 190

Asp Gly Val Pro Ser Arg Phe Ser Gly Ser Gly Ser Gly Gln Asp Tyr
        195                 200                 205

Ser Leu Thr Ile Ser Ser Leu Glu Ser Asp Asp Thr Ala Thr Tyr Tyr
    210                 215                 220

Cys Leu Gln His Gly Glu Ser Pro Phe Thr Phe Gly Ser Gly Thr Lys
225                 230                 235                 240
```

```
Leu Glu Ile Lys Arg Ala Glu Ser Lys Tyr Gly Pro Pro Cys Pro Pro
            245                 250                 255

Cys Pro Ala Pro Glu Phe Glu Gly Gly Pro Ser Val Phe Leu Phe Pro
                260                 265                 270

Pro Lys Pro Lys Asp Thr Leu Met Ile Ser Arg Thr Pro Glu Val Thr
            275                 280                 285

Cys Val Val Val Asp Val Ser Gln Glu Asp Pro Glu Val Gln Phe Asn
        290                 295                 300

Trp Tyr Val Asp Gly Val Glu Val His Asn Ala Lys Thr Lys Pro Arg
305                 310                 315                 320

Glu Glu Gln Phe Gln Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Gly Leu Pro Ser Ser Ile Glu Lys Thr Ile Ser Lys Ala Lys
        355                 360                 365

Gly Gln Pro Arg Glu Pro Gln Val Tyr Thr Leu Pro Pro Ser Gln Glu
        370                 375                 380

Glu Met Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
            405                 410                 415

Asn Asn Tyr Lys Thr Thr Pro Pro Val Leu Asp Ser Asp Gly Ser Phe
            420                 425                 430

Phe Leu Tyr Ser Arg Leu Thr Val Asp Lys Ser Arg Trp Gln Glu Gly
        435                 440                 445

Asn Val Phe Ser Cys Ser Val Met His Glu Ala Leu His Asn His Tyr
        450                 455                 460

Thr Gln Lys Ser Leu Ser Leu Ser Leu Gly Lys Met Ala Leu Ile Val
465                 470                 475                 480

Leu Gly Gly Val Ala Gly Leu Leu Leu Phe Ile Gly Leu Gly Ile Phe
            485                 490                 495

Phe Lys Arg Gly Arg Lys Lys Leu Leu Tyr Ile Phe Lys Gln Pro Phe
            500                 505                 510

Met Arg Pro Val Gln Thr Thr Gln Glu Glu Asp Gly Cys Ser Cys Arg
            515                 520                 525

Phe Pro Glu Glu Glu Glu Gly Gly Cys Glu Leu Gly Gly Gly Arg Val
        530                 535                 540

Lys Phe Ser Arg Ser Ala Asp Ala Pro Ala Tyr Gln Gln Gly Gln Asn
545                 550                 555                 560

Gln Leu Tyr Asn Glu Leu Asn Leu Gly Arg Arg Glu Glu Tyr Asp Val
                565                 570                 575

Leu Asp Lys Arg Arg Gly Arg Asp Pro Glu Met Gly Gly Lys Pro Arg
            580                 585                 590

Arg Lys Asn Pro Gln Glu Gly Leu Tyr Asn Glu Leu Gln Lys Asp Lys
            595                 600                 605

Met Ala Glu Ala Tyr Ser Glu Ile Gly Met Lys Gly Glu Arg Arg Arg
            610                 615                 620

Gly Lys Gly His Asp Gly Leu Tyr Gln Gly Leu Ser Thr Ala Thr Lys
625                 630                 635                 640

Asp Thr Tyr Asp Ala Leu His Met Gln Ala Leu Pro Pro Arg
            645                 650
```

<210> SEQ ID NO 88
<211> LENGTH: 676
<212> TYPE: PRT
<213> ORGANISM: Artificial Sequence
<220> FEATURE:
<223> OTHER INFORMATION: chimeric antigen receptor

<400> SEQUENCE: 88

```
Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
            20                  25                  30

Leu Val Lys Pro Gly Gly Ser Leu Lys Leu Ser Cys Ala Ala Ser Gly
        35                  40                  45

Phe Lys Phe Ser Arg Tyr Ala Met Ser Trp Val Arg Gln Ala Pro Gly
    50                  55                  60

Lys Arg Leu Glu Trp Val Ala Thr Ile Ser Ser Gly Gly Ser Tyr Ile
65                  70                  75                  80

Tyr Tyr Pro Asp Ser Val Lys Gly Arg Phe Thr Ile Ser Arg Asp Asn
                85                  90                  95

Val Lys Asn Thr Leu Tyr Leu Gln Met Ser Ser Leu Arg Ser Glu Asp
            100                 105                 110

Thr Ala Met Tyr Tyr Cys Ala Arg Arg Asp Tyr Asp Leu Asp Tyr Phe
        115                 120                 125

Asp Ser Trp Gly Gln Gly Thr Leu Val Thr Val Ser Ser Gly Ser Thr
    130                 135                 140

Ser Gly Gly Gly Ser Gly Gly Gly Ser Gly Gly Gly Gly Ser Ser Asp
145                 150                 155                 160

Ile Gln Met Thr Gln Ser Pro Ser Ser Leu Ser Ala Ser Val Gly Asp
                165                 170                 175

Arg Val Thr Ile Thr Cys Lys Ala Ser Arg Asp Ile Arg Ser Tyr Leu
            180                 185                 190

Thr Trp Tyr Gln Gln Lys Pro Gly Lys Ala Pro Lys Thr Leu Ile Tyr
        195                 200                 205

Tyr Ala Thr Ser Leu Ala Asp Gly Val Pro Ser Arg Phe Ser Gly Ser
    210                 215                 220

Gly Ser Gly Gln Asp Tyr Ser Leu Thr Ile Ser Ser Leu Glu Ser Asp
225                 230                 235                 240

Asp Thr Ala Thr Tyr Tyr Cys Leu Gln His Gly Glu Ser Pro Phe Thr
                245                 250                 255

Phe Gly Ser Gly Thr Lys Leu Glu Ile Lys Arg Ala Glu Ser Lys Tyr
            260                 265                 270

Gly Pro Pro Cys Pro Pro Cys Pro Ala Pro Glu Phe Glu Gly Gly Pro
        275                 280                 285

Ser Val Phe Leu Phe Pro Pro Lys Pro Lys Asp Thr Leu Met Ile Ser
    290                 295                 300

Arg Thr Pro Glu Val Thr Cys Val Val Val Asp Val Ser Gln Glu Asp
305                 310                 315                 320

Pro Glu Val Gln Phe Asn Trp Tyr Val Asp Gly Val Glu Val His Asn
                325                 330                 335

Ala Lys Thr Lys Pro Arg Glu Glu Gln Phe Gln Ser Thr Tyr Arg Val
            340                 345                 350

Val Ser Val Leu Thr Val Leu His Gln Asp Trp Leu Asn Gly Lys Glu
        355                 360                 365
```

Tyr Lys Cys Lys Val Ser Asn Lys Gly Leu Pro Ser Ser Ile Glu Lys
    370                 375                 380

Thr Ile Ser Lys Ala Lys Gly Gln Pro Arg Glu Pro Gln Val Tyr Thr
385                 390                 395                 400

Leu Pro Pro Ser Gln Glu Glu Met Thr Lys Asn Gln Val Ser Leu Thr
                405                 410                 415

Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
        435                 440                 445

Asp Ser Asp Gly Ser Phe Phe Leu Tyr Ser Arg Leu Thr Val Asp Lys
450                 455                 460

Ser Arg Trp Gln Glu Gly Asn Val Phe Ser Cys Ser Val Met His Glu
465                 470                 475                 480

Ala Leu His Asn His Tyr Thr Gln Lys Ser Leu Ser Leu Ser Leu Gly
                485                 490                 495

Lys Met Ala Leu Ile Val Leu Gly Gly Val Ala Gly Leu Leu Leu Phe
            500                 505                 510

Ile Gly Leu Gly Ile Phe Phe Lys Arg Gly Arg Lys Lys Leu Leu Tyr
        515                 520                 525

Ile Phe Lys Gln Pro Phe Met Arg Pro Val Gln Thr Thr Gln Glu Glu
530                 535                 540

Asp Gly Cys Ser Cys Arg Phe Pro Glu Glu Glu Gly Gly Cys Glu
545                 550                 555                 560

Leu Gly Gly Gly Arg Val Lys Phe Ser Arg Ser Ala Asp Ala Pro Ala
                565                 570                 575

Tyr Gln Gln Gly Gln Asn Gln Leu Tyr Asn Glu Leu Asn Leu Gly Arg
            580                 585                 590

Arg Glu Glu Tyr Asp Val Leu Asp Lys Arg Arg Gly Arg Asp Pro Glu
        595                 600                 605

Met Gly Gly Lys Pro Arg Arg Lys Asn Pro Gln Glu Gly Leu Tyr Asn
610                 615                 620

Glu Leu Gln Lys Asp Lys Met Ala Glu Ala Tyr Ser Glu Ile Gly Met
625                 630                 635                 640

Lys Gly Glu Arg Arg Arg Gly Lys Gly His Asp Gly Leu Tyr Gln Gly
                645                 650                 655

Leu Ser Thr Ala Thr Lys Asp Thr Tyr Asp Ala Leu His Met Gln Ala
            660                 665                 670

Leu Pro Pro Arg
        675

<210> SEQ ID NO 89
<211> LENGTH: 654
<212> TYPE: PRT
<213> ORGANISM: Artificial Sequence
<220> FEATURE:
<223> OTHER INFORMATION: chimeric antigen receptor

<400> SEQUENCE: 89

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Ile Arg Ser Tyr
            20                  25                  30

Leu Thr Trp Tyr Gln Gln Lys Pro Gly Lys Ala Pro Lys Thr Leu Ile
        35                  40                  45

```
Tyr Tyr Ala Thr Ser Leu Ala Asp Gly Val Pro Ser Arg Phe Ser Gly
 50               55                  60
Ser Gly Ser Gly Gln Asp Tyr Ser Leu Thr Ile Ser Ser Leu Glu Ser
 65               70                  75                  80
Asp Asp Thr Ala Thr Tyr Tyr Cys Leu Gln His Gly Glu Ser Pro Phe
                 85                  90                  95
Thr Phe Gly Ser Gly Thr Lys Leu Glu Ile Lys Arg Ala Gly Ser Thr
                100                 105                 110
Ser Gly Gly Gly Ser Gly Gly Ser Gly Gly Gly Gly Ser Ser Glu
            115                 120                 125
Val Gln Leu Val Glu Ser Gly Gly Leu Val Lys Pro Gly Gly Ser
130                 135                 140
Leu Lys Leu Ser Cys Ala Ala Ser Gly Phe Lys Phe Ser Arg Tyr Ala
145                 150                 155                 160
Met Ser Trp Val Arg Gln Ala Pro Gly Lys Arg Leu Glu Trp Val Ala
                165                 170                 175
Thr Ile Ser Ser Gly Gly Ser Tyr Ile Tyr Tyr Pro Asp Ser Val Lys
                180                 185                 190
Gly Arg Phe Thr Ile Ser Arg Asp Asn Val Lys Asn Thr Leu Tyr Leu
                195                 200                 205
Gln Met Ser Ser Leu Arg Ser Glu Asp Thr Ala Met Tyr Tyr Cys Ala
210                 215                 220
Arg Arg Asp Tyr Asp Leu Asp Tyr Phe Asp Ser Trp Gly Gln Gly Thr
225                 230                 235                 240
Leu Val Thr Val Ser Ser Glu Ser Lys Tyr Gly Pro Pro Cys Pro Pro
                245                 250                 255
Cys Pro Ala Pro Glu Phe Glu Gly Gly Pro Ser Val Phe Leu Phe Pro
                260                 265                 270
Pro Lys Pro Lys Asp Thr Leu Met Ile Ser Arg Thr Pro Glu Val Thr
                275                 280                 285
Cys Val Val Val Asp Val Ser Gln Glu Asp Pro Glu Val Gln Phe Asn
290                 295                 300
Trp Tyr Val Asp Gly Val Glu Val His Asn Ala Lys Thr Lys Pro Arg
305                 310                 315                 320
Glu Glu Gln Phe Gln Ser Thr Tyr Arg Val Val Ser Val Leu Thr Val
                325                 330                 335
Leu His Gln Asp Trp Leu Asn Gly Lys Glu Tyr Lys Cys Lys Val Ser
                340                 345                 350
Asn Lys Gly Leu Pro Ser Ser Ile Glu Lys Thr Ile Ser Lys Ala Lys
                355                 360                 365
Gly Gln Pro Arg Glu Pro Gln Val Tyr Thr Leu Pro Pro Ser Gln Glu
                370                 375                 380
Glu Met Thr Lys Asn Gln Val Ser Leu Thr Cys Leu Val Lys Gly Phe
385                 390                 395                 400
Tyr Pro Ser Asp Ile Ala Val Glu Trp Glu Ser Asn Gly Gln Pro Glu
                405                 410                 415
Asn Asn Tyr Lys Thr Thr Pro Pro Val Leu Asp Ser Asp Gly Ser Phe
                420                 425                 430
Phe Leu Tyr Ser Arg Leu Thr Val Asp Lys Ser Arg Trp Gln Glu Gly
                435                 440                 445
Asn Val Phe Ser Cys Ser Val Met His Glu Ala Leu His Asn His Tyr
450                 455                 460
Thr Gln Lys Ser Leu Ser Leu Ser Leu Gly Lys Met Ala Leu Ile Val
```

```
465                 470                 475                 480
Leu Gly Gly Val Ala Gly Leu Leu Phe Ile Gly Leu Gly Ile Phe
                485                 490                 495

Phe Lys Arg Gly Arg Lys Leu Leu Tyr Ile Phe Lys Gln Pro Phe
                500                 505                 510

Met Arg Pro Val Gln Thr Thr Gln Glu Glu Asp Gly Cys Ser Cys Arg
                515                 520                 525

Phe Pro Glu Glu Glu Gly Gly Cys Glu Leu Gly Gly Gly Arg Val
                530                 535                 540

Lys Phe Ser Arg Ser Ala Asp Ala Pro Ala Tyr Gln Gln Gly Gln Asn
545                 550                 555                 560

Gln Leu Tyr Asn Glu Leu Asn Leu Gly Arg Arg Glu Tyr Asp Val
                565                 570                 575

Leu Asp Lys Arg Arg Gly Arg Asp Pro Glu Met Gly Gly Lys Pro Arg
                580                 585                 590

Arg Lys Asn Pro Gln Glu Gly Leu Tyr Asn Glu Leu Gln Lys Asp Lys
                595                 600                 605

Met Ala Glu Ala Tyr Ser Glu Ile Gly Met Lys Gly Glu Arg Arg Arg
610                 615                 620

Gly Lys Gly His Asp Gly Leu Tyr Gln Gly Leu Ser Thr Ala Thr Lys
625                 630                 635                 640

Asp Thr Tyr Asp Ala Leu His Met Gln Ala Leu Pro Pro Arg
                645                 650
```

<210> SEQ ID NO 90
<211> LENGTH: 676
<212> TYPE: PRT
<213> ORGANISM: Artificial Sequence
<220> FEATURE:
<223> OTHER INFORMATION: chimeric antigen receptor

<400> SEQUENCE: 90

```
Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Ser Pro Ser Ser
                20                  25                  30

Leu Ser Ala Ser Val Gly Asp Arg Val Thr Ile Thr Cys Lys Ala Ser
                35                  40                  45

Arg Asp Ile Arg Ser Tyr Leu Thr Trp Tyr Gln Gln Lys Pro Gly Lys
                50                  55                  60

Ala Pro Lys Thr Leu Ile Tyr Tyr Ala Thr Ser Leu Ala Asp Gly Val
65                  70                  75                  80

Pro Ser Arg Phe Ser Gly Ser Gly Ser Gly Gln Asp Tyr Ser Leu Thr
                85                  90                  95

Ile Ser Ser Leu Glu Ser Asp Asp Thr Ala Thr Tyr Tyr Cys Leu Gln
                100                 105                 110

His Gly Glu Ser Pro Phe Thr Phe Gly Ser Gly Thr Lys Leu Glu Ile
                115                 120                 125

Lys Arg Ala Gly Ser Thr Ser Gly Gly Gly Ser Gly Gly Ser Gly
                130                 135                 140

Gly Gly Gly Ser Ser Glu Val Gln Leu Val Glu Ser Gly Gly Gly Leu
145                 150                 155                 160

Val Lys Pro Gly Gly Ser Leu Lys Leu Ser Cys Ala Ala Ser Gly Phe
                165                 170                 175

Lys Phe Ser Arg Tyr Ala Met Ser Trp Val Arg Gln Ala Pro Gly Lys
```

-continued

```
                180                 185                 190
Arg Leu Glu Trp Val Ala Thr Ile Ser Ser Gly Gly Ser Tyr Ile Tyr
            195                 200                 205

Tyr Pro Asp Ser Val Lys Gly Arg Phe Thr Ile Ser Arg Asp Asn Val
        210                 215                 220

Lys Asn Thr Leu Tyr Leu Gln Met Ser Ser Leu Arg Ser Glu Asp Thr
225                 230                 235                 240

Ala Met Tyr Tyr Cys Ala Arg Arg Asp Tyr Asp Leu Asp Tyr Phe Asp
                245                 250                 255

Ser Trp Gly Gln Gly Thr Leu Val Thr Val Ser Ser Glu Ser Lys Tyr
            260                 265                 270

Gly Pro Pro Cys Pro Pro Cys Pro Ala Pro Glu Phe Glu Gly Gly Pro
        275                 280                 285

Ser Val Phe Leu Phe Pro Lys Pro Lys Asp Thr Leu Met Ile Ser
290                 295                 300

Arg Thr Pro Glu Val Thr Cys Val Val Val Asp Val Ser Gln Glu Asp
305                 310                 315                 320

Pro Glu Val Gln Phe Asn Trp Tyr Val Asp Gly Val Glu Val His Asn
                325                 330                 335

Ala Lys Thr Lys Pro Arg Glu Glu Gln Phe Gln Ser Thr Tyr Arg Val
            340                 345                 350

Val Ser Val Leu Thr Val Leu His Gln Asp Trp Leu Asn Gly Lys Glu
        355                 360                 365

Tyr Lys Cys Lys Val Ser Asn Lys Gly Leu Pro Ser Ser Ile Glu Lys
370                 375                 380

Thr Ile Ser Lys Ala Lys Gly Gln Pro Arg Glu Pro Gln Val Tyr Thr
385                 390                 395                 400

Leu Pro Pro Ser Gln Glu Glu Met Thr Lys Asn Gln Val Ser Leu Thr
                405                 410                 415

Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
        435                 440                 445

Asp Ser Asp Gly Ser Phe Phe Leu Tyr Ser Arg Leu Thr Val Asp Lys
        450                 455                 460

Ser Arg Trp Gln Glu Gly Asn Val Phe Ser Cys Ser Val Met His Glu
465                 470                 475                 480

Ala Leu His Asn His Tyr Thr Gln Lys Ser Leu Ser Leu Ser Leu Gly
                485                 490                 495

Lys Met Ala Leu Ile Val Leu Gly Gly Val Ala Gly Leu Leu Leu Phe
            500                 505                 510

Ile Gly Leu Gly Ile Phe Phe Lys Arg Gly Arg Lys Lys Leu Leu Tyr
        515                 520                 525

Ile Phe Lys Gln Pro Phe Met Arg Pro Val Gln Thr Thr Gln Glu Glu
        530                 535                 540

Asp Gly Cys Ser Cys Arg Phe Pro Glu Glu Glu Glu Gly Gly Cys Glu
545                 550                 555                 560

Leu Gly Gly Gly Arg Val Lys Phe Ser Arg Ser Ala Asp Ala Pro Ala
                565                 570                 575

Tyr Gln Gln Gly Gln Asn Gln Leu Tyr Asn Glu Leu Asn Leu Gly Arg
            580                 585                 590

Arg Glu Glu Tyr Asp Val Leu Asp Lys Arg Arg Gly Arg Asp Pro Glu
        595                 600                 605
```

```
Met Gly Gly Lys Pro Arg Arg Lys Asn Pro Gln Gly Leu Tyr Asn
    610             615             620

Glu Leu Gln Lys Asp Lys Met Ala Glu Ala Tyr Ser Glu Ile Gly Met
625             630             635             640

Lys Gly Glu Arg Arg Arg Gly Lys Gly His Asp Gly Leu Tyr Gln Gly
            645             650             655

Leu Ser Thr Ala Thr Lys Asp Thr Tyr Asp Ala Leu His Met Gln Ala
            660             665             670

Leu Pro Pro Arg
        675

<210> SEQ ID NO 91
<211> LENGTH: 229
<212> TYPE: PRT
<213> ORGANISM: Homo sapiens

<400> SEQUENCE: 91

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Gln Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Lys
225

<210> SEQ ID NO 92
<211> LENGTH: 112
<212> TYPE: PRT
<213> ORGANISM: Homo sapiens

<400> SEQUENCE: 92

Arg Val Lys Phe Ser Arg Ser Ala Asp Ala Pro Ala Tyr Gln Gln Gly
1               5                   10                  15
```

```
Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110

<210> SEQ ID NO 93
<211> LENGTH: 68
<212> TYPE: PRT
<213> ORGANISM: Homo sapiens

<400> SEQUENCE: 93

Ile Gln Met Thr Gln Ser Pro Ser Ser Leu Ser Ala Ser Val Gly Asp
1               5                   10                  15

Arg Val Thr Ile Thr Cys Lys Ala Ser Arg Asp Ile Arg Ser Tyr Leu
                20                  25                  30

Thr Trp Tyr Gln Gln Lys Pro Gly Lys Ala Pro Lys Thr Leu Ile Tyr
            35                  40                  45

Tyr Ala Thr Ser Leu Ala Asp Gly Val Pro Ser Arg Phe Ser Gly Ser
        50                  55                  60

Gly Ser Gly Gln
65
```

CD6 TARGETED CHIMERIC ANTIGEN RECEPTORS FOR TREATMENT OF CERTAIN AUTOIMMUNE DISORDERS

CLAIM OF PRIORITY

This application is a U.S. National Phase Application under 35 U.S.C. § 371 of International Application No. PCT/US2019/040185, filed on Jul. 1, 2019, which claims priority to and the benefit of U.S. Provisional Application No. 62/692,609, filed on Jun. 29, 2018. The entire contents of the foregoing are incorporated herein by reference.

SEQUENCE LISTING

This application contains a Sequence Listing that has been submitted electronically as an ASCII text file named 40056-0051US1_ST25.txt. The ASCII text file, created on Nov. 8, 2024, is 158,141 bytes in size. The material in the ASCII text file is hereby incorporated by reference in its entirety.

BACKGROUND

Type 1 diabetes mellitus (T1D) precipitates from the autoimmune attack of pancreatic beta cells thereby resulting in a loss of functional beta cell mass. Functional beta cell mass is impacted positively by processes that increase the number and size of beta cells and negatively by those that deplete the numbers of cells (i.e., apoptosis, necrosis, and other modes of cell death). In addition, beta cell secretory function and capacity is a substantial determinant of functional beta cell mass.

In T1D patients, the proliferative and regenerative potential of adult and human islets is low. Thus, it is important to prevent or delay the autoimmune attack and resultant destruction of beta cells, and to establish methods to promote beta cell mass expansion, increase beta cell survival, and/or enhance the function of existing/remaining beta cells, including engaging cellular repair mechanisms to restore functional beta cell mass. However, therapeutic strategies aiming to simultaneously target the pancreatic islet-infiltrating lymphocytes along with protecting and replenishing the functional beta cell mass are limited. Provided herein are solutions to these and other problems in the art.

SUMMARY

Described herein are chimeric antigen receptors (CARs) targeted to CD6. The CD6 CAR are expressed in regulatory T cells (Tregs) to target the CD6 molecule overexpressed in pro-inflammatory T-cells in Type 1 Diabetes (T1D) patients. This approach is in contrast to targeting beta-cells antigens, an approach that may induce additional damage to pancreatic islets. In some instrances the current appoach employs CAR that include an scFv derived from Itolizumab, an immunomodulatory anti-CD6 monoclonal antibody (U.S. Pat. No. 6,572,857). The CD6 CAR used in the CD152 (CTLA-4) cytoplasmic domain (in addition to CD3 zeta) to drive inhibitory signaling in transduced host cells and reinforcing the immunomodulatory activity of CAR-Tregs. In some cases, the CD6 are relatively low affinity with respect to CD6. This can avoid over-activation of adoptively transferred cells and extend their lifespan. In some cases, the CAR are expressed in an CD6low/– subset of Tregs. Thus, in some cases the CD6 CAR are expressed in CD4+, CD25hi,CD127low/–, CD6low/– T cells. In some cases the CD6 CAR expressed in Treg can have a better safety profile compared to CAR expressed in, T effector cells (Teff) because they are less likely to trigger adverse cytokine release syndrome. Moreover, Tregs can produce anti-inflammatory molecules such as IDO, TGF-beta and IL-10. In some cases, the CD6 CAR expressed in Treg are less susceptible to lymphocyte exhaustion resulting in their extended persistence thus improving the efficacy of adoptive immunotherapy.

Provided herein are, inter alia, cells, nucleic acids, proteins, methods, and compositions for an autoimmune disease. In embodiments, the autoimmune disease is associated with reduced islet cell (e.g., beta cell) function, viability, or survival. In embodiments, the autoimmune disease includes a subject's immune system attacking the subject's islet cells (e.g., beta cells). Also provided herein are, inter alia, compositions useful for the treatment of certain autoimmune diseases. In embodiments, novel CAR-T cells targeting the human CD6 molecule are provide herein. In embodiments, chimeric antigen receptors (CARs) with different ranges of affinities for the CD6 molecule are expressed by genetic engineering in different types of human T-cells, including T regulatory cells (Tregs).

In an aspect is provided an isolated nucleic acid encoding a protein including a single chain variable fragment (scFv) targeted to CD6 and a transmembrane domain.

In an aspect, a vector including the nucleic acid provided herein, including embodiments thereof, is provided.

In an aspect, a T lymphocyte, preferably a Treg cell, including the vector provided herein, including embodiments thereof, is provided.

In an aspect, a recombinant protein including a single chain variable fragment (scFv) targeted to CD6 and a transmembrane domain, including embodiments thereof, is provided.

In an aspect, a T lymphocyte, preferably a Treg cell, including the recombinant protein provided herein, including embodiments thereof, is provided.

In an aspect is provided a method of treating an autoimmune disease. In embodiments, the method includes administering to a subject in need thereof an effective amount of a T-lymphocyte, preferably a Treg cell, as described herein, including embodiments thereof.

DESCRIPTION OF THE DRAWINGS

FIG. 1: Amino acid sequence of the CD6 CAR expressed by pF03496-CD6scFvop(VH_VL)-IgG4(L235E,N297Q)op-CTLA4-Zetaop with the various domains marked. The mature CAR, lacking the signal sequence (MLLLVTSLLL-CELPHPAFLLIP; SEQ ID NO:70) is SEQ ID NO:83. The immature sequence is SEQ ID NO:84.

FIG. 2: Amino acid sequence of the CD6 CAR expressed by pF03497-CD6scFvop(VL_VH)-IgG4(L235E,N297Q)op-CTLA4-Zetaop with the various domains marked. The mature CAR, lacking the signal sequence (MLLLVTSLLL-CELPHPAFLLIP; SEQ ID NO:70) is SEQ ID NO:85. The immature sequence is SEQ ID NO:86.

FIG. 3: Amino acid sequence of the CD6 CAR expressed by pF03488-CD6scFv(VH-VL)-IgG4op(L235E, N297Q)-41BB-Zetaop with the various domains marked. The mature CAR, lacking the signal sequence (MLLLVTSLLLCEL-PHPAFLLIP; SEQ ID NO:70) is SEQ ID NO:87. The immature sequence is SEQ ID NO:88.

FIG. 4: Amino acid sequence of the CD6 CAR expressed by pF03491-CD6scFv(VL-VH)-IgG4op(L235E, N297Q)-41BB-Zetaop with the various domains marked. The mature CAR, lacking the signal sequence (MLLLVTSLLLCEL- PHPAFLLIP; SEQ ID NO:70) is SEQ ID NO:89. The immature sequence is SEQ ID NO:90.

FIG. 10: Amino acid sequence of an alternative CD6 scFv for use in the CAR described herein (SEQ ID NO:73) the domains and mutations are indicated.

DETAILED DESCRIPTION

Figure 5:
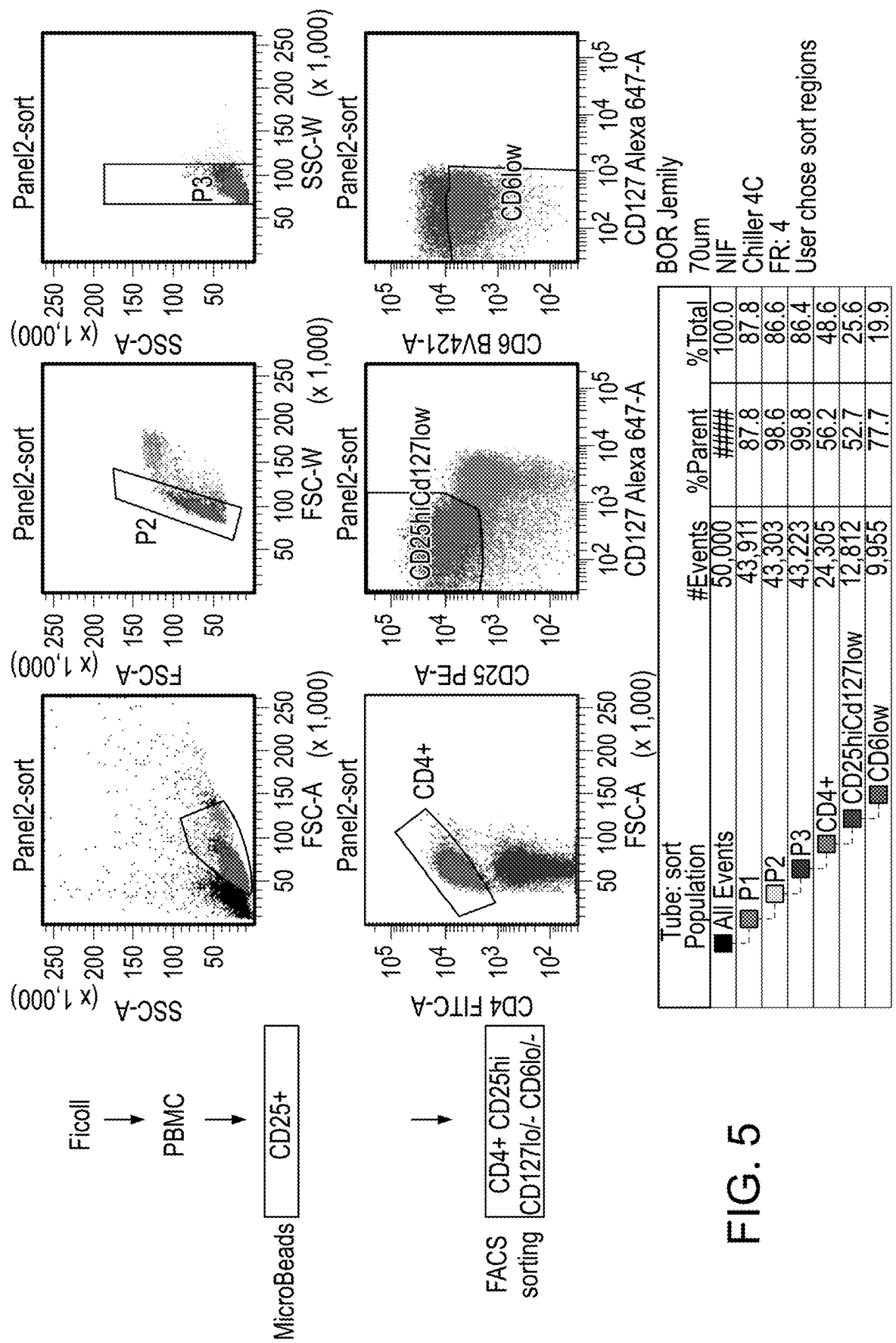
FIG. 5: Is a schematic depiction of the preparation of Tregs. CD25+ cells are isolated from PBMC. FACS sorting is then uses to enrich for CD4$^+$/CD25$^{high}$/CD127$^{low/-}$. The resulting cells are highly enriched for Tregs. Optionally, an additional step can be used to enrich for the CD6$^{low/-}$ subset of Tregs.

Surprisingly, CARs with low affinity slow, delay, or reduce the exhaustion of inoculated CAR-T cells, resulting in a longer half-life and improving efficacy for adoptive immunotherapy. In embodiments, compositions provided herein include CAR-T cells that target CD6+ T- and B-lymphocytes in the affected organs (e.g., pancreas in the case of T1D). In embodiments, the CARs provided herein have an affinity, e.g., a KD of 130 nM or higher for the CD6 molecule (i.e., protein). The CAR-T cells provided herein are contemplated as relevant for the treatment of human autoimmune diseases (e.g., Type 1 Diabetes, Multiple Sclerosis, Inflammatory Bowel Disease, or Graft-versus-Host Disease).

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

Unless defined otherwise, technical and scientific terms used herein have the same meaning as commonly understood by a person of ordinary skill in the art. See, e.g., Singleton et al.,DICTIONARY OF MICROBIOLOGY AND MOLECULAR BIOLOGY 2nd ed., J. Wiley & Sons (New York, NY 1994); Sambrook et al., MOLECULAR CLONING, A LABORATORY MANUAL, Cold Springs Harbor Press (Cold Springs Harbor, NY 1989). Any methods, devices and materials similar or equivalent to those described herein can be used in the practice of this invention. The following definitions are provided to facilitate understanding of certain terms used frequently herein and are not meant to limit the scope of the present disclosure. The abbreviations used herein have their conventional meaning within the chemical and biological arts. The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/–10% of the specified value. In embodiments, about means the specified value.

The terms "a" or "an," as used in herein means one or more.

The transitional term "comprising," which is synonymous with "including," "containing," or "characterized by," is inclusive or open-ended and does not exclude additional, unrecited elements (such as method steps or ingredients). By contrast, the transitional phrase "consisting of" excludes any element not specified in the claim. The transitional phrase "consisting essentially of" limits the scope of a claim to the specified materials or steps "and those that do not materially affect the basic and novel characteristic(s)" of the claimed invention. Where methods and compositions are disclosed using the transitional term "comprising" it will be understood that corresponding methods and compositions with the transitional term "consisting of" and "consisting essentially of" are also disclosed.

Where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to and including 5.0 mg.

In the descriptions herein and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together."

"Nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acid as used herein also refers to nucleic acids that have the same basic chemical structure as a naturally occurring nucleic acid. Such analogues have modified sugars and/or modified ring substituents, but retain the same basic chemical structure as the naturally occurring nucleic acid. A nucleic acid mimetic refers to chemical compounds that have a structure that is different from the general chemical structure of a nucleic acid, but that functions in a manner similar to a naturally occurring nucleic acid. Examples of such analogues include, without limitation, phosphorothiolates, phosphoramidates, methyl phosphonates, chiral-methyl phosphonates, 2-O-methyl ribonucleotides, and peptide-nucleic acids (PNAs).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids sequences encode any given amino acid residue. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant." In embodiments, the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that may be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence. An amino acid residue in a protein "corresponds" to a given residue when it occupies the same essential structural position within the protein as the given residue. For example, a selected residue in a selected antibody (or antigen binding domain) corresponds to light chain threonine at Kabat position 40, when the selected residue occupies the same essential spatial or other structural relationship as a light chain threonine at Kabat position 40. In some embodiments, where a selected protein is aligned for maximum homology with the light chain of an antibody (or antigen binding domain), the position in the aligned selected protein aligning with threonine 40 is said to correspond to threonine 40. Instead of a primary sequence alignment, a three dimensional structural alignment can also be used, e.g., where the structure of the selected protein is aligned for maximum correspondence with the light chain threonine at Kabat position 40, and the overall structures compared. In this case, an amino acid that occupies the same essential position as threonine 40 in the structural model is said to correspond to the threonine 40 residue.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 50%, 55%, 60%, 65%, 70%, 75%, 80%, 85%, 90%, 95%, 98%, or 99% identity over a specified region, e.g., of the entire polypeptide sequences of the invention or individual domains of the polypeptides of the invention), when compared and aligned for maximum correspondence over a comparison window, or designated region as measured using a sequence comparison algorithms or by manual alignment and visual inspection. Such sequences that are at least about 80% identical are said to be "substantially identical." In some embodiments, two sequences are 100% identical. In certain embodiments, two sequences are 100% identical over the entire length of one of the sequences (e.g., the shorter of the two sequences where the sequences have different lengths). In various embodiments, identity may refer to the complement of a test sequence. In some embodiments, the identity exists over a region that is at least about 10 to about 100, about 20 to about 75, about 30 to about 50 amino acids or nucleotides in length. In certain embodiments, the identity exists over a region that is at about 10 nucleotides in length, or more preferably over a region that is 20 to 50, 100 to 500 or 1000 or more nucleotides in length. In certain embodiments, the identity exists over a region that is at least about 50 amino acids in length, or more preferably over a region that is 100 to 500, 100 to 200, 150 to 200, 175 to 200, 175 to 225, 175 to 250, 200 to 225, 200 to 250 or more amino acids in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window" refers to a segment of any one of the number of contiguous positions (e.g., least about 10 to about 100, about 20 to about 75, about 30 to about 50, 100 to 500, 100 to 200, 150 to 200, 175 to 200, 175 to 225, 175 to 250, 200 to 225, 200 to 250) in which a sequence may be compared to a reference sequence of the same number of contiguous positions after the two sequences are optimally aligned. In various embodiments, a comparison window is the entire length of one or both of two aligned sequences. In some embodiments, two sequences being compared comprise different lengths, and the comparison window is the entire length of the longer or the shorter of the two sequences. In certain embodiments relating to two sequences of different lengths, the comparison window includes the entire length of the shorter of the two sequences. In some embodiments relating to two sequences of different lengths, the comparison window includes the entire length of the longer of the two sequences.

Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Ausubel et al., Current Protocols in Molecular Biology (1995 supplement)).

Examples of algorithm that are suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. BLAST and BLAST 2.0 may be used, with the parameters described herein, to determine percent sequence identity for nucleic acids and proteins. Software for performing BLAST analyses is publicly available through the National Center for Biotechnology Information (NCBI), as is known in the art. Software for performing BLAST analyses is publicly available through the National Center for Biotechnology Information (ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. In certain embodiments, the NCBI BLASTN or BLASTP program is used to align sequences. In certain embodiments, the BLASTN or BLASTP program uses the defaults used by the NCBI. In certain embodiments, the BLASTN program (for nucleotide sequences) uses as defaults: a word size (W) of 28; an expectation threshold (E) of 10; max matches in a query range set to 0; match/mismatch scores of 1,-2; linear gap costs; the filter for low complexity regions used; and mask for lookup table only used. In certain embodiments, the BLASTP program (for amino acid sequences) uses as defaults: a word size (W) of 3; an expectation threshold (E) of 10; max matches in a query range set to 0; the BLOSUM62 matrix (see Henikoff & Henikoff, Proc. Natl. Acad. Sci. USA 89:10915 (1992)); gap costs of existence: 11 and extension: 1; and conditional compositional score matrix adjustment.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

In certain embodiments, an indication that two nucleic acid sequences or polypeptides are substantially identical is that the polypeptide encoded by the first nucleic acid is immunologically cross-reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any appropriate method known in the art for conjugating an antibody to the label may be employed, e.g., using methods described in Hermanson, Bioconjugate Techniques 1996, Academic Press, Inc., San Diego.

A "labeled protein or polypeptide" is one that is bound, either covalently, through a linker or a chemical bond, or noncovalently, through ionic, van der Waals, electrostatic, or hydrogen bonds to a label such that the presence of the labeled protein or polypeptide may be detected by detecting the presence of the label bound to the labeled protein or polypeptide. Alternatively, methods using high affinity interactions may achieve the same results where one of a pair of binding partners binds to the other, e.g., biotin, streptavidin.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody plays a significant role in determining the specificity and affinity of binding. In some embodiments, antibodies or fragments of antibodies may be derived from different organisms, including humans, mice, rats, hamsters, camels, etc.

Antibodies of the invention may include antibodies that have been modified or mutated at one or more amino acid positions to improve or modulate a desired function of the antibody (e.g. glycosylation, expression, antigen recognition, effector functions, antigen binding, specificity, etc.).

Antibodies are large, complex molecules (molecular weight of ~150,000 or about 1320 amino acids) with intricate internal structure. A natural antibody molecule contains two identical pairs of polypeptide chains, each pair having one light chain and one heavy chain. Each light chain and heavy chain in turn consists of two regions: a variable ("V") region involved in binding the target antigen, and a constant ("C") region that interacts with other components of the immune system. The light and heavy chain variable regions come together in 3-dimensional space to form a variable region that binds the antigen (for example, a receptor on the surface of a cell). Within each light or heavy chain variable region, there are three short segments (averaging 10 amino acids in length) called the complementarity determining regions ("CDRs"). The six CDRs in an antibody variable domain (three from the light chain and three from the heavy chain) fold up together in 3-dimensional space to form the actual antibody binding site which docks onto the target antigen. The position and length of the CDRs have been precisely defined by Kabat, E. et al., Sequences of Proteins of Immunological Interest, U.S. Department of Health and Human Services, 1983, 1987. The part of a variable region not contained in the CDRs is called the framework ("FR"), which forms the environment for the CDRs.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. The Fc (i.e. fragment crystallizable region) is the "base" or "tail" of an immunoglobulin and is typically composed of two heavy chains that contribute two or three constant domains depending on the class of the antibody. By binding to specific proteins the Fc region ensures that each antibody generates an appropriate immune response for a given antigen. The Fc region also binds to various cell receptors, such as Fc receptors, and other immune molecules, such as complement proteins.

The term "antigen" as provided herein refers to molecules capable of binding to the antibody binding site.

Antibodies exist, for example, as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region, thereby converting the F(ab)'2 dimer into an Fab' monomer. The Fab' monomer is essentially the antigen binding portion with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

A single-chain variable fragment (scFv) is typically a fusion protein of the variable regions of the heavy (VH) and light chains (VL) of immunoglobulins, connected with a linker peptide (e.g., a short linker peptide of 10 to about 25 amino acids). In embodiments, the linker is rich in glycine for flexibility, as well as serine or threonine for solubility. The linker can either connect the N-terminus of the VH with the C-terminus of the VL, or vice versa.

The epitope of a mAb is the region of its antigen to which the mAb binds. Two antibodies bind to the same or overlapping epitope if each competitively inhibits (blocks) binding of the other to the antigen. That is, a 1×, 5×, 10×, 20× or 100× excess of one antibody inhibits binding of the other by at least 30% but preferably 50%, 75%, 90% or even 99% as measured in a competitive binding assay (see, e.g., Junghans et al., Cancer Res. 50:1495, 1990). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

For preparation of suitable antibodies, many techniques known in the art can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy, Alan R. Liss, Inc. (1985); Coligan, Current Protocols in Immunology (1991); Harlow & Lane, Antibodies, A Laboratory Manual (1988); and Goding, Monoclonal Antibodies: Principles and Practice (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology (3rd ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633, 425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg & Huszar, Intern. Rev. Immunol. 13:65-93 (1995)). Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)). Antibodies can also be made bispecific, i.e., able to recognize two different antigens (see, e.g., WO 93/08829, Traunecker et al., EMBO J. 10:3655-3659 (1991); and Suresh et al., Methods in Enzymology 121:210 (1986)). Antibodies can also be heteroconjugates, e.g., two covalently joined antibodies, or immunotoxins (see, e.g., U.S. Pat. No. 4,676, 980, WO 91/00360; WO 92/200373; and EP 03089).

Methods for humanizing or primatizing non-human antibodies or scFvs are well known in the art (e.g., U.S. Pat. Nos. 4,816,567; 5,530,101; 5,859,205; 5,585,089; 5,693, 761; 5,693,762; 5,777,085; 6,180,370; 6,210,671; and 6,329,511; WO 87/02671; EP Patent Application 0173494; Jones et al. (1986) Nature 321:522; and Verhoyen et al. (1988) Science 239:1534). Humanized antibodies are further described in, e.g., Winter and Milstein (1991) Nature 349: 293. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Morrison et al., PNAS USA, 81:6851-6855 (1984), Jones et al., Nature 321:522-525 (1986); Riechmann et al., Nature 332:323-327 (1988); Morrison and Oi, Adv. Immunol., 44:65-92 (1988), Verhoeyen et al., Science 239:1534-1536 (1988) and Presta, Curr. Op. Struct. Biol. 2:593-596 (1992), Padlan, Molec. Immun., 28:489-498 (1991); Padlan, Molec. Immun., 31(3):169-217 (1994)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies. For example, polynucleotides comprising a first sequence coding for humanized immunoglobulin framework regions and a second sequence set coding for the desired immunoglobulin complementarity determining regions can be produced synthetically or by combining appropriate cDNA and genomic DNA segments. Human constant region DNA sequences can be isolated in accordance with well known procedures from a variety of human cells.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the invention include humanized and/or chimeric monoclonal antibodies.

A "therapeutic antibody" as provided herein refers to any antibody or functional fragment thereof that is used to treat cancer, autoimmune diseases, transplant rejection, cardiovascular disease or other diseases or conditions such as those described herein.

Techniques for conjugating therapeutic agents to antibodies are well known (see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery" in Controlled Drug Delivery ($2^{nd}$ Ed.), Robinson et al. (eds.), pp. 623-53 (Marcel Dekker, Inc. 1987); Thorpe, "Antibody Carriers Of Cytotoxic Agents In Cancer Therapy: A Review" in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", Immunol. Rev., 62:119-58 (1982)). As used herein, the term "antibody-drug conjugate" or "ADC" refers to a therapeutic agent conjugated or otherwise covalently bound to an antibody. A "therapeutic agent" as referred to herein, is a composition useful in treating or preventing a disease such as an autoimmune disease.

The term "anti-CD6 antibody" as used herein refers to an antibody capable of binding CD6 through the antibody CDR sequences. Thus, the anti-CD6 antibody includes an antibody binding site composed of CDRs CDRs (e.g., VL-CDR1, VL-CDR2, VL-CDR3, VH-CDR1, VH-CDR2, VH-CDR3) that specifically bind CD6

"CD6", also known as TP120, as referred to herein includes any of the recombinant or naturally-occurring forms of cluster of differentiation 6 (CD6) protein or variants or homologs thereof that maintain CD6 activity (e.g. within at least 50%, 80%, 90%, 95%, 96%, 97%, 98%, 99% or 100% activity compared to CD6). In aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD6 protein. In some cases, the CD6 protein is substantially identical to the protein identified by the UniProt reference number P30203 or a variant or homolog having substantial identity thereto. In some cases, CD6 is a human CD6 protein. In some cases, a variant or mutant of the CD6 protein includes no more than 5, 4, 3, 2, or 1 deletions compared to a naturally occurring CD6 protein. In some cases, a variant or mutant of the CD6 protein includes no more than 5, 4, 3, 2, or 1 insertions compared to the naturally-occurring CD6 protein. In some cases, a variant or mutant of the CD6 protein does not include deletions compared to the naturally occurring CD6 protein. In some cases, a variant or mutant of the CD6 protein does not include insertions compared to the naturally occurring CD6 protein. In some cases, a variant or mutant of the CD6 protein includes substitutions that are conservative substitutions compared to the naturally occurring CD6 protein. In some cases, CD6 is the protein identified by the NCBI sequence reference NP_006716.3 or an isoform or naturally occurring mutant or variant thereof. In some cases, CD6 is the protein as identified by the NCBI sequence reference NP_001241679.1 or an isoform or naturally occurring mutant or variant thereof. In some cases, CD6 is the protein as identified by the NCBI sequence reference NP_001241680.1 or an isoform or naturally occurring mutant or variant thereof. Non-limiting examples of human CD6 amino acid sequences available under NCBI sequence references are as follows:

NP_006716.3
(SEQ ID NO: 1)
MWLFFGITGLLTAALSGHPSPAPPDQLNTSSAESELWEPGERLPVRLTN

GSSSCSGTVEVRLEASWEPACGALWDSRAAEAVCRALGCGGAEAASQLA

PPTPELPPPPAAGNTSVAANATLAGAPALLCSGAEWRLCEVVEHACRSD

GRRARVTCAENRALRLVDGGGACAGRVEMLEHGEWGSVCDDTWDLEDAH

VVCRQLGCGWAVQALPGLHFTPGRGPIHRDQVNCSGAEAYLWDCPGLPG

QHYCGHKEDAGAVCSEHQSWRLTGGADRCEGQVEVHFRGVWNTVCDSEW

YPSEAKVLCQSLGCGTAVERPKGLPHSLSGRMYYSCNGEELTLSNCSWR

FNNSNLCSQSLAARVLCSASRSLHNLSTPEVPASVQTVTIESSVTVKIE

NKESRELMLLIPSIVLGILLLGSLIFIAFILLRIKGKYALPVMVNHQHL

PTTIPAGSNSYQPVPITIPKEVFMLPIQVQAPPPEDSDSGSDSDYEHYD

FSAQPPVALTTFYNSQRHRVTDEEVQQSRFQMPPLEEGLEELHASHIPT

ANPGHCITDPPSLGPQYHPRSNSESSTSSGEDYCNSPKSKLPPWNPQVF

SSERSSFLEQPPNLELAGTQPAFSAGPPADDSSSTSSGEWYQNFQPPPQ

PPSEEQFGCPGSPSPQPDSTDNDDYDDISAA

NP_001241679.1
(SEQ ID NO: 2)
MWLFFGITGLLTAALSGHPSPAPPDQLNTSSAESELWEPGERLPVRLTN

GSSSCSGTVEVRLEASWEPACGALWDSRAAEAVCRALGCGGAEAASQLA

PPTPELPPPPAAGNTSVAANATLAGAPALLCSGAEWRLCEVVEHACRSD

GRRARVTCAENRALRLVDGGGACAGRVEMLEHGEWGSVCDDTWDLEDAH

VVCRQLGCGWAVQALPGLHFTPGRGPIHRDQVNCSGAEAYLWDCPGLPG

QHYCGHKEDAGAVCSEHQSWRLTGGADRCEGQVEVHFRGVWNTVCDSEW

YPSEAKVLCQSLGCGTAVERPKGLPHSLSGRMYYSCNGEELTLSNCSWR

FNNSNLCSQSLAARVLCSASRSLHNLSTPEVPASVQTVTIESSVTVKIE

NKESRELMLLIPSIVLGILLLGSLIFIAFILLRIKGKYVFMLPIQVQAP

PPEDSDSGSDSDYEHYDFSAQPPVALTTFYNSQRHRVTDEEVQQSRFQM

PPLEEGLEELHASHIPTANPGHCITDPPSLGPQYHPRSNSESSTSSGED

YCNSPKSKLPPWNPQVFSSERSSFLEQPPNLELAGTQPAFSGSPSPQPD

STDNDDYDDISAA

NP_001241680.1
(SEQ ID NO: 3)
MWLFFGITGLLTAALSGHPSPAPPDQLNTSSAESELWEPGERLPVRLTN

GSSSCSGTVEVRLEASWEPACGALWDSRAAEAVCRALGCGGAEAASQLA

PPTPELPPPPAAGNTSVAANATLAGAPALLCSGAEWRLCEVVEHACRSD

GRRARVTCAENRALRLVDGGGACAGRVEMLEHGEWGSVCDDTWDLEDAH

VVCRQLGCGWAVQALPGLHFTPGRGPIHRDQVNCSGAEAYLWDCPGLPG

QHYCGHKEDAGAVCSEHQSWRLTGGADRCEGQVEVHFRGVWNTVCDSEW

YPSEAKVLCQSLGCGTAVERPKGLPHSLSGRMYYSCNGEELTLSNCSWR

FNNSNLCSQSLAARVLCSASRSLHNLSTPEVPASVQTVTIESSVTVKIE

```
NKESRELMLLIPSIVLGILLLGSLIFIAFILLRIKGKYALPVMVNHQHL

PTTIPAGSNSYQPVPITIPKEDSQRHRVTDEEVQQSRFQMPPLEEGLEE

LHASHIPTANPGHCITDPPSLGPQYHPRSNSESSTSSGEDYCNSPKSKL

PPWNPQVFSSERSSFLEQPPNLELAGTQPAFSGSPSPQPDSTDNDDYDD

ISAA
```

The term "CD28 transmembrane domain" as provided herein includes any of the recombinant or naturally-occurring forms of the transmembrane domain of CD28, or variants or homologs thereof that maintain CD28 transmembrane domain activity (e.g. within at least 50%, 80%, 90%, 95%, 96%, 97%, 98%, 99% or 100% activity compared to the CD28 transmembrane domain). In some cases, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD28 transmembrane domain polypeptide. In some cases, the CD28 transmembrane domain is a human CD28 transmembrane domain protein. In some cases, a variant or mutant of the CD28 transmembrane domain protein includes no more than 5, 4, 3, 2, or 1 deletions compared to the naturally occurring CD28 transmembrane domain protein. In some cases, a variant or mutant of the CD28 transmembrane domain protein includes no more than 5, 4, 3, 2, or 1 insertions compared to the naturally occurring CD28 transmembrane domain protein. In some cases, a variant or mutant of the CD28 transmembrane domain protein does not include deletions compared to the naturally occurring CD28 transmembrane domain protein. In some cases, a variant or mutant of the CD28 transmembrane domain protein does not include insertions compared to the naturally occurring CD28 transmembrane domain protein. In some cases, In some cases, a variant or mutant of the CD28 transmembrane domain protein includes substitutions that are conservative substitutions compared to the naturally occurring CD28 transmembrane domain protein. In some cases, In some cases, the CD28 transmembrane domain includes all or a portion of the protein as identified by NCBI sequence reference NP_001230006.1, or an isoform or naturally occurring mutant or variant thereof. In some cases, In some cases, the CD28 transmembrane domain includes all or a portions of the protein as identified by the NCBI sequence reference NP_001230007.1, or an isoform or naturally occurring mutant or variant thereof. In some cases, In some cases, the CD28 transmembrane domain includes all or a portion of the protein as identified by the NCBI sequence reference NP_006130.1, or an isoform or naturally occurring mutant or variant thereof. In some cases, In some cases, the CD28 transmembrane domain amino acid sequence includes the sequence of RSKRSRGGHSDYMNMTPRRPGPTRKHYQPYAPPRDFAAYRS (SEQ ID NO:7). In some cases, In some cases, the CD28 transmembrane domain amino acid sequence is the sequence of SEQ ID NO:7. In some cases, the CD28 transmembrane domain amino acid sequence includes the sequence of RSKRSRLLHSDYMNMTPRRPGPTRKHYQPYAPPRDFAAYRS (SEQ ID NO:8). In some cases, the CD28 transmembrane domain amino acid sequence is the sequence of SEQ ID NO:8. Non-limiting examples of human CD28 amino acid sequences available under NCBI sequence references are as follows:

```
NP_001230006.1
                                           (SEQ ID NO: 4)
MLRLLLALNLFPSIQVTGNKILVKQSPMLVAYDNAVNLSWKHLCPSPLF

PGPSKPFWVLVVVGGVLACYSLLVTVAFIIFWVRSKRSRLLHSDYMNMT

PRRPGPTRKHYQPYAPPRDFAAYRS

NP_001230007.1
                                           (SEQ ID NO: 5)
MLRLLLALNLFPSIQVTGKHLCPSPLFPGPSKPFWVLVVVGGVLACYSL

LVTVAFIIFWVRSKRSRLLHSDYMNMTPRRPGPTRKHYQPYAPPRDFAA

YRS

NP_006130.1
                                           (SEQ ID NO: 6)
MLRLLLALNLFPSIQVTGNKILVKQSPMLVAYDNAVNLSCKYSYNLFSR

EFRASLHKGLDSAVEVCVVYGNYSQQLQVYSKTGFNCDGKLGNESVTFY

LQNLYVNQTDIYFCKIEVMYPPPYLDNEKSNGTIIHVKGKHLCPSPLFP

GPSKPFWVLVVVGGVLACYSLLVTVAFIIFWVRSKRSRLLHSDYNINMT

PRRPGPTRKHYQPYAPPRDFAAYRS
```

In some cases, the CD28 transmembrane domain is encoded by all or a portion of the nucleic acid sequence identified by the NCBI sequence reference NM_001243077.1, or an isoform or naturally occurring mutant or variant thereof. In some cases, the CD28 transmembrane domain is encoded by all or a portion the nucleic acid sequence identified by the NCBI sequence reference NM_001243078.1, or an isoform or naturally occurring mutant or variant thereof. In some cases, the CD28 transmembrane domain is encoded by all of a portion of the nucleic acid sequence identified by the NCBI sequence reference NM_006139.3, or an isoform or naturally occurring mutant or variant thereof. In some cases, a variant or mutant of the CD28 transmembrane domain nucleic acid sequence includes no more than 5, 4, 3, 2, or 1 deletions compared to the naturally occurring CD28 transmembrane domain nucleic acid sequence. In some cases, a variant or mutant of the CD28 transmembrane domain nucleic acid sequence includes no more than 5, 4, 3, 2, or 1 insertions compared to the naturally occurring CD28 transmembrane domain nucleic acid sequence. In some cases, a variant or mutant of the CD28 transmembrane domain nucleic acid sequence does not include deletions compared to the naturally occurring CD28 transmembrane domain nucleic acid sequence. In some cases, a variant or mutant of the CD28 transmembrane domain nucleic acid sequence does not include insertions compared to the naturally occurring CD28 transmembrane domain nucleic acid sequence. In some cases, a variant or mutant of the CD28 transmembrane domain nucleic acid sequence includes substitutions that are conservative substitutions compared to the naturally occurring CD28 transmembrane domain nucleic acid sequence.

The term "CD4 transmembrane domain" as provided herein includes any of the recombinant or naturally-occurring forms of the transmembrane domain of CD4, or variants or homologs thereof that maintain CD4 transmembrane domain activity (e.g. within at least 50%, 80%, 90%, 95%, 96%, 97%, 98%, 99% or 100% activity compared to the CD4 transmembrane domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD4 transmembrane domain polypeptide. In some cases, the CD4 transmembrane domain amino acid sequence includes the sequence of MALIVLGGVAGLLLFIGLGIFF (SEQ ID NO:23). In some cases, the CD4 transmembrane domain amino acid sequence is the sequence of SEQ ID NO:23. A non-limiting example of a nucleotide sequence that encodes the CD4 transmembrane domain is ATGGCCCTGAT-TGTGCTGGGGGGCGTCGCCGGCCTCCTGCTTTT-CATTGGGCTAGGCAT CTTCTTC (SEQ ID NO:24). In some cases, the CD4 transmembrane domain is a human CD4 transmembrane domain protein. In some cases, a variant or mutant of the CD4 transmembrane domain protein includes no more than 5, 4, 3, 2, or 1 deletions compared to the naturally occurring CD4 transmembrane domain protein. In some cases, a variant or mutant of the CD4 transmembrane domain protein includes no more than 5, 4, 3, 2, or 1 insertions compared to the naturally occurring CD4 transmembrane domain protein. In some cases, a variant or mutant of the CD4 transmembrane domain protein does not include deletions compared to the naturally occurring CD4 transmembrane domain protein. In some cases, a variant or mutant of the CD4 transmembrane domain protein does not include insertions compared to the naturally occurring CD4 transmembrane domain protein. In some cases, a variant or mutant of the CD4 transmembrane domain protein includes substitutions that are conservative substitutions compared to the naturally occurring CD4 transmembrane domain protein. In some cases, the CD4 transmembrane domain includes all or a portion of the protein identified by the NCBI sequence reference NP_000607.1, or an isoform or naturally occurring mutant or variant thereof. In some cases, the CD4 transmembrane domain includes all or a portion of the protein identified by the NCBI sequence reference NP_001181943.1, or an isoform or naturally occurring mutant or variant thereof. In some cases, the CD4 transmembrane domain includes all or a portion of the protein identified by the NCBI sequence reference NP_001181944.1, or an isoform or naturally occurring mutant or variant thereof. In some cases, the CD4 transmembrane domain includes all or a portion of the protein identified by the NCBI sequence reference NP_001181945.1, or an isoform or naturally occurring mutant or variant thereof. In some cases, the CD4 transmembrane domain includes all or a portion of the protein identified by the NCBI sequence reference NP_001181946.1, or an isoform or naturally occurring mutant or variant thereof. Non-limiting examples of human CD4 amino acid sequences available under NCBI sequence references are as follows:

NP_000607.1
(SEQ ID NO: 9)
MNRGVPFRHLLLVLQLALLPAATQGKKVVLGKKGDTVELTCTASQKKSI

QFHWKNSNQIKILGNQGSFLTKGPSKLNDRADSRRSLWDQGNFPLIIKN

LKIEDSDTYICEVEDQKEEVQLLVFGLTANSDTHLLQGQSLTLTLESPP

GSSPSVQCRSPRGKNIQGGKTLSVSQLELQDSGTWTCTVLQNQKKVEFK

IDIVVLAFQKASSIVYKKEGEQVEFSFPLAFTVEKLTGSGELWWQAERA

SSSKSWITFDLKNKEVSVKRVTQDPKLQMGKKLPLHLTLPQALPQYAGS

GNLTLALEAKTGKLHQEVNLVVMRATQLQKNLTCEVWGPTSPKLMLSLK

LENKEAKVSKREKAVWVLNPEAGMWQCLLSDSGQVLLESNIKVLPTWST

-continued

PVQPMALIVLGGVAGLLLFIGLGIFFCVRCRHRRRQAERMSQIKRLLSE

KKTCQCPHRFQKTCSPI

NP_001181943.1
(SEQ ID NO: 10)
NIPTPLVHPHLPISSPRVSPFPPPAFQKASSIVYKKEGEQVEFSFPLAF

TVEKLTGSGELWWQAERASSSKSWITFDLKNKEVSVKRVTQDPKLQMGK

KLPLHLTLPQALPQYAGSGNLTLALEAKTGKLHQEVNLVVMRATQLQKN

LTCEVWGPTSPKLMLSLKLENKEAKVSKREKAVWVLNPEAGMWQCLLSD

SGQVLLESNIKVLPTWSTPVQPMALIVLGGVAGLLLFIGLGIFFCVRCR

HRRRQAERMSQIKRLLSEKKTCQCPHRFQKTCSPI

NP_001181944.1
(SEQ ID NO: 11)
MGKKLPLHLTLPQALPQYAGSGNLTLALEAKTGKLHQEVNLVVMRATQL

QKNLTCEVWGPTSPKLMLSLKLENKEAKVSKREKAVWVLNPEAGMWQCL

LSDSGQVLLESNIKVLPTWSTPVQPMALIVLGGVAGLLLFIGLGIFFCV

RCRHRRRQAERMSQIKRLLSEKKTCQCPHRFQKTCSPI

NP_001181945.1
(SEQ ID NO: 12)
MGKKLPLHLTLPQALPQYAGSGNLTLALEAKTGKLHQEVNLVVMRATQL

QKNLTCEVWGPTSPKLMLSLKLENKEAKVSKREKAVWVLNPEAGMWQCL

LSDSGQVLLESNIKVLPTWSTPVQPMALIVLGGVAGLLLFIGLGIFFCV

RCRHRRRQAERMSQIKRLLSEKKTCQCPHRFQKTCSPI

NP_001181946.1
(SEQ ID NO: 13)
MGKKLPLHLTLPQALPQYAGSGNLTLALEAKTGKLHQEVNLVVMRATQL

QKNLTCEVWGPTSPKLMLSLKLENKEAKVSKREKAVWVLNPEAGMWQCL

LSDSGQVLLESNIKVLPTWSTPVQPMALIVLGGVAGLLLFIGLGIFFCV

RCRHRRRQAERMSQIKRLLSEKKTCQCPHRFQKTCSPI

In some cases, the CD4 transmembrane domain is encoded by all or a portion of the nucleic acid sequence identified by the NCBI sequence reference NM_000616.4, or an isoform or naturally occurring mutant or variant thereof. In some cases, the CD4 transmembrane domain is encoded by all or a portion of the nucleic acid sequence identified by the NCBI sequence reference NM_001195014.2, or an isoform or naturally occurring mutant or variant thereof. In some cases, the CD4 transmembrane domain is encoded by all or a portion of the nucleic acid sequence identified by the NCBI sequence reference NM_001195015.2, or an isoform or naturally occurring mutant or variant thereof. In some cases, the CD4 transmembrane domain is encoded by all or a portion of the nucleic acid sequence identified by the NCBI sequence reference NM_001195016.2, or an isoform or naturally occurring mutant or variant thereof. In some cases, the CD4 transmembrane domain is encoded by all or a portion of the nucleic acid sequence identified by the NCBI sequence reference NM_001195017.2, or an isoform or naturally occurring mutant or variant thereof. In some cases, a variant or mutant of the CD4 transmembrane domain nucleic acid sequence includes no more than 5, 4, 3, 2, or 1 deletions compared to the naturally occurring CD4 transmembrane domain nucleic acid sequence. In some cases, a variant or mutant of the CD4 transmembrane domain nucleic acid sequence includes no more than 5, 4, 3, 2, or 1 insertions compared to the naturally occurring CD4 transmembrane domain nucleic acid sequence. In some cases, a variant or mutant of the CD4 transmembrane domain nucleic acid sequence does not include deletions compared to the naturally occurring CD4 transmembrane domain nucleic acid sequence. In some cases, a variant or mutant of the CD4 transmembrane domain nucleic acid sequence does not include insertions compared to the naturally occurring CD4 transmembrane domain nucleic acid sequence. In some cases, a variant or mutant of the CD4 transmembrane domain nucleic acid sequence includes substitutions that are conservative substitutions compared to the naturally occurring CD4 transmembrane domain nucleic acid sequence.

The term "CD8 transmembrane domain" as provided herein includes any of the recombinant or naturally-occurring forms of the transmembrane domain of CD8, or variants or homologs thereof that maintain CD8 transmembrane domain activity (e.g. within at least 50%, 80%, 90%, 95%, 96%, 97%, 98%, 99% or 100% activity compared to the CD8 transmembrane domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD8 transmembrane domain polypeptide. In some cases, the CD8 transmembrane domain amino acid sequenceincludes the sequence of IYIWAPLAGTCGVLLLSLVIT (SEQ ID NO:25). In some cases, the CD8 transmembrane domain amino acid sequence is the sequence of SEQ ID NO:25. In some cases, the CD8 transmembrane domain is CD8A transmembrane domain. In some cases, the CD8 transmembrane domain is a CD8B transmembrane domain. In some cases, the CD8 transmembrane domain is a human CD8 transmembrane domain protein. In some cases, a variant or mutant of the CD8 transmembrane domain protein includes no more than 5, 4, 3, 2, or 1 deletions compared to the naturally occurring CD8 transmembrane domain protein. In some cases, a variant or mutant of the CD8 transmembrane domain protein includes no more than 5, 4, 3, 2, or 1 insertions compared to the naturally occurring CD8 transmembrane domain protein. In some cases, a variant or mutant of the CD8 transmembrane domain protein does not include deletions compared to the naturally occurring CD8 transmembrane domain protein. In some cases, a variant or mutant of the CD8 transmembrane domain protein does not include insertions compared to the naturally occurring CD8 transmembrane domain protein. In some cases, a variant or mutant of the CD8 transmembrane domain protein includes substitutions that are conservative substitutions compared to the naturally occurring CD8 transmembrane domain protein. In some cases, the CD8 transmembrane domain includes all or a portion of the protein identified by the NCBI sequence reference NP_001139345.1, or an isoform or naturally occurring mutant or variant thereof. In some cases, the CD8 transmembrane domain includes all or a portion of the protein identified by the NCBI sequence reference NP_001181943.1, or an isoform or naturally occurring mutant or variant thereof. In some cases, the CD8 transmembrane domain includes all or a portion of the protein identified by the NCBI sequence reference NP_001181944.1, or an isoform or naturally occurring mutant or variant thereof. In some cases, the CD8 transmembrane domain includes all or a portion of the protein identified by the NCBI sequence reference NP_001181945.1, or an isoform or naturally occurring mutant or variant thereof. In some cases, the CD8 transmembrane domain includes all or a portion of the protein identified by the NCBI sequence reference NP_741969.1, or an isoform or naturally occurring mutant or variant thereof. In some cases, the CD8 transmembrane domain includes all or a portion of the protein identified by the NCBI sequence reference NP_001759.3, or an isoform or naturally occurring mutant or variant thereof. In some cases, the CD8 transmembrane domain includes all or a portion of the protein identified by the NCBI sequence reference XP_011531466.1, or an isoform or naturally occurring mutant or variant thereof. In some cases, the CD8 transmembrane domain includes all or a portion of the protein identified by the NCBI sequence reference NP_001171571.1, or an isoform or naturally occurring mutant or variant thereof. In some cases, the CD8 transmembrane domain includes all or a portion of the protein identified by the NCBI sequence reference NP_757362.1, or an isoform or naturally occurring mutant or variant thereof. In some cases, the CD8 transmembrane domain includes all or a portion of the protein identified by the NCBI sequence reference NP_742100.1, or an isoform or naturally occurring mutant or variant thereof. In some cases, the CD8 transmembrane domain includes all or a portion of the protein identified by the NCBI sequence reference NP_742099.1, or an isoform or naturally occurring mutant or variant thereof. In some cases, the CD8 transmembrane domain includes all or a portion of the protein identified by the NCBI sequence reference NP_004922.1, or an isoform or naturally occurring mutant or variant thereof. Non-limiting examples of human CD8 amino acid sequences available under NCBI sequence references are as follows:

```
NP_001139345.1
                                         (SEQ ID NO: 46)
MALPVTALLLPLALLLHAARPSQFRVSPLDRTWNLGETVELKCQVLLSN

PTSGCSWLFQPRGAAASPTFLLYLSQNKPKAAEGLDTQRFSGKRLGDTF

VLTLSDFRRENEGYYFCSALSNSIMYFSHFVPVFLPAKPTTTPAPRPPT

PAPTIASQPLSLRPEACRPAAGGAVHTRGLDFACDIYIWAPLAGTCGVL

LLSLVITLYCNHRNRRRVCKCPRPVVKSGDKPSLSARYV

NP_741969.1
                                         (SEQ ID NO: 47)
MALPVTALLLPLALLLHAARPSQFRVSPLDRTWNLGETVELKCQVLLSN

PTSGCSWLFQPRGAAASPTFLLYLSQNKPKAAEGLDTQRFSGKRLGDTF

VLTLSDFRRENEGYYFCSALSNSIIVIYFSHFVPVFLPAKPTTTPAPRP

PTPAPTIASQPLSLRPEACRPAAGGAGNRRRVCKCPRPVVKSGDKPSLS

ARYV

NP_001759.3
                                         (SEQ ID NO: 48)
MALPVTALLLPLALLLHAARPSQFRVSPLDRTWNLGETVELKCQVLLSN

PTSGCSWLFQPRGAAASPTFLLYLSQNKPKAAEGLDTQRFSGKRLGDTF

VLTLSDFRRENEGYYFCSALSNSIMYFSHFVPVFLPAKPTTTPAPRPPT

PAPTIASQPLSLRPEACRPAAGGAVHTRGLDFACDIYIWAPLAGTCGVL

LLSLVITLYCNHRNRRRVCKCPRPVVKSGDKPSLSARYV

XP_011531466.1
                                         (SEQ ID NO: 49)
MRPRLWLLLAAQLTVLHGNSVLQQTPAYIKVQTNKMVMLSCEAKISLSN

MRIYWLRQRQAPSSDSHHEFLALWDSAKGTIHGEEVEQEKIAVFRDASR
```

-continued

FILNLTSVKPEDSGIYFCMIVGSPELTFGKGTQLSVVDFLPTTAQPTKK

STLKKRVCRLPRPETQKGPLCSPITLGLLVAGVLVLLVSLGVAIHLCCR

RRRARLRFMKQKFNIVCLKISGFTTCCCFQILQMSREYGFGVLLQKDIG

Q

NP_001171571.1
(SEQ ID NO: 50)
MRPRLWLLLAAQLTVLHGNSVLQQTPAYIKVQTNKMVMLSCEAKISLSN

MRIYWLRQRQAPSSDSHHEFLALWDSAKGTIHGEEVEQEKIAVFRDASR

FILNLTSVKPEDSGIYFCMIVGSPELTFGKGTQLSVVDFLPTTAQPTKK

STLKKRVCRLPRPETQKGLKGKVYQEPLSPNACMDTTAILQPHRSCLTH

GS

NP_757362.1
(SEQ ID NO: 51)
MRPRLWLLLAAQLTVLHGNSVLQQTPAYIKVQTNKMVMLSCEAKISLSN

MRIYWLRQRQAPSSDSHHEFLALWDSAKGTIHGEEVEQEKIAVFRDASR

FILNLTSVKPEDSGIYFCMIVGSPELTFGKGTQLSVVDFLPTTAQPTKK

STLKKRVCRLPRPETQKGPLCSPITLGLLVAGVLVLLVSLGVAIHLCCR

RRRARLRFMKQPQGEGISGTFVPQCLHGYYSNTTTSQKLLNPWILKT

NP_742100.1
(SEQ ID NO: 52)
MRPRLWLLLAAQLTVLHGNSVLQQTPAYIKVQTNKMVMLSCEAKISLSN

MRIYWLRQRQAPSSDSHHEFLALWDSAKGTIHGEEVEQEKIAVFRDASR

FILNLTSVKPEDSGIYFCMIVGSPELTFGKGTQLSVVDFLPTTAQPTKK

STLKKRVCRLPRPETQKGRRRRARLRFMKQPQGEGISGTFVPQCLHGYY

SNTTTSQKLLNPWILKT

NP_742099.1
(SEQ ID NO: 53)
MRPRLWLLLAAQLTVLHGNSVLQQTPAYIKVQTNKMVMLSCEAKISLSN

MRIYWLRQRQAPSSDSHHEFLALWDSAKGTIHGEEVEQEKIAVFRDASR

FILNLTSVKPEDSGIYFCMIVGSPELTFGKGTQLSVVDFLPTTAQPTKK

STLKKRVCRLPRPETQKGPLCSPITLGLLVAGVLVLLVSLGVAIHLCCR

RRRARLRFMKQLRLHPLEKCSRMDY

NP_004922.1
(SEQ ID NO: 54)
MRPRLWLLLAAQLTVLHGNSVLQQTPAYIKVQTNKMVMLSCEAKISLSN

MRIYWLRQRQAPSSDSHHEFLALWDSAKGTIHGEEVEQEKIAVFRDASR

FILNLTSVKPEDSGIYFCMIVGSPELTFGKGTQLSVVDFLPTTAQPTKK

STLKKRVCRLPRPETQKGPLCSPITLGLLVAGVLVLLVSLGVAIHLCCR

RRRARLRFMKQFYK

In some cases, the CD8 transmembrane domain is encoded by all or a portion of the nucleic acid sequence identified by the NCBI sequence reference NR_027353.1, or an isoform or naturally occurring mutant or variant thereof. In some cases, the CD8 transmembrane domain is encoded by all or a portion of the nucleic acid sequence identified by the NCBI sequence reference NM_001145873.1, or an isoform or naturally occurring mutant or variant thereof. In some cases, the CD8 transmembrane domain is encoded by all or a portion of the nucleic acid sequence identified by the NCBI sequence reference NM_001768.6, or an isoform or naturally occurring mutant or variant thereof. In some cases, the CD8 transmembrane domain is encoded by all or a portion of the nucleic acid sequence identified by the NCBI sequence reference NM_171827.3, or an isoform or naturally occurring mutant or variant thereof. In some cases, the CD8 transmembrane domain is encoded by all or a portion of the nucleic acid sequence identified by the NCBI sequence reference XM_011533164.2, or an isoform or naturally occurring mutant or variant thereof. In some cases, the CD8 transmembrane domain is encoded by all or a portion of the nucleic acid sequence identified by the NCBI sequence reference NM_001178100.1, or an isoform or naturally occurring mutant or variant thereof. In some cases, the CD8 transmembrane domain is encoded by all or a portion of the nucleic acid sequence identified by the NCBI sequence reference NM_004931.4, or an isoform or naturally occurring mutant or variant thereof. In some cases, the CD8 transmembrane domain is encoded by all or a portion of the nucleic acid sequence identified by the NCBI sequence reference NM_172102.3, or an isoform or naturally occurring mutant or variant thereof. In some cases, the CD8 transmembrane domain is encoded by all or a portion of the nucleic acid sequence identified by the NCBI sequence reference NM_172101.3, or an isoform or naturally occurring mutant or variant thereof. In some cases, the CD8 transmembrane domain is encoded by all or a portion of the nucleic acid sequence identified by the NCBI sequence reference NM_172213.3, or an isoform or naturally occurring mutant or variant thereof. In some cases, a variant or mutant of the CD8 transmembrane domain nucleic acid sequence includes no more than 5, 4, 3, 2, or 1 deletions compared to the naturally occurring CD8 transmembrane domain nucleic acid sequence. In some cases, a variant or mutant of the CD8 transmembrane domain nucleic acid sequence includes no more than 5, 4, 3, 2, or 1 insertions compared to the naturally occurring CD8 transmembrane domain nucleic acid sequence. In some cases, a variant or mutant of the CD8 transmembrane domain nucleic acid sequence does not include deletions compared to the naturally occurring CD8 transmembrane domain nucleic acid sequence. In some cases, a variant or mutant of the CD8 transmembrane domain nucleic acid sequence does not include insertions compared to the naturally occurring CD8 transmembrane domain nucleic acid sequence. In some cases, a variant or mutant of the CD8 transmembrane domain nucleic acid sequence includes substitutions that are conservative substitutions compared to the naturally occurring CD8 transmembrane domain nucleic acid sequence.

The term "CD3-zeta transmembrane domain" as provided herein includes any of the recombinant or naturally-occurring forms of the transmembrane domain of CD3-zeta, or variants or homologs thereof that maintain CD3-zeta transmembrane domain activity (e.g. within at least 50%, 80%, 90%, 95%, 96%, 97%, 98%, 99% or 100% activity compared to the CD3-zeta transmembrane domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD3-zeta transmembrane domain polypeptide. In some cases, the CD3-zeta transmembrane domain is a human CD3-zeta transmembrane domain protein. In some cases, a variant or mutant of the CD3-zeta transmembrane domain protein includes no more than 5, 4, 3, 2, or 1 deletions compared to the naturally occurring CD3-zeta transmembrane domain protein. In some cases, a variant or mutant of the CD3-zeta transmembrane domain protein includes no more than 5, 4, 3, 2, or 1 insertions compared to the naturally occurring CD3-zeta transmembrane domain protein. In some cases, a variant or mutant of the CD3-zeta transmembrane domain protein does not include deletions compared to the naturally occurring CD3-zeta transmembrane domain protein. In some cases, a variant or mutant of the CD3-zeta transmembrane domain protein does not include insertions compared to the naturally occurring CD3-zeta transmembrane domain protein. In some cases, a variant or mutant of the CD3-zeta transmembrane domain protein includes substitutions that are conservative substitutions compared to the naturally occurring CD3-zeta transmembrane domain protein. In some cases, the CD3-zeta transmembrane domain includes all or a portion of the protein identified by the NCBI sequence reference NP_000725.1, or an isoform or naturally occurring mutant or variant thereof. In some cases, the CD3-zeta transmembrane domain includes all or a portion of the protein identified by the NCBI sequence reference NP_932170.1, or an isoform or naturally occurring mutant or variant thereof. Non-limiting examples of human CD3-zeta amino acid sequences available under NCBI sequence references are as follows:

NP_000725.1
(SEQ ID NO: 55)
MKWKALFTAAILQAQLPITEAQSFGLLDPKLCYLLDGILFIYGVILTALFL

RVKFSRSADAPAYQQGQNQLYNELNLGRREEYDVLDKRRGRDPEMGGKPRR

KNPQEGLYNELQKDKMAEAYSEIGMKGERRRGKGHDGLYQGLSTATKDTYD

ALHMQALPPR

NP_932170.1
(SEQ ID NO: 56)
MKWKALFTAAILQAQLPITEAQSFGLLDPKLCYLLDGILFIYGVILTALFL

RVKFSRSADAPAYQQGQNQLYNELNLGRREEYDVLDKRRGRDPEMGGKPQR

RKNPQEGLYNELQKDKMAEAYSEIGMKGERRRGKGHDGLYQGLSTATKDTY

DALHMQALPPR

In some cases, the CD3-zeta transmembrane domain is encoded by all or a portion of the nucleic acid sequence identified by the NCBI sequence reference NM_000734.3, or an isoform or naturally occurring mutant or variant thereof. In some cases, the CD3-zeta transmembrane domain is encoded by all or a portion of the nucleic acid sequence identified by the NCBI sequence reference NM_198053.2, or an isoform or naturally occurring mutant or variant thereof. In some cases, a variant or mutant of the CD3-zeta transmembrane domain nucleic acid sequence includes no more than 5, 4, 3, 2, or 1 deletions compared to the naturally occurring CD3-zeta transmembrane domain nucleic acid sequence. In some cases, a variant or mutant of the CD3-zeta transmembrane domain nucleic acid sequence includes no more than 5, 4, 3, 2, or 1 insertions compared to the naturally occurring CD3-zeta transmembrane domain nucleic acid sequence. In some cases, a variant or mutant of the CD3-zeta transmembrane domain nucleic acid sequence does not include deletions compared to the naturally occurring CD3-zeta transmembrane domain nucleic acid sequence. In some cases, a variant or mutant of the CD3-zeta transmembrane domain nucleic acid sequence does not include insertions compared to the naturally occurring CD3-zeta transmembrane domain nucleic acid sequence. In some cases, a variant or mutant of the CD3-zeta transmembrane domain nucleic acid sequence includes substitutions that are conservative substitutions compared to the naturally occurring CD3-zeta transmembrane domain nucleic acid sequence.

The term "CD28 co-stimulatory domain" as provided herein includes any of the recombinant or naturally-occurring forms of the co-stimulatory domain of CD28, or variants or homologs thereof that maintain CD28 co-stimulatory domain activity (e.g. within at least 50%, 80%, 90%, 95%, 96%, 97%, 98%, 99% or 100% activity compared to the CD28 co-stimulatory domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD28 co-stimulatory domain polypeptide. In some cases, the CD28 co-stimulatory domain amino acid sequence includes the sequence of RSKRSRGGHSDYMNMTPRRPGPTRKHYQPYAPPRDFAAYRS (SEQ ID NO:7). In some cases, the CD28 co-stimulatory domain amino acid sequence is the sequence of RSKRSRLLHSDYMNMTPRRPGPTRKHYQPYAPPRDFAAYRS (SEQ ID NO:8).

In some cases, the CD28 co-stimulatory domain is a human CD28 co-stimulatory domain protein. In some cases, a variant or mutant of the CD28 co-stimulatory domain protein includes no more than 5, 4, 3, 2, or 1 deletions compared to the naturally occurring CD28 co-stimulatory domain protein. In some cases, a variant or mutant of the CD28 co-stimulatory domain protein includes no more than 5, 4, 3, 2, or 1 insertions compared to the naturally occurring CD28 co-stimulatory domain protein. In some cases, a variant or mutant of the CD28 co-stimulatory domain protein does not include deletions compared to the naturally occurring CD28 co-stimulatory domain protein. In some cases, a variant or mutant of the CD28 co-stimulatory domain protein does not include insertions compared to the naturally occurring CD28 co-stimulatory domain protein. In some cases, a variant or mutant of the CD28 co-stimulatory domain protein includes substitutions that are conservative substitutions compared to the naturally occurring CD28 co-stimulatory domain protein. In some cases, the CD28 co-stimulatory domain includes all or a portion of the protein identified by the NCBI sequence reference NP_001230006.1, or an isoform or naturally occurring mutant or variant thereof. In some cases, the CD28 co-stimulatory domain includes all or a portion of the protein identified by the NCBI sequence reference NP_001230007.1, or an isoform or naturally occurring mutant or variant thereof. In some cases, the CD28 co-stimulatory domain includes all or a portion of the protein identified by the NCBI sequence reference NP_006130.1, or an isoform or naturally occurring mutant or variant thereof. Non-limiting examples of human CD28 amino acid sequences available under NCBI sequence references are as follows:

NP_001230006.1
(SEQ ID NO: 57)
MLRLLLALNLFPSIQVTGNKILVKQSPMLVAYDNAVNLSWKHLCPSPLFPG

PSKPFWVLVVVGGVLACYSLLVTVAFIIFWVRSKRSRLLHSDYMNMTPRRP

GPTRKHYQPYAPPRDFAAYRS

```
NP_001230007.1
                                              (SEQ ID NO: 58)
MLRLLLALNLFPSIQVTGKHLCPSPLFPGPSKPFWVLVVVGGVLACYSLLV

TVAFIIFWVRSKRSRLLHSDYMNMTPRRPGPTRKHYQPYAPPRDFAAYRS

NP_006130.1
                                              (SEQ ID NO: 59)
MLRLLLALNLFPSIQVTGNKILVKQSPMLVAYDNAVNLSCKYSYNLFSREF

RASLHKGLDSAVEVCVVYGNYSQQLQVYSKTGFNCDGKLGNESVTFYLQNL

YVNQTDIYFCKIEVMYPPPYLDNEKSNGTIIHVKGKHLCPSPLFPGPSKPF

WVLVVVGGVLACYSLLVTVAFIIFWVRSKRSRLLHSDYMNMTPRRPGPTRK

HYQPYAPPRDFAAYRS
```

In some cases, the CD28 co-stimulatory domain is encoded by all or a portion of the nucleic acid sequence identified by the NCBI sequence reference NM_001243077.1, or an isoform or naturally occurring mutant or variant thereof. In some cases, the CD28 co-stimulatory domain is encoded by all or a portion of the nucleic acid sequence identified by the NCBI sequence reference NM_001243078.1, or an isoform or naturally occurring mutant or variant thereof. In some cases, the CD28 co-stimulatory domain is encoded by all or a portion of the nucleic acid sequence identified by the NCBI sequence reference NM_006139.3, or an isoform or naturally occurring mutant or variant thereof. In some cases, a variant or mutant of the CD28 co-stimulatory domain nucleic acid sequence includes no more than 5, 4, 3, 2, or 1 deletions compared to the naturally occurring CD28 co-stimulatory domain nucleic acid sequence. In some cases, a variant or mutant of the CD28 co-stimulatory domain nucleic acid sequence includes no more than 5, 4, 3, 2, or 1 insertions compared to the naturally occurring CD28 transmembrane domain nucleic acid sequence. In some cases, a variant or mutant of the CD28 co-stimulatory domain nucleic acid sequence does not include deletions compared to the naturally occurring CD28 co-stimulatory domain nucleic acid sequence. In some cases, a variant or mutant of the CD28 co-stimulatory domain nucleic acid sequence does not include insertions compared to the naturally occurring CD28 co-stimulatory domain nucleic acid sequence. In some cases, a variant or mutant of the CD28 co-stimulatory domain nucleic acid sequence includes substitutions that are conservative substitutions compared to the naturally occurring CD28 co-stimulatory domain nucleic acid sequence.

The term "4-1BB co-stimulatory domain" as provided herein includes any of the recombinant or naturally-occurring forms of the co-stimulatory domain of 4-1BB, or variants or homologs thereof that maintain 4-1BB co-stimulatory domain activity (e.g. within at least 50%, 80%, 90%, 95%, 96%, 97%, 98%, 99% or 100% activity compared to the 4-1BB co-stimulatory domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring 4-1BB co-stimulatory domain polypeptide. In some cases, the 4-1BB co-stimulatory domain is a human 4-1BB co-stimulatory domain protein. In some cases, a variant or mutant of the 4-1BB co-stimulatory domain protein includes no more than 5, 4, 3, 2, or 1 deletions compared to the naturally occurring 4-1BB co-stimulatory domain protein. In some cases, a variant or mutant of the 4-1BB co-stimulatory domain protein includes no more than 5, 4, 3, 2, or 1 insertions compared to the naturally occurring 4-1BB co-stimulatory domain protein. In some cases, a variant or mutant of the 4-1BB co-stimulatory domain protein does not include deletions compared to the naturally occurring 4-1BB co-stimulatory domain protein. In some cases, a variant or mutant of the 4-1BB co-stimulatory domain protein does not include insertions compared to the naturally occurring 4-1BB co-stimulatory domain protein. In some cases, a variant or mutant of the 4-1BB co-stimulatory domain protein includes substitutions that are conservative substitutions compared to the naturally occurring 4-1BB co-stimulatory domain protein. In some cases, the 4-1BB co-stimulatory domain protein includes the amino acid sequence KRGRKKLLYIFKQPFMRPVQTTQEEDGCSCRFPEEEEGGCEL (SEQ ID NO:14). In some cases, the 4-1BB co-stimulatory domain protein amino acid sequence has at least or about 50%, 60%, 70%, 75%, 80%, 85%, 90%, 91%, 92%, 93%, 94%, 95%, 96%, 97%, 98%, or 99% sequence identify to SEQ ID NO:14. In some cases, the 4-1BB co-stimulatory domain includes all or a portion of the protein identified by the NCBI sequence reference NP_001552.2 or an isoform or naturally occurring mutant or variant thereof. Non-limiting examples of human 4-1BB amino acid sequences available under NCBI sequence references are as follows:

```
NP_001552.2
                                              (SEQ ID NO: 15)
MGNSCYNIVATLLLVLNFERTRSLQDPCSNCPAGTFCDNNRNQICSPCPP

NSFSSAGGQRTCDICRQCKGVFRTRKECSSTSNAECDCTPGFHCLGAGCS

MCEQDCKQGQELTKKGCKDCCFGTFNDQKRGICRPWTNCSLDGKSVLVNG

TKERDVVCGPSPADLSPGASSVTPPAPAREPGHSPQIISFFLALTSTALL

FLLFFLTLRFSVVKRGRKKLLYIFKQPFMRPVQTTQEEDGCSCRFPEEEE

GGCEL
```

In some cases, the 4-1BB co-stimulatory domain is encoded by all or a portion of the nucleic acid sequence identified by the NCBI sequence reference NM_001561.5 or an isoform or naturally occurring mutant or variant thereof. In some cases, a variant or mutant of the 4-1BB co-stimulatory domain nucleic acid sequence includes no more than 5, 4, 3, 2, or 1 deletions compared to the naturally occurring 4-1BB co-stimulatory domain nucleic acid sequence. In some cases, a variant or mutant of the 4-1BB co-stimulatory domain nucleic acid sequence includes no more than 5, 4, 3, 2, or 1 insertions compared to the naturally occurring 4-1BB co-stimulatory domain nucleic acid sequence. In some cases, a variant or mutant of the 4-1BB co-stimulatory domain nucleic acid sequence does not include deletions compared to the naturally occurring 4-1BB co-stimulatory domain nucleic acid sequence. In some cases, a variant or mutant of the 4-1BB co-stimulatory domain nucleic acid sequence does not include insertions compared to the naturally occurring 4-1BB co-stimulatory domain nucleic acid sequence. In some cases, a variant or mutant of the 4-1BB co-stimulatory domain nucleic acid sequence includes substitutions that are conservative substitutions compared to the naturally occurring 4-1BB co-stimulatory domain nucleic acid sequence.

The term "ICOS co-stimulatory domain" as provided herein includes any of the recombinant or naturally-occurring forms of the co-stimulatory domain of ICOS, or variants or homologs thereof that maintain ICOS co-stimulatory domain activity (e.g. within at least 50%, 80%, 90%, 95%, 96%, 97%, 98%, 99% or 100% activity compared to the ICOS co-stimulatory domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring ICOS co-stimulatory domain polypeptide. In some cases, the ICOS co-stimulatory domain amino acid sequence includes the sequence of CWLTKKKYSSSVHDPNGEYMFMRAVN-TAKKSRLTDVTL (SEQ ID NO:31). In some cases, the ICOS co-stimulatory domain is a human ICOS co-stimulatory domain protein. In some cases, a variant or mutant of the ICOS co-stimulatory domain protein includes no more than 5, 4, 3, 2, or 1 deletions compared to the naturally occurring ICOS co-stimulatory domain protein. In some cases, a variant or mutant of the ICOS co-stimulatory domain protein includes no more than 5, 4, 3, 2, or 1 insertions compared to the naturally occurring ICOS co-stimulatory domain protein. In some cases, a variant or mutant of the ICOS co-stimulatory domain protein does not include deletions compared to the naturally occurring ICOS co-stimulatory domain protein. In some cases, a variant or mutant of the ICOS co-stimulatory domain protein does not include insertions compared to the naturally occurring ICOS co-stimulatory domain protein. In some cases, a variant or mutant of the ICOS co-stimulatory domain protein includes substitutions that are conservative substitutions compared to the naturally occurring ICOS co-stimulatory domain protein. In some cases, the ICOS co-stimulatory domain includes all or a portion of the protein identified by the NCBI sequence reference NP_036224.1, or an isoform or naturally occurring mutant or variant thereof. Non-limiting examples of human ICOS amino acid sequences available under NCBI sequence references are as follows:

```
NP_036224.1
                                        (SEQ ID NO: 16)
MKSGLWYFFLFCLRIKVLTGEINGSANYEMFIFHNGGVQILCKYPDIVQ

QFKMQLLKGGQILCDLTKTKGSGNTVSIKSLKFCHSQLSNNSVSFFLYN

LDHSHANYYFCNLSIFDPPPFKVTLTGGYLHIYESQLCCQLKFWLPIGC

AAFVVVCILGCILICWLTKKKYSSSVHDPNGEYMFMRAVNTAKKSRLTD

VTL
```

In some cases, the ICOS co-stimulatory domain is encoded by all or a portion of the nucleic acid sequence identified by the NCBI sequence reference NM_012092.3, or an isoform or naturally occurring mutant or variant thereof. In some cases, a variant or mutant of the ICOS co-stimulatory domain nucleic acid sequence includes no more than 5, 4, 3, 2, or 1 deletions compared to the naturally occurring ICOS co-stimulatory domain nucleic acid sequence. In some cases, a variant or mutant of the ICOS co-stimulatory domain nucleic acid sequence includes no more than 5, 4, 3, 2, or 1 insertions compared to the naturally occurring ICOS co-stimulatory domain nucleic acid sequence. In some cases, a variant or mutant of the ICOS co-stimulatory domain nucleic acid sequence does not include deletions compared to the naturally occurring ICOS co-stimulatory domain nucleic acid sequence. In some cases, a variant or mutant of the ICOS co-stimulatory domain nucleic acid sequence does not include insertions compared to the naturally occurring ICOS co-stimulatory domain nucleic acid sequence. In some cases, a variant or mutant of the ICOS co-stimulatory domain nucleic acid sequence includes substitutions that are conservative substitutions compared to the naturally occurring ICOS co-stimulatory domain nucleic acid sequence.

The term "OX-40 co-stimulatory domain" as provided herein includes any of the recombinant or naturally-occurring forms of the co-stimulatory domain of OX-40, or variants or homologs thereof that maintain OX-40 co-stimulatory domain activity (e.g. within at least 50%, 80%, 90%, 95%, 96%, 97%, 98%, 99% or 100% activity compared to the OX-40 co-stimulatory domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring OX-40 co-stimulatory domain polypeptide. In some cases, the OX-40 co-stimulatory domain amino acid sequence includes the sequence of ALYLLRRDQRLPPDAHKPPGGGSFRTPIQEEQADAH-STLAKI (SEQ ID NO:32). In some cases, the OX-40 co-stimulatory domain is a human OX-40 co-stimulatory domain protein. In some cases, a variant or mutant of the OX-40 co-stimulatory domain protein includes no more than 5, 4, 3, 2, or 1 deletions compared to the naturally occurring OX-40 co-stimulatory domain protein. In some cases, a variant or mutant of the OX-40 co-stimulatory domain protein includes no more than 5, 4, 3, 2, or 1 insertions compared to the naturally occurring OX-40 co-stimulatory domain protein. In some cases, a variant or mutant of the OX-40 co-stimulatory domain protein does not include deletions compared to the naturally occurring OX-40 co-stimulatory domain protein. In some cases, a variant or mutant of the OX-40 co-stimulatory domain protein does not include insertions compared to the naturally occurring OX-40 co-stimulatory domain protein. In some cases, a variant or mutant of the OX-40 co-stimulatory domain protein includes substitutions that are conservative substitutions compared to the naturally occurring OX-40 co-stimulatory domain protein. In some cases, the OX-40 co-stimulatory domain includes all or a portion of the protein identified by the NCBI sequence reference NP_003318.1, or an isoform or naturally occurring mutant or variant thereof. Non-limiting examples of human OX-40 amino acid sequences available under NCBI sequence references are as follows:

```
NP_003318.1
                                        (SEQ ID NO: 60)
MCVGARRLGRGPCAALLLLGLGLSTVTGLHCVGDTYPSNDRCCHECRPG

NGMVSRCSRSQNTVCRPCGPGFYNDVVSSKPCKPCTWCNLRSGSERKQL

CTATQDTVCRCRAGTQPLDSYKPGVDCAPCPPGHFSPGDNQACKPWTNC

TLAGKHTLQPASNSSDAICEDRDPPATQPQETQGPPARPITVQPTEAWP

RTSQGPSTRPVEVPGGRAVAAILGLGLVLGLLGPLAILLALYLLRRDQR

LPPDAHKPPGGGSFRTPIQEEQADAHSTLAKI
```

In some cases, the OX-40 co-stimulatory domain is encoded by all or a portion of the nucleic acid sequence identified by the NCBI sequence reference NM_003327.3, or an isoform or naturally occurring mutant or variant thereof. In some cases, a variant or mutant of the OX-40 co-stimulatory domain nucleic acid sequence includes no more than 5, 4, 3, 2, or 1 deletions compared to the naturally occurring OX-40 co-stimulatory domain nucleic acid sequence. In some cases, a variant or mutant of the OX-40 co-stimulatory domain nucleic acid sequence includes no more than 5, 4, 3, 2, or 1 insertions compared to the naturally occurring OX-40 co-stimulatory domain nucleic acid sequence. In some cases, a variant or mutant of the OX-40 co-stimulatory domain nucleic acid sequence does not include deletions compared to the naturally occurring OX-40 co-stimulatory domain nucleic acid sequence. In some cases, a variant or mutant of the OX-40 co-stimulatory domain nucleic acid sequence does not include insertions compared to the naturally occurring OX-40 co-stimulatory domain nucleic acid sequence. In some cases, a variant or mutant of the OX-40 co-stimulatory domain nucleic acid sequence includes substitutions that are conservative substitutions compared to the naturally occurring OX-40 co-stimulatory domain nucleic acid sequence.

The term "CTLA-4 co-stimulatory domain" as provided herein includes any of the recombinant or naturally-occurring forms of the co-stimulatory domain of CTLA-4, or variants or homologs thereof that maintain CTLA-4 co-stimulatory domain activity (e.g. within at least 50%, 80%, 90%, 95%, 96%, 97%, 98%, 99% or 100% activity compared to the CTLA-4 co-stimulatory domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CTLA-4 co-stimulatory domain polypeptide. In some cases, CTLA-4 co-stimulatory domain protein is a human CTLA-4 co-stimulatory domain protein. In some cases, the CTLA-4 co-stimulatory domain includes no more than 5, 4, 3, 2, or 1 deletions. In some cases, the CTLA-4 co-stimulatory domain protein includes no more than 5, 4, 3, 2, or 1 insertions. In some cases, the CTLA-4 co-stimulatory domain protein does not include deletions. In some cases, CTLA-4 co-stimulatory domain protein does not include insertions. In some cases, the CTLA-4 co-stimulatory domain protein includes substitutions that are conservative substitutions. In some cases, CTLA-4 co-stimulatory domain protein includes the sequence AVSLSKMLKKRSPLTTGVYVKMPPTEPECEKQFQPYFIPIN (SEQ ID NO:17). In some cases, CTLA-4 co-stimulatory domain protein is the sequence SEQ ID NO: 17. In some cases, the CTLA-4 co-stimulatory domain amino acid sequence has at least or about 50%, 60%, 70%, 75%, 80%, 85%, 90%, 91%, 92%, 93%, 94%, 95%, 96%, 97%, 98%, or 99% sequence identify to SEQ ID NO:17. In some cases, the CTLA-4 co-stimulatory domain is a human CTLA-4 co-stimulatory domain protein. In some cases, a variant or mutant of the CTLA-4 co-stimulatory domain protein includes no more than 5, 4, 3, 2, or 1 deletions compared to the naturally occurring CTLA-4 co-stimulatory domain protein. In some cases, a variant or mutant of the CTLA-4 co-stimulatory domain protein includes no more than 5, 4, 3, 2, or 1 insertions compared to the naturally occurring CTLA-4 co-stimulatory domain protein. In some cases, a variant or mutant of the CTLA-4 co-stimulatory domain protein does not include deletions compared to the naturally occurring CTLA-4 co-stimulatory domain protein. In some cases, a variant or mutant of the CTLA-4 co-stimulatory domain protein does not include insertions compared to the naturally occurring CTLA-4 co-stimulatory domain protein. In some cases, a variant or mutant of the CTLA-4 co-stimulatory domain protein includes substitutions that are conservative substitutions compared to the naturally occurring CTLA-4 co-stimulatory domain protein. In some cases, the CTLA-4 co-stimulatory domain includes all or a portion of the protein identified by the NCBI sequence reference NP_001032720.1, or an isoform or naturally occurring mutant or variant thereof. In some cases, the CTLA-4 co-stimulatory domain includes all or a portion of the protein identified by the NCBI sequence reference NP_005205.2, or an isoform or naturally occurring mutant or variant thereof. Non-limiting examples of human CTLA-4 amino acid sequences available under NCBI sequence references are as follows:

NP_001032720.1
(SEQ ID NO: 61)
MACLGFQRHKAQLNLATRTWPCTLLFFLLFIPVFCKAMHVAQPAVVLAS

SRGIASFVCEYASPGKATEVRVTVLRQADSQVTEVCAATYMNIGNELTF

LDDSICTGTSSGNQVNLTIQGLRAMDTGLYICKVELMYPPPYYLGIGNG

TQIYVIAKEKKPSYNRGLCENAPNRARM

NP_005205.2
(SEQ ID NO: 62)
MACLGFQRHKAQLNLATRTWPCTLLFFLLFIPVFCKAMHVAQPAVVLAS

SRGIASFVCEYASPGKATEVRVTVLRQADSQVTEVCAATYMMGNELTFL

DDSICTGTSSGNQVNLTIQGLRAMDTGLYICKVELMYPPPYYLGIGNGT

QIYVIDPEPCPDSDFLLWILAAVSSGLFFYSFLLTAVSLSKMLKKRSPL

TTGVYVKMPPTEPECEKQFQPYFIPIN

In some cases, the CTLA-4 co-stimulatory domain is encoded by all or a portion of the nucleic acid sequence identified by the NCBI sequence reference NM_001037631.3, or an isoform or naturally occurring mutant or variant thereof. In some cases, the CTLA-4 co-stimulatory domain is encoded by all or a portion of the nucleic acid sequence identified by the NCBI sequence reference NM_005214.5, or an isoform or naturally occurring mutant or variant thereof. In some cases, a variant or mutant of the CTLA-4 co-stimulatory domain nucleic acid sequence includes no more than 5, 4, 3, 2, or 1 deletions compared to the naturally occurring CTLA-4 co-stimulatory domain nucleic acid sequence. In some cases, a variant or mutant of the CTLA-4 co-stimulatory domain nucleic acid sequence includes no more than 5, 4, 3, 2, or 1 insertions compared to the naturally occurring CTLA-4 co-stimulatory domain nucleic acid sequence. In some cases, a variant or mutant of the CTLA-4 co-stimulatory domain nucleic acid sequence does not include deletions compared to the naturally occurring CTLA-4 co-stimulatory domain nucleic acid sequence. In some cases, a variant or mutant of the CTLA-4 co-stimulatory domain nucleic acid sequence does not include insertions compared to the naturally occurring CTLA-4 co-stimulatory domain nucleic acid sequence. In some cases, a variant or mutant of the CTLA-4 co-stimulatory domain nucleic acid sequence includes substitutions that are conservative substitutions compared to the naturally occurring CTLA-4 co-stimulatory domain nucleic acid sequence.

The term "PD-1 co-stimulatory domain" as provided herein includes any of the recombinant or naturally-occurring forms of the co-stimulatory domain of PD-1, or variants or homologs thereof that maintain PD-1 co-stimulatory domain activity (e.g. within at least 50%, 80%, 90%, 95%, 96%, 97%, 98%, 99% or 100% activity compared to the PD-1 co-stimulatory domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring PD-1 co-stimulatory domain polypeptide. In some cases, the PD-I co-stimulatory domain amino acid sequence includes the sequence of CSRAARGTI-GARRTGQPLKEDPSAVPVFSVDYGELDFQWREKT-PEPPVPCVPEQTEYAT IVFPSGMGTSSP ARRGSADGPRSAQPLRPEDGHCSWPL (SEQ ID NO:33). In some cases, the PD-1 co-stimulatory domain" is a human PD-1 co-stimulatory domain protein. In some cases, a variant or mutant of the PD-1 co-stimulatory domain protein includes no more than 5, 4, 3, 2, or 1 deletions compared to the naturally occurring PD-1 co-stimulatory domain protein. In some cases, a variant or mutant of the PD-1 co-stimulatory domain protein includes no more than 5, 4, 3, 2, or 1 insertions compared to the naturally occurring PD-1 co-stimulatory domain protein. In some cases, a variant or mutant of the PD-1 co-stimulatory domain protein does not include deletions compared to the naturally occurring PD-1 co-stimulatory domain protein. In some cases, a variant or mutant of the PD-1 co-stimulatory domain protein does not include insertions compared to the naturally occurring PD-1 co-stimulatory domain protein. In some cases, a variant or mutant of the PD-1 co-stimulatory domain protein includes substitutions that are conservative substitutions compared to the naturally occurring PD-1 co-stimulatory domain protein. In some cases, the PD-1 co-stimulatory domain includes all or a portion of the protein identified by the NCBI sequence reference NP_005009.2, or an isoform or naturally occurring mutant or variant thereof. Non-limiting examples of human PD-1 amino acid sequences available under NCBI sequence references are as follows:

NP_005009.2
(SEQ ID NO: 63)
MQIPQAPWPVVWAVLQLGWRPGWFLDSPDRPWNPPTFSPALLVVTEGDN

ATFTCSFSNTSESFVLNWYRMSPSNQTDKLAAFPEDRSQPGQDCRFRVT

QLPNGRDFHMSVVRARRNDSGTYLCGAISLAPKAQIKESLRAELRVTER

RAEVPTAHPSPSPRPAGQFQTLVVGVVGGLLGSLVLLVWVLAVICSRAA

RGTIGARRTGQPLKEDPSAVPVFSVDYGELDFQWREKTPEPPVPCVPEQ

TEYATIVFPSGMGTSSPARRGSADGPRSAQPLRPEDGHCSWPL

In some cases, the PD-1 co-stimulatory domain is encoded by all or a portion of the nucleic acid sequence identified by the NCBI sequence reference NM_005018.2, or an isoform or naturally occurring mutant or variant thereof. In some cases, a variant or mutant of the PD-1 co-stimulatory domain nucleic acid sequence includes no more than 5, 4, 3, 2, or 1 deletions compared to the naturally occurring PD-1 co-stimulatory domain nucleic acid sequence. In some cases, a variant or mutant of the PD-1 co-stimulatory domain nucleic acid sequence includes no more than 5, 4, 3, 2, or 1 insertions compared to the naturally occurring PD-1 co-stimulatory domain nucleic acid sequence. In some cases, a variant or mutant of the PD-1 co-stimulatory domain nucleic acid sequence does not include deletions compared to the naturally occurring PD-1 co-stimulatory domain nucleic acid sequence. In some cases, a variant or mutant of the PD-1 co-stimulatory domain nucleic acid sequence does not include insertions compared to the naturally occurring PD-1 co-stimulatory domain nucleic acid sequence. In some cases, a variant or mutant of the PD-1 co-stimulatory domain nucleic acid sequence includes substitutions that are conservative substitutions compared to the naturally occurring PD-1 co-stimulatory domain nucleic acid sequence.

The term "GITR co-stimulatory domain" as provided herein includes any of the recombinant or naturally-occurring forms of the co-stimulatory domain of GITR, or variants or homologs thereof that maintain GITR co-stimulatory domain activity (e.g. within at least 50%, 80%, 90%, 95%, 96%, 97%, 98%, 99% or 100% activity compared to the GITR co-stimulatory domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring GITR co-stimulatory domain polypeptide. In some cases, the GITR co-stimulatory domain amino acid sequence includes the sequence of QLGLHIWQLR-SQCMWPRETQLLLEVPPSTEDARSCQFPEEERGER-SAEEKGRLGDLWV (SEQ ID NO:67) In some cases, the GITR co-stimulatory domain is a human GITR co-stimulatory domain protein. In some cases, a variant or mutant of the GITR co-stimulatory domain protein includes no more than 5, 4, 3, 2, or 1 deletions compared to the naturally occurring GITR co-stimulatory domain protein. In some cases, a variant or mutant of the GITR co-stimulatory domain protein includes no more than 5, 4, 3, 2, or 1 insertions compared to the naturally occurring GITR co-stimulatory domain protein. In some cases, a variant or mutant of the GITR co-stimulatory domain protein does not include deletions compared to the naturally occurring GITR co-stimulatory domain protein. In some cases, a variant or mutant of the GITR co-stimulatory domain protein does not include insertions compared to the naturally occurring GITR co-stimulatory domain protein. In some cases, a variant or mutant of the GITR co-stimulatory domain protein includes substitutions that are conservative substitutions compared to the naturally occurring GITR co-stimulatory domain protein. In some cases, the GITR co-stimulatory domain includes all or a portion of the protein identified by the NCBI sequence reference NP_004186.1, or an isoform or naturally occurring mutant or variant thereof. In some cases, the GITR co-stimulatory domain includes all or a portion of the protein identified by the NCBI sequence reference NP_683699.1, or an isoform or naturally occurring mutant or variant thereof. In some cases, the GITR co-stimulatory domain includes all or a portion of the protein identified by the NCBI sequence reference NP_683700.1, or an isoform or naturally occurring mutant or variant thereof. Non-limiting examples of human GITR amino acid sequences available under NCBI sequence references are as follows:

NP_004186.1
(SEQ ID NO: 64)
MAQHGAMGAFRALCGLALLCALSLGQRPTGGPGCGPGRLLLGTGTDARC

CRVHTTRCCRDYPGEECCSEWDCMCVQPEFHCGDPCCTTCRHHPCPPGQ

GVQSQGKFSFGFQCIDCASGTFSGGHEGHCKPWTDCTQFGFLTVFPGNK

THNAVCVPGSPPAEPLGWLTVVLLAVAACVLLLTSAQLGLHIWQLRSQC

MWPRETQLLLEVPPSTEDARSCQFPEEERGERSAEEKGRLGDLWV

NP_683699.1
(SEQ ID NO: 65)
MAQHGAMGAFRALCGLALLCALSLGQRPTGGPGCGPGRLLLGTGTDARC

CRVHTTRCCRDYPGEECCSEWDCMCVQPEFHCGDPCCTTCRHHPCPPGQ

```
-continued
GVQSQGKFSFGFQCIDCASGTFSGGHEGHCKPWTDCCWRCRRRPKTPEA

ASSPRKSGASDRQRRRGGWETCGCEPGRPPGPPTAASPSPGAPQAAGAL

RSALGRALLPWQQKWVQEGGSDQRPGPCSSAAAAGPCRRERETQSWPPS

SLAGPDGVGS

NP_683700.1
                                           (SEQ ID NO: 66)
MAQHGAMGAFRALCGLALLCALSLGQRPTGGPGCGPGRLLLGTGTDARC

CRVHTTRCCRDYPGEECCSEWDCMCVQPEFHCGDPCCTTCRHHPCPPGQ

GVQSQGKFSFGFQCIDCASGTFSGGHEGHCKPWTDCTQFGFLTVFPGNK

THNAVCVPGSPPAEPLGWLTVVLLAVAACVLLLTSAQLGLHIWQLRKTQ

LLLEVPPSTEDARSCQFPEEERGERSAEEKGRLGDLWV
```

In some cases, the GITR co-stimulatory domain is encoded by all or a portion of the nucleic acid sequence identified by the NCBI sequence reference NM_148902.1, or an isoform or naturally occurring mutant or variant thereof. In some cases, the GITR co-stimulatory domain is encoded by all or a portion of the nucleic acid sequence identified by the NCBI sequence reference NM_004195.2, or an isoform or naturally occurring mutant or variant thereof. In some cases, the GITR co-stimulatory domain is encoded by all or a portion of the nucleic acid sequence identified by the NCBI sequence reference NM_148901.1, or an isoform or naturally occurring mutant or variant thereof. In some cases, a variant or mutant of the GITR co-stimulatory domain nucleic acid sequence includes no more than 5, 4, 3, 2, or 1 deletions compared to the naturally occurring GITR co-stimulatory domain nucleic acid sequence. In some cases, a variant or mutant of the GITR co-stimulatory domain nucleic acid sequence includes no more than 5, 4, 3, 2, or 1 insertions compared to the naturally occurring GITR co-stimulatory domain nucleic acid sequence. In some cases, a variant or mutant of the GITR co-stimulatory domain nucleic acid sequence does not include deletions compared to the naturally occurring GITR co-stimulatory domain nucleic acid sequence. In some cases, a variant or mutant of the GITR co-stimulatory domain nucleic acid sequence does not include insertions compared to the naturally occurring GITR co-stimulatory domain nucleic acid sequence. In some cases, a variant or mutant of the GITR co-stimulatory domain nucleic acid sequence includes substitutions that are conservative substitutions compared to the naturally occurring GITR co-stimulatory domain nucleic acid sequence.

The term "CD3ζ intracellular T-cell signaling domain" as provided herein includes any of the recombinant or naturally-occurring forms of the CD3ζ intracellular T-cell signaling domain, or variants or homologs thereof that maintain CD3ζ intracellular T-cell signaling domain activity (e.g. within at least 50%, 80%, 90%, 95%, 96%, 97%, 98%, 99% or 100% activity compared to the CD3ζ intracellular T-cell signaling domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD3ζ intracellular T-cell signaling domain polypeptide. In some cases, the CD3ζ intracellular T-cell signaling domain is a human CD3ζ intracellular T-cell signaling domain protein. In some cases, a variant or mutant of the CD3ζ intracellular T-cell signaling domain protein includes no more than 5, 4, 3, 2, or 1 deletions compared to the naturally occurring CD3ζ intracellular T-cell signaling domain protein. In some cases, a variant or mutant of the CD3ζ intracellular T-cell signaling domain protein includes no more than 5, 4, 3, 2, or 1 insertions compared to the naturally occurring CD3ζ intracellular T-cell signaling domain protein. In some cases, a variant or mutant of the CD3ζ intracellular T-cell signaling domain protein does not include deletions compared to the naturally occurring CD3ζ intracellular T-cell signaling domain protein. In some cases, a variant or mutant of the CD3ζ intracellular T-cell signaling domain protein does not include insertions compared to the naturally occurring CD3ζ intracellular T-cell signaling domain protein. In some cases, a variant or mutant of the CD3ζ intracellular T-cell signaling domain protein includes substitutions that are conservative substitutions compared to the naturally occurring CD3ζ intracellular T-cell signaling domain protein. In some cases, the CD3ζ intracellular T-cell signaling domain includes all or a portion of the protein identified by the NCBI sequence reference NP_000725.1, or an isoform or naturally occurring mutant or variant thereof. In some cases, the CD3ζ intracellular T-cell signaling domain includes all or a portion of the protein identified by the NCBI sequence reference NP_932170.1, or an isoform or naturally occurring mutant or variant thereof. Non-limiting examples of human CD3-zeta amino acid sequences available under NCBI sequence references are identified supra. In some cases, the CD3ζ intracellular T-cell signaling domain is encoded by all or a portion of the nucleic acid sequence identified by the NCBI sequence reference NM_000734.3, or an isoform or naturally occurring mutant or variant thereof. In some cases, the CD3ζ intracellular T-cell signaling domain is encoded by all or a portion of the nucleic acid sequence identified by the NCBI sequence reference NM_198053.2, or an isoform or naturally occurring mutant or variant thereof. In some cases, a variant or mutant of the CD3ζ intracellular T-cell signaling domain nucleic acid sequence includes no more than 5, 4, 3, 2, or 1 deletions compared to the naturally occurring CD3ζ intracellular T-cell signaling domain nucleic acid sequence. In some cases, a variant or mutant of the CD3ζ intracellular T-cell signaling domain nucleic acid sequence includes no more than 5, 4, 3, 2, or 1 insertions compared to the naturally occurring CD3ζ intracellular T-cell signaling domain nucleic acid sequence. In some cases, a variant or mutant of the CD3ζ intracellular T-cell signaling domain nucleic acid sequence does not include deletions compared to the naturally occurring CD3ζ intracellular T-cell signaling domain nucleic acid sequence. In some cases, a variant or mutant of the CD3ζ intracellular T-cell signaling domain nucleic acid sequence does not include insertions compared to the naturally occurring CD3ζ intracellular T-cell signaling domain nucleic acid sequence. In some cases, a variant or mutant of the CD3ζ intracellular T-cell signaling domain nucleic acid sequence includes substitutions that are conservative substitutions compared to the naturally occurring CD3ζ intracellular T-cell signaling domain nucleic acid sequence.

The phrase "specifically (or selectively) binds to an antibody" or "specifically (or selectively) immunoreactive with," when referring to a protein or peptide refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions typically requires an antibody that is selected for its specificity for a particular protein. For example, polyclonal antibodies can be selected to obtain only a subset of antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).

A "ligand" refers to an agent, e.g., a polypeptide or other molecule, capable of binding to a receptor.

The term "recombinant" when used with reference, for example, to a cell, a nucleic acid, a protein, or a vector, indicates that the cell, nucleic acid, protein or vector has been modified by or is the result of laboratory methods. Thus, for example, recombinant proteins include proteins produced by laboratory methods. Recombinant proteins can include amino acid residues not found within the native (non-recombinant) form of the protein or can be include amino acid residues that have been modified, e.g., labeled.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "cell" as used herein, refers to a cell carrying out metabolic or other functions sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian (e.g., human) and insect (e.g., *spodoptera*) cells. Cells may be useful when they are naturally nonadherent or have been treated not to adhere to surfaces, for example by trypsinization.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell. The level of expression of non-coding nucleic acid molecules (e.g., siRNA) may be detected by standard PCR or Northern blot methods well known in the art. See, Sambrook et al., 1989 *Molecular Cloning: A Laboratory Manual,* 18.1-18.88.

The terms "plasmid", "vector" or "expression vector" refer to a nucleic acid molecule that encodes for genes and/or regulatory elements necessary for the expression of genes. Expression of a gene from a plasmid can occur in cis or in trans. If a gene is expressed in cis, the gene and the regulatory elements are encoded by the same plasmid. Expression in trans refers to the instance where the gene and the regulatory elements are encoded by separate plasmids.

The terms "transfection", "transduction", "transfecting" or "transducing" can be used interchangeably and are defined as a process of introducing a nucleic acid molecule or a protein to a cell. Nucleic acids are introduced to a cell using non-viral or viral-based methods. The nucleic acid molecules may be gene sequences encoding complete proteins or functional portions thereof. Non-viral methods of transfection include any appropriate transfection method that does not use viral DNA or viral particles as a delivery system to introduce the nucleic acid molecule into the cell. Exemplary non-viral transfection methods include calcium phosphate transfection, liposomal transfection, nucleofection, sonoporation, transfection through heat shock, magnetifection and electroporation. In some embodiments, the nucleic acid molecules are introduced into a cell using electroporation following standard procedures well known in the art. For viral-based methods of transfection any useful viral vector may be used in the methods described herein. Examples for viral vectors include, but are not limited to retroviral, adenoviral, lentiviral and adeno-associated viral vectors. In some embodiments, the nucleic acid molecules are introduced into a cell using a retroviral vector following standard procedures well known in the art. The terms "transfection" or "transduction" also refer to introducing proteins into a cell from the external environment. Typically, transduction or transfection of a protein relies on attachment of a peptide or protein capable of crossing the cell membrane to the protein of interest. See, e.g., Ford et al. (2001) *Gene Therapy* 8:1-4 and Prochiantz (2007) *Nat. Methods* 4:119-20.

Expression of a transfected gene can occur transiently or stably in a cell. During "transient expression" the transfected gene is not transferred to the daughter cell during cell division. Since its expression is restricted to the transfected cell, expression of the gene is lost over time. In contrast, stable expression of a transfected gene can occur when the gene is co-transfected with another gene that confers a selection advantage to the transfected cell. Such a selection advantage may be a resistance towards a certain toxin that is presented to the cell. Expression of a transfected gene can further be accomplished by transposon-mediated insertion into the host genome. During transposon-mediated insertion, the gene is positioned in a predictable manner between two transposon linker sequences that allow insertion into the host genome as well as subsequent excision. Stable expression of a transfected gene can further be accomplished by infecting a cell with a lentiviral vector, which after infection forms part of (integrates into) the cellular genome thereby resulting in stable expression of the gene.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated, that the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be, for example, a peptide compound as described herein and an antigen binding site.

The term "modulation", "modulate", or "modulator" are used in accordance with their plain ordinary meaning and refer to the act of changing or varying one or more properties. "Modulator" refers to a composition that increases or decreases the level of a target molecule or the function of a target molecule or the physical state of the target of the molecule. "Modulation" refers to the process of changing or varying one or more properties. For example, as applied to the effects of a modulator on a biological target, to modulate means to change by increasing or decreasing a property or function of the biological target or the amount of the biological target.

As defined herein, the term "inhibition", "inhibit", "inhibiting" and the like in reference to a protein-inhibitor (e.g. antagonist) interaction means negatively affecting (e.g. decreasing) the activity or function of the protein relative to the activity or function of the protein in the absence of the inhibitor. In some cases, inhibition refers to reduction of a disease or symptoms of disease. Thus, In some cases, inhibition includes, at least in part, partially or totally blocking stimulation, decreasing, preventing, or delaying activation, or inactivating, desensitizing, or down-regulating signal transduction or enzymatic activity or the amount of a protein. In some cases, the amount of inhibition may be 10%, 20%, 30%, 40%, 50%, 60%, 70%, 80%, 90%, 100% or less in comparison to a control in the absence of the antagonist. In some cases, the inhibition is 1.5-fold, 2-fold, 3-fold, 4-fold, 5-fold, 10-fold, or more than the expression or activity in the absence of the antagonist.

Depending on context, the term "activation", "activate", "activating" and the like in reference to a protein-activator (e.g. agonist) interaction means positively affecting (e.g. increasing) the activity or function of the relative to the activity or function of the protein in the absence of the activator (e.g. composition described herein). Thus, In some cases, activation may include, at least in part, partially or totally increasing stimulation, increasing or enabling activation, or activating, sensitizing, or up-regulating signal transduction or enzymatic activity or the amount of a protein decreased in a disease. The amount of activation may be 10%, 20%, 30%, 40%, 50%, 60%, 70%, 80%, 90%, 100% or more in comparison to a control in the absence of the agonist. In some cases, the activation is 1.5-fold, 2-fold, 3-fold, 4-fold, 5-fold, 10-fold, or more than the expression or activity in the absence of the agonist.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by using a method as described herein), results in reduction of the disease or one or more disease symptoms.

Depending on context, the term "biological sample" or "sample" refers to a material or materials obtained from or derived from a subject or patient. In some cases, a biological sample includes sections of tissues such as biopsy and autopsy samples, and frozen sections taken for histological purposes. Non-limiting examples of samples include bodily fluids such as blood and blood fractions or products (e.g., serum, plasma, platelets, red blood cells, and the like), sputum, tissue, cultured cells (e.g., primary cultures, explants, and transformed cells) stool, urine, synovial fluid, joint tissue, synovial tissue, synoviocytes, fibroblast-like synoviocytes, macrophage-like synoviocytes, immune cells, hematopoietic cells, fibroblasts, macrophages, T cells, etc. A biological sample is typically obtained from a eukaryotic organism, such as a mammal such as a primate e.g., chimpanzee or human; cow; dog; cat; a rodent, e.g., guinea pig, rat, mouse; rabbit; or a bird; reptile; or fish. In some cases, a biological sample from the subject (e.g., such as blood) has aberrant CD6 expression and/or function compared to a control. In some cases, a biological sample from the subject (e.g., such as blood) has aberrant immune cell activity or growth (e.g., an abnormal number of CD6+ immune cells or CD6+ cells with abnormal activity).

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

"Patient" or "subject in need thereof" refers to a living member of the animal kingdom suffering from or that may suffer from the indicated disorder. In some cases, the subject is a member of a species that includes individuals who naturally suffer from the disease. In some cases, a subject is a living organism suffering from or prone to a disease or condition that can be treated by administration of a composition or pharmaceutical composition as provided herein. Non-limiting examples include humans, other mammals, bovines, rats, mice, dogs, monkeys, goat, sheep, cows, deer, and other non-mammalian animals. In some embodiments, a patient is human.

The terms "disease" or "condition" refer to a state of being or health status of a patient or subject capable of being treated with a compound, pharmaceutical composition, or method provided herein. In some cases, the disease is an autoimmune disease (e.g., Type I Diabetes, Graft-versus-Host Disease). In some cases, An "autoimmune disease" as used herein refers to a disease or disorder that arises from altered immune reactions by the immune system of a subject, e.g., against substances tissues and/or cells normally present in the body of the subject. Autoimmune diseases include, but are not limited to, arthritis, rheumatoid arthritis, psoriatic arthritis, juvenile idiopathic arthritis, scleroderma, systemic scleroderma, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, autoimmune thyroiditis, Behcet's disease, Crohn's disease, ulcerative colitis, bullous pemphigoid, sarcoidosis, psoriasis, ichthyosis, Graves ophthalmopathy, inflammatory bowel disease, Addison's disease, Vitiligo, asthma, Graft-versus-Host Disease, and allergic asthma.

As used herein, an "inflammatory disease" refers to a disease or disorder associated with abnormal or altered inflammation. Inflammation is a biological response initiated by the immune system as part of the healing process in response to a pathogen, damaged cells or tissues or irritants. Chronic inflammation can lead to a variety of diseases. Inflammatory diseases include, but are not limited to, atherosclerosis, allergies, asthma, rheumatoid arthritis, transplant rejection, celiac disease, chronic prostatitis, inflammatory bowel diseases, pelvic inflammatory diseases, and inflammatory myopathies.

The term "associated" or "associated with" in the context of a substance or substance activity or function associated with a disease (e.g., an autoimmune disease) means that the disease is caused by (in whole or in part), or a symptom of the disease is caused by (in whole or in part) the substance or substance activity or function.

The terms "treating", or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, include prevention of an injury, pathology, condition, or disease. In some cases, "treating" refers to treatment of an autoimmune disease.

An "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of a "therapeutically effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances, and the like, that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

In some cases, the term "administering" includes oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. In some cases, administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

Pharmaceutical compositions may include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule, and/or reducing, eliminating, or slowing the progression of disease symptoms.

Recombinant Proteins and CAR T-Cells

In an aspect, provided herein are recombinant proteins including the proteins expressed by the isolated nucleic acid provided herein, including embodiments thereof. Thus, in an aspect is provided a recombinant protein, such as a chimeric antigen receptor (CAR), that includes a single chain variable fragment (scFv) targeted to CD6 and a transmembrane domain. In an aspect, provided herein is a scFv targeted to CD6 without a transmembrane domain. In an aspect, provided herein is a cell (e.g., a population of cells, such as a population of immune effector cells) engineered to express a CAR, wherein the CAR comprises an antigen-binding domain, and a transmembrane domain. In some cases, the antigen binding domain comprises an antibody fragment or variant targeted to CD6. In some cases, the antigen-binding domain is a single chain variable fragment (scFv) targeted to CD6. In some cases, the CAR further comprises an intracellular signaling domain. In some cases, the cell that expresses the CAR is a T lymphocyte (a CAR T-cell) or an NK cell. In some cases, the cell that expresses the CAR is a T lymphocyte (a CAR T-cell) or an NK cell. In some cases, the cell is a CD4+ T cell, or a CD8+ T cell. In some cases, the T-cell is a regulatory T-cell (Treg).

In some cases, the antigen-binding domain can comprise CDRs of a monoclonal antibody, variable regions of a monoclonal antibody, and/or antigen binding fragments thereof. In some cases, the fragment can be any number of different antigen binding domains of an antigen-specific antibody. In some cases, the antigen-binding domain comprises a CD6-binding fragment of an anti-CD6 antibody. In some cases, the antigen-binding domain comprises the CDRs of an anti-CD6 antibody. In some cases, the antigen-binding domain comprises the VH and VL chains of an anti-CD6 antibody. In some cases, the antigen-binding domain comprises a scFv that comprises CDRs of an anti-CD6 antibody. In some cases, the antigen-binding domain comprises a scFv that comprises the VH and VL chains of an anti-CD6 antibody. In some cases, the anti-CD6 antibody is a monoclonal antibody. In some cases, the monoclonal antibody is a human or a humanized monoclonal antibody. In some cases, the monoclonal antibody is itolizumab. In some cases, the fragment is an antigen-specific scFv encoded by a sequence that is optimized for human codon usage for expression in human cells. In some cases, the monoclonal antibody is a chimericmonoclonal antibody. In some cases, the monoclonal antibody is itolizumab. In some cases, the monoclonal antibody is T12. 1. In some cases, the monoclonal antibody is UMCD6. In some cases, the monoclonal antibody is MEM98. In some cases, the monoclonal antibody is MT605. In some cases, the monoclonal antibody is an antibody described in Gangemi et al. (1989) *J Immunol* 143(8):2439-47 or U.S. Pat. No. 6,572,857, the entire contents of each of which are incorporated herein by reference. In some cases, the fragment is an antigen-specific scFv encoded by a sequence that is optimized for human codon usage for expression in human cells. In some cases, the antigen-binding domain includes the following VH sequence or a variant thereof: EVQLVESGG-GLVKPGGSLKLSCAASGFKFSRYAMSWVRQAPGKR-LEWVATISS GGSYIYYP DSVKGRFTISRDNVKNT-LYLQMSSLRSEDT AMYYCARRDYDLDYFDSWGQGTLVTVSS (SEQ ID NO: 35). In some cases, the antigen-binding domain includes the following VL sequence or a variant thereof: DIQMTQSPSSLSASVGDRVTITCKASRDIR-SYLTWYQQKPGKAPKTLIYYATSLADGVPSRF SGSGSGQDYSLTISSLESDDTATYY-CLQHGESPFTFGSGTKLEIKRA (SEQ ID NO: 34). In some cases, the antigen-binding domain includes the following VH sequence or a variant thereof: EVQLVESGGGL VKPGGSLKLSCAASGFKFSRYAMSWVRQTPEKR-LEWVATISSGGSYIYYPDSVKGRFTISR DNVKNT-LYLQMSSLRSEDTAMYYCARRDYDLDYFD-SWGQGTTLTVSS (SEQ ID NO:68). In some cases, the antigen-binding domain includes the following VL sequence or a variant thereof DIKMTQSPSSMYASLGERVTITCK-ASRDIRSYLTWYQQKPWKSPKTLIYYAT-SLADGVPSRF SGSGSGQDYSLTISSLESDDTATYY-CLQHGESPFTFGSGTKLEIKRA (SEQ ID NO:69). In some cases, the VL includes the following sequence or a variant thereof: IQMTQSPSSLSASVGDRVTITCKAS-RDIRSYLTWYQQKPGKAPKTLIYYATSLADGVPS RFSGSGSGQ (SEQ ID NO:75). In some cases, the VL includes the following sequence or a variant thereof: DIQMTQSPSSLSASVGDRVTITCKASRDIRSY (SEQ ID NO:76). In some cases, the VL includes the following sequence or a variant thereof: LTWYQQKPGKAPKTLIYYAT-SLADGVPSRFSGSGSGQDYSLTISSLESDDTATYY-CLQH GESPFT (SEQ ID NO:77). In some cases, the VL includes the following sequence or a variant thereof: FGSGTKLEIKRA (SEQ ID NO:78). In some cases, the VH includes the following sequence or a variant thereof: EVQLVESGGGLVKPGGSLKLSCAASGFKFSRYAMS (SEQ ID NO:79). In some cases, the VH includes the following sequence or a variant thereof: WVRQAPGKR-LEWVATISSGG (SEQ ID NO:80). In some cases, the VH includes the following sequence or a variant thereof: SYIYYPDSVKGRFTISRDNVKNTLYLQMSSLRSED-TAMYYCARRDYDLDYFDS (SEQ ID NO:81). In some cases, the VH includes the following sequence or a variant thereof: WGQGTLVTVSS (SEQ ID NO:82). In some cases, a variant of a VH or VL sequence provided herein has 5, 4, 3, 2, 1, or 0 deletions compared to the sequence. In some cases, a variant of a VH or VL sequence provided herein has 5, 4, 3, 2, 1, or O insertions compared to the sequence. In some cases, a variant of a VH or VL sequence provided herein has 5, 4, 3, 2, 1, or 0 substitutions compared to the sequence. In embodiments, a variant of a VH or VL sequence provided herein has 10, 9, 8, 7, 6, 5, 4, 3, 2, or 1 substitutions compared to the sequence. In some cases, 1 or more or all of the substitutions are conservative substitutions.

TABLE 1

Exemplary Sequences for Antigen Binding domains and light and heavy chain variable regions.

| | |
|---|---|
| Heavy CDR1 Kabat | VQLVESGGGLVKPGGSLKLS |
| Heavy CDR2 Kabat | FSRYAMSWVRQAPGK |
| Heavy CDR3 Kabat | RDYDLDYFDSWGQGTLVTV |
| Heavy Chain Variable Region | EVQLVESGGGLVKPGGSLKLSCAASGFKFSRYAMSWVR QAPGKRLEWVATISSGGSYIYYPDSVKGRFTISRDNVK NTLYLQMSSLRSEDTAMYYCARRDYDLDYFDSWGQGTL VTVSS |
| Light Chain Variable Region | DIQMTQSPSSLSASVGDRVTITCKASRDIRSYLTWYQQ KPGKAPKTLIYYATSLADGVPSRFSGSGSGQDYSLTIS SLESDDTATYYCLQHGESPFTFGSGTKLEIKRA |
| Portion of Light Chain Variable Region | IQMTQSPSSLSASVGDRVTITCKASRDIRSYLTWYQQK PGKAPKTLIYYATSLADGVPSRFSGSGSGQ |

In some cases, the arrangement could be multimeric, such as a diabody or multimers. In some cases, the multimers are most likely formed by cross pairing of the variable portion of the light and heavy chains into what has been referred as a diabody. In some cases, the hinge portion of the construct can have multiple alternatives from being totally deleted, to having the first cysteine maintained, to a proline rather than a serine substitution, to being truncated up to the first cysteine. In some cases, the Fc portion can be deleted. In some cases, any protein that is stable and/or dimerizes can serve this purpose. In some cases, a CAR comprises one of the Fc domains, e.g., either the CH2 or CH3 domain from human immunoglobulin. In some cases, a CAR uses the hinge, CH2 and CH3 region of a human immunoglobulin that has been modified to improve dimerization. In some cases, just the hinge portion of an immunoglobulin is used. In some cases, when expressed, the antigen-binding domain comprises a signal peptide that directs expression of the CAR to the cell membrane. In some cases, the signal peptide is not present in the CAR when it is on the surface of a cell. In some cases, the signal peptide is the same or different from the signal peptide from an antibody that has the CDRs of the antigen-binding domain.

In some cases, the antigen-binding domain (e.g., an scFv that is part of the CAR) has a relatively low affinity ($K_D$) for CD6, while still being specific for CD6. In some cases, the affinity is about $1\times10^{-4}$ M to about $1\times10^{-6}$ M, about $1\times10^{-8}$ M to about $1\times10^{-7}$ M, about $1\times10^{-8}$ M to about $1\times10^{-6}$ M, about $1\times10^{-9}$ M to about $1\times10^{-7}$ M, about $1.5\times10^{-8}$ M to about $1.5\times10^{-7}$ M, or about $1\times10^{-7}$ M, $2\times10^{-7}$ M, $3\times10^{-7}$ M, $4\times10^{-7}$ M, $5\times10^{-7}$ M, $6\times10^{-7}$ M, $7\times10^{-7}$ M, $8\times10^{-7}$ M, $9\times10^{-7}$ M, about $1\times10^{-8}$ M, $2\times10^{-8}$ M, $3\times10^{-8}$ M, $4\times10^{-8}$ M, $5\times10^{-8}$ M, $6\times10^{-8}$ M, $7\times10^{-8}$ M, $8\times10^{-8}$ M, or $9\times10^{-8}$ M. One of skill in the art can readily detect the $K_D$ of an antibody. In a non-limiting example, affinity may be detected, e.g., by yeast surface display. This approach is a genotype-phenotype linkage strategy mediated by production, secretion, and capture of protein candidates. Candidate proteins can be sorted using combinations of multiple strategies with multiple selection pressures including affinity and stability. See, e.g., Feldhaus et al. (2003) Flow-cytometric isolation of human antibodies from a nonimmune *Saccharomyces cerevisiae* surface display library. Nature biotechnology. 21:163-170; and Zorniak et al. (207) Yeast display biopanning identifies human antibodies targeting glioblastoma stem-like cells. Scientific Reports. 7:15840, the entire contents of each of which are incorporated herein by reference.

In some cases, an scFv may be designed to have a particular orientation (e.g., $V_H$-$V_L$ or $V_L$-$V_H$ from the N-terminus to the C-terminus). In some cases, the $V_H$ and $V_L$ in an scFv are oriented $V_H$-$V_L$ from the N-terminus to the C-terminus. In some cases, the $V_H$ and $V_L$ in an scFv are oriented $V_L$-$V_H$ from the N-terminus to the C-terminus. In some cases, the $V_H$ and $V_L$ portions of the expressed protein will have a slightly different conformation depending on the orientation thereof. In some cases, the orientation of the $V_H$ and $V_L$ relationship may confer differential affinities for the ligand (e.g., CD6). In some cases, the differential affinity of one orientation compared to another is one order of magnitude or higher.

In some cases, the $V_H$ and $V_L$ portions of the scFv are directly adjacent and contiguous to one another. Alternatively, the $V_H$ and $V_L$ of the scFv may be separated by a linker (e.g., flexible linker). In some cases, the linker is a polypeptide linker. In some cases, the polypeptide linker is a flexible linker. In some cases, the $V_H$ and $V_L$ (in either orientation) of the scFv may be fused through a flexible linker with different sizes e.g.: 18 amino acids, 19 amino acids, or 20 amino acids; allowing the $V_H$ and $V_L$ of the scFv to fold into their native configuration and conserving the antigen-binding properties. In some cases, the linker includes glycine and/or serine residues. In some cases, the linker has the amino acid sequence GST-SGGGSGGGSGGGSS (SEQ ID NO:36). In some cases, the linker has the amino acid sequence GGGGSGGGGSGGGGSGGGGS (SEQ ID NO:37). In some cases, the linker is about 18 amino acids in length. In some cases, the linker is 18 amino acids in length. In some cases, the linker is about 19 amino acids in length. In some cases, the linker is 19 amino acids in length. In some cases, the linker is about 20 amino acids in length. In some cases, the linker is 20 amino acids in length. In some cases, the linker sequence is long enough to allow the expressed scFv to fold into its native configuration. In some cases, the linker sequence is long enough to allow the expressed scFv to maintain its antigen-binding properties. Techniques for assessing protein folding include, but are not limited to, NMR, X-Ray crystallography, circular dichroism, fluorescence spectroscopy, dual polarization interferometry, and other techniques well known in the art. Techniques for assessing antigen-binding behavior include, but are not limited to, surface plasmon resonance (SPR), various ligand binding assays, and other techniques well known in the art.

In some cases, a recombinant protein provided herein, including embodiments thereof, may further include additional components of a CAR. CARs that include such additional components and cells expressing such CARs are also included.

In some cases, the recombinant protein (such as a CAR) provided herein (e.g. isolated or expressed on the surface of a cell), including embodiments thereof, may further include a transmembrane domain as described herein, including embodiments thereof, a hinge region as described herein, including embodiments thereof, an intracellular signaling domain (such as a T-cell signaling domain) as described herein, including embodiments thereof, and/or a co-stimulatory domain as described herein, including embodiments thereof.

In some cases, an scFv as provided herein may be directly connected (e.g., covalently bound) to a transmembrane domain or may be connected (e.g., covalently bound) to the transmembrane domain through a hinge region.

A "hinge region" as provided herein is a polypeptide connecting an antigen-binding site domain (i.e., scFv) to a transmembrane domain. Any hinge region capable of connecting an scFv to a transmembrane domain is contemplated herein. In some cases, the hinge region is a polypeptide hinge region. In some cases, the polypeptide hinge region is a flexible hinge region. In some cases, the hinge region includes glycine and/or serine residues. In some cases, the hinge region is or includes an antibody hinge region or a portion thereof. In some cases, the hinge region includes an antibody Fc domain or a portion thereof (e.g., a portion comprising a hinge region). Non-limiting examples of suitable hinge regions contemplated herein include a IgG Fc, human IgG Fc, human IgG1 Fc, IgG4 Fc, and human IgG4 Fc, or a portion thereof (i.e., a portion thereof that includes the hinge region). In some cases, the hinge region is an IgG Fc or a portion thereof. In some cases, the hinge region is a human IgG Fc or a portion thereof. In some cases, the hinge region is an IgG1 Fc or a portion thereof. In some cases, the hinge region is a human IgG1 Fc, or a portion thereof. In some cases, the hinge region is an IgG4 Fc, or a portion thereof. In some cases, the hinge regions is an human IgG4 Fc, or a portion thereof. In some cases, a IgG Fe hinge is used to connect the binding site domain to the CAR backbone. In some cases, an IgG1 or IgG4 human Fe or a portion thereof comprising a hinge region include one or more mutations to reduce or prevent the binding to the corresponding Fc receptor. In some cases, an IgG1 or IgG4 human Fc or a portion thereof comprising a hinge region does not include a mutation to reduce or prevent the binding to the corresponding Fc receptor. In some cases, the length of a portion of a Fc domain can be of 229 amino acids, 129 amino acids, or less.

In some cases, the hinge region is about 229 amino acids in length. In some cases, the hinge region is 229 amino acids in length. In some cases, the hinge region is about 129 amino acids in length. In some cases, the hinge region is 129 amino acids in length. In some cases, the hinge region is between about 129 to about 229 amino acids in length. In some cases, the hinge region is less than about 229 amino acids in length. In some cases, the hinge region is less than 229 amino acids in length. In some cases, the hinge region is less than about 129 amino acids in length. In some cases, the hinge region is less than 129 amino acids in length. In some cases, the hinge region is at least 22 amino acids in length. In some cases, the hinge region is 22 amino acids in length. In some cases, the hinge region is about 25, 50, 75, 100, 125, 150, 175, 200, 225, or 250 amino acids in length. In some cases, the hinge region is about 25 amino acids in length. In some cases, the hinge region is about 50 amino acids in length. In some cases, the hinge region is about 75 amino acids in length. In some cases, the hinge region is about 100 amino acids in length. In some cases, the hinge region is about 125 amino acids in length. In some cases, the hinge region is about 150 amino acids in length. In some cases, the hinge region is about 175 amino acids in length. In some cases, the hinge region is about 200 amino acids in length. In some cases, the hinge region is about 225 amino acids in length. In some cases, the hinge region is about 250 amino acids in length. In some cases, the hinge region is 25 amino acids in length. In some cases, the hinge region is 50 amino acids in length. In some cases, the hinge region is 75 amino acids in length. In some cases, the hinge region is 100 amino acids in length. In some cases, the hinge region is 125 amino acids in length. In some cases, the hinge region is 150 amino acids in length. In some cases, the hinge region is 175 amino acids in length. In some cases, the hinge region is 200 amino acids in length. In some cases, the hinge region is 225 amino acids in length. In some cases, the hinge region is 250 amino acids in length.

In some cases, the hinge region is between about 22 to about 250 amino acids in length. In some cases, the hinge region is between about 25 to about 250 amino acids in length. In some cases, the hinge region is between about 50 to about 250 amino acids in length. In some cases, the hinge region is between about 75 to about 250 amino acids in length. In some cases, the hinge region is between about 100 to about 250 amino acids in length. In some cases, the hinge region is between about 125 to about 250 amino acids in length. In some cases, the hinge region is between about 150 to about 250 amino acids in length. In some cases, the hinge region is between about 175 to about 250 amino acids in length. In some cases, the hinge region is between about 200 to about 250 amino acids in length. In some cases, the hinge region is between about 225 to about 250 amino acids in length. In some cases, the hinge region is between about 22 to about 225 amino acids in length. In some cases, the hinge region is between about 22 to about 200 amino acids in length. In some cases, the hinge region is between about 22 to about 175 amino acids in length. In some cases, the hinge region is between about 22 to about 150 amino acids in length. In some cases, the hinge region is between about 22 to about 125 amino acids in length. In some cases, the hinge region is between about 22 to about 100 amino acids in length. In some cases, the hinge region is between about 22 to about 75 amino acids in length. In some cases, the hinge region is between about 22 to about 50 amino acids in length. In some cases, the hinge region is between about 22 to about 25 amino acids in length.

In some cases, the hinge region includes an Fc domain. In some cases, the hinge region includes an IgG Fc domain. In some cases, the hinge region is an IgG1 Fc or a fragment thereof. In some cases, the hinge region is a human IgG1 Fc or a fragment thereof. In some cases, the hinge region is an IgG4 Fc or a fragment thereof. In some cases, the hinge region is a human IgG4 Fc or a fragment thereof.

In some cases, the hinge region may be a mutated hinge region. In some cases, a mutated hinge region (e.g., Fc) may be useful, for example, to prevent the Fc from binding to its cognate Fc receptor. In some cases, the hinge region (e.g., IgG, human IgG Fc, IgG1 Fc, human IgG1 Fc, IgG4 Fc, human IgG4 Fc) includes no more than 5, 4, 3, 2, or 1 deletions. In some cases, the hinge region (e.g., IgG, human IgG Fc, IgG1 Fc, human IgG1 Fc, IgG4 Fc, human IgG4 Fc) includes no more than 5, 4, 3, 2, or 1 insertions. In some cases, the hinge region (e.g., IgG, human IgG Fc, IgG1 Fc, human IgG1 Fc, IgG4 Fc, human IgG4 Fc) does not include deletions. In some cases, the hinge region (e.g., IgG, human IgG Fc, IgG1 Fc, human IgG1 Fc, IgG4 Fc, human IgG4 Fc) does not include insertions. In some cases, the hinge region (e.g., IgG, human IgG Fc, IgG1 Fc, human IgG1 Fc, IgG4 Fc, human IgG4 Fc) includes substitutions that are conservative substitutions.

In some cases, a transmembrane domain as provided herein refers to a polypeptide forming part of (e.g., spanning) a biological membrane. In some cases, the transmembrane domain provided herein is capable of spanning a biological membrane (e.g., a cellular membrane) from one side of the membrane through to the other side of the membrane. In some cases, the transmembrane domain spans only a portion of the membrane, but is sufficient to anchor an antigen-binding domain to the membrane. In some cases, the transmembrane domain spans from the intracellular side to the extracellular side of a cellular membrane. In some cases, transmembrane domains may include non-polar, hydrophobic residues, which anchor the proteins provided herein including embodiments thereof in a biological membrane (e.g., cellular membrane of a T cell). Any transmembrane domain capable of anchoring the proteins provided herein including embodiments thereof is contemplated. Non-limiting examples of transmembrane domains include the transmembrane domains of CD28, CD8, CD4, or CD3-zeta (CD3ζ).

In some cases, the transmembrane domain includes a CD4 transmembrane domain or a variant thereof, a CD8 transmembrane domain or a variant thereof, a CD28 transmembrane domain or a variant thereof, or a CD3ζ transmembrane domain or a variant thereof. In some cases, recombinant protein such as a CAR (e.g., a cell expressing a CAR) comprises an intracellular co-stimulatory domain and/or an intracellular T-cell signaling domain.

In some cases, the transmembrane domain includes a CD4 transmembrane domain or a variant thereof. In some cases, the transmembrane domain includes a CD8 transmembrane domain or a variant thereof. In some cases, the transmembrane domain includes a CD28 transmembrane domain or a variant thereof. In some cases, the transmembrane domain includes a CD3ζ transmembrane domain or a variant thereof.

In some cases, the transmembrane domain is covalently bound to a heavy chain variable region of the scFv. In some cases, the transmembrane domain is covalently bound to a light chain variable region of the scFv. In some cases, the transmembrane domain is covalently bound to a heavy chain variable region of the scFv though a hinge region. In some cases, the transmembrane domain is covalently bound to a light chain variable region of the scFv through a hinge region. In some cases, a recombinant protein provided herein (such as a CAR, e.g., on the surface of a cell) comprises, from the N-terminal end to the C-terminal end a $V_H$, a $V_L$, and a transmembrane domain. In some cases, a recombinant protein provided herein (such as a CAR, e.g., on the surface of a cell) comprises, from the N-terminal end to the C-terminal end a $V_L$, a $V_H$, and a transmembrane domain. In some cases, a recombinant protein provided herein (such as a CAR, e.g., on the surface of a cell) comprises, from the N-terminal end to the C-terminal end a $V_H$, a linker, a $V_L$, and a transmembrane domain. In some cases, a recombinant protein provided herein (such as a CAR, e.g., on the surface of a cell) comprises, from the N-terminal end to the C-terminal end a $V_L$, a linker, a $V_H$, and a transmembrane domain. In some cases, a recombinant protein provided herein (such as a CAR, e.g., on the surface of a cell) comprises, from the N-terminal end to the C-terminal end a $V_H$, a linker, a $V_L$, a hinge region, and a transmembrane domain. In some cases, a recombinant protein provided herein (such as a CAR, e.g., on the surface of a cell) comprises, from the N-terminal end to the C-terminal end a $V_L$, a linker, a $V_H$, a hinge region, and a transmembrane domain. The VH, VL, linker, hinge region, and transmembrane domain referred to in this paragraph, refer to those disclosed herein, including embodiments thereof.

In some cases, the antigen-binding domain (e.g., the scFv) includes the CDR sequences of itolizumab. In some cases, the CDRs include the amino acid sequences set forth by SEQ ID NOs:28, 29, 30, 31, 32, and 33. In some cases, the CDRs are the amino acid sequences set forth by SEQ ID NOs: 28, 29, 30, 31, 32, and 33. In some cases, the CDRs specifically bind CD6. In some cases, the CDRs specifically bind CD6 with an affinity from between about $1 \times 10^{-6}$ to $1 \times 10^{-8}$. In some cases, the CDRs specifically bind CD6 with an affinity of equal to or less than about $1 \times 10^{-6}$ or $1 \times 10^{-7}$.

An "intracellular co-stimulatory signaling domain," "co-stimulatory signaling domain," or "intracellular co-stimulatory domain" as provided herein includes amino acid sequences capable of providing co-stimulatory signaling in response to binding of an antigen to the antigen-binding domain of the recombinant protein (e.g. CAR) provided herein including embodiments thereof. In some cases, the signaling of the co-stimulatory signaling domain results in production of cytokines and proliferation of a cell (e.g., a T cell) expressing the recombinant protein (e.g., CAR).

In some cases, the co-stimulatory domain is a CD28 intracellular co-stimulatory domain or a variant thereof, a 4-1BB intracellular co-stimulatory domain or a variant thereof, an ICOS intracellular co-stimulatory signaling domain or a variant thereof, an OX-40 intracellular co-stimulatory signaling domain or a variant thereof, a CTLA-4 intracellular co-stimulatory domain or a variant thereof, a PD-1 intracellular co-stimulatory domain or a variant thereof, or a GITR co-stimulatory domain or a variant thereof. In some cases, the co-stimulatory domain is a CD28 intracellular co-stimulatory domain (SEQ ID NO:7 or 8) or a variant thereof. In some cases, the co-stimulatory domain is an ICOS intracellular co-stimulatory signaling domain or a variant thereof. In some cases, the co-stimulatory domain is an OX-40 intracellular co-stimulatory signaling domain or a variant thereof. In some cases, the co-stimulatory domain is a CTLA-4 intracellular co-stimulatory domain (SEQ ID NO:17) or a variant thereof. In some cases, the co-stimulatory domain is a PD-1 intracellular co-stimulatory domain or a variant thereof. In some cases, the co-stimulatory domain is a GITR co-stimulatory domain or a variant thereof.

In some cases, a recombinant protein provided herein (such as a CAR, e.g., on the surface of a cell) comprises, from the N-terminal end to the C-terminal end a $V_H$, a $V_L$, a transmembrane domain, and a co-stimulatory domain. In some cases, a recombinant protein provided herein (such as a CAR, e.g., on the surface of a cell) comprises, from the N-terminal end to the C-terminal end a $V_L$, a $V_H$, a transmembrane domain, and a co-stimulatory domain. In some cases, a recombinant protein provided herein (such as a CAR, e.g., on the surface of a cell) comprises, from the N-terminal end to the C-terminal end a $V_H$, a linker, a $V_L$, a transmembrane domain, and a co-stimulatory domain. In some cases, a recombinant protein provided herein (such as a CAR, e.g., on the surface of a cell) comprises, from the N-terminal end to the C-terminal end a $V_L$, a linker, a $V_H$, a transmembrane domain, and a co-stimulatory domain. In some cases, a recombinant protein provided herein (such as a CAR, e.g., on the surface of a cell) comprises, from the N-terminal end to the C-terminal end a $V_H$, a linker, a $V_L$, a hinge region, a transmembrane domain, and a co-stimulatory domain. In some cases, a recombinant protein provided herein (such as a CAR, e.g., on the surface of a cell) comprises, from the N-terminal end to the C-terminal end a $V_L$, a linker, a $V_H$, a hinge region, a transmembrane domain, and a co-stimulatory domain. The $V_H$, $V_L$, linker, hinge region, transmembrane domain, and a co-stimulatory domain referred to in this paragraph, refer to those disclosed herein, including embodiments thereof.

An "intracellular T-cell signaling domain" as provided herein includes amino acid sequences capable of providing primary signaling in response to binding of an antigen to the antigen-binding domain of the recombinant protein (e.g. CAR) provided herein including embodiments thereof, including embodiments thereof. In some cases, the signaling of the intracellular T-cell signaling domain results in activation of the T cell expressing the same. In some cases, the signaling of the intracellular T-cell signaling domain results in proliferation (cell division) of a cell (e.g., a T cell) expressing the recombinant protein (e.g., CAR). In some cases, the signaling of the intracellular T-cell signaling domain results in expression by the T cell of proteins known in the art to characteristic of activated T cell (e.g., CTLA-4, PD-1, CD28, CD69).

In some cases, the intracellular T-cell signaling domain is a CD3ζ intracellular T-cell signaling domain.

In some cases, a recombinant protein provided herein (such as a CAR, e.g., on the surface of a cell) comprises, from the N-terminal end to the C-terminal end a $V_H$, a $V_L$, a transmembrane domain, a co-stimulatory domain, and an intracellular T-cell signaling domain. In some cases, a recombinant protein provided herein (such as a CAR, e.g., on the surface of a cell) comprises, from the N-terminal end to the C-terminal end a $V_L$, a $V_H$, a transmembrane domain, a co-stimulatory domain, and an intracellular T-cell signaling domain. In some cases, a recombinant protein provided herein (such as a CAR, e.g., on the surface of a cell) comprises, from the N-terminal end to the C-terminal end a $V_H$, a linker, a $V_L$, a transmembrane domain, a co-stimulatory domain, and an intracellular T-cell signaling domain. In some cases, a recombinant protein provided herein (such as a CAR, e.g., on the surface of a cell) comprises, from the N-terminal end to the C-terminal end a $V_L$, a linker, a $V_H$, a transmembrane domain, a co-stimulatory domain, and an intracellular T-cell signaling domain. In some cases, a recombinant protein provided herein (such as a CAR, e.g., on the surface of a cell) comprises, from the N-terminal end to the C-terminal end a $V_H$, a linker, a $V_L$, a hinge region, a transmembrane domain, a co-stimulatory domain, and an intracellular T-cell signaling domain. In some cases, a recombinant protein provided herein (such as a CAR, e.g., on the surface of a cell) comprises, from the N-terminal end to the C-terminal end a $V_L$, a linker, a $V_H$, a hinge region, a transmembrane domain, a co-stimulatory domain, and an intracellular T-cell signaling domain. The VH, VL, linker, hinge region, transmembrane domain, co-stimulatory domain, and intracellular T-cell signaling domain referred to in this paragraph, refer to those disclosed herein, including embodiments thereof.

In some cases, the T lymphocyte is a regulatory T lymphocyte (Treg). The category of effector T cell is a broad one that includes various T cell types that actively respond to a stimulus, such as co-stimulation. Effector T cells include helper, killer, regulatory, and potentially other T cell types. The regulatory T cells, formerly known as suppressor T cells, are a subpopulation of T cells which modulate the immune system, maintain tolerance to self-antigens, and prevent autoimmune disease. Tregs are immunosuppressive and generally suppress or downregulate induction and proliferation of effector T cells. In some cases, the effector T lymphocyte helper T cell. In some cases, the effector T lymphocyte is a killer T cell. In some cases, the effector T lymphocyte is a Treg.

In some cases, the Treg is a Treg that includes CD4positive-CD25high expression. In some cases, the Treg is a Treg that includes CD4positive-CD25high-CD127low or negative expression. In some cases, the Treg is a Treg that includes CD4positive-CD25high-CD6low or negative expression. In some cases, the Treg is a Treg that includes CD4positive-CD25high-CD127low or negative-CD6low or negative expression. In some cases, the Treg is a Treg that includes CD3positive-CD6low or negative expression. In some cases, the Treg is a Treg that includes CD4positive-CD6low or negative expression. In some cases, the Treg is a Treg that includes CD8positive-CD28low expression. In some cases, the Treg is a Treg that includes CD45RA+ expression. In some cases, the Treg is a Treg that does not include CD45RA+ expression. In some cases, the Treg is a Treg that includes FOXP3 demethylation. In some cases, the Treg is a Treg that does not include FOXP3 demethylation. In some cases, the Treg is a Treg that can be expanded either with IL-2 and/or rapamycin and/or retinoic acid. In some cases, the Treg is a Treg that can be expanded with IL-2 and/or rapamycin and/or retinoic acid. In some cases, the Treg is a Treg that can be expanded with IL-2. In some cases, the Treg is a Treg that can be expanded with rapamycin. In some cases, the Treg is a Treg that can be expanded with retinoic acid.

Determining "high" and "low" expression is well known in the art. A description of high and low expression of the markers referred to supra, and how high and low expression are determined and quantified, may be found, for example, in Putnam, A. L., T. M. Brusko, M. R. Lee, W. Liu, G. L. Szot, T. Ghosh, M. A. Atkinson and J. A. Bluestone. Expansion of human regulatory T-cells from patients with type 1 diabetes. Diabetes 58(3): 652-662, 2009; Bluestone J A, Buckner J H, Fitch M, Gitelman S E, Gupta S, Hellerstein M K, Herold K C, Lares A, Lee M R, Li K, Liu W, Long S A, Masiello L M, Nguyen V, Putnam A L, Rieck M, Sayre P H, Tang Q. Type 1 diabetes immunotherapy using polyclonal regulatory T cells. Sci Transl Med. 2015 Nov. 25; 7(315):315ra189; Fuchs, A., M. Gliwinski, N. Grageda, R. Spiering, A. K. Abbas, S. Appel, R. Bacchetta, M. Battaglia, D. Berglund, B. Blazar, J. A. Bluestone, M. Bornhauser, A. Ten Brinke, T. M. Brusko, N. Cools, M. C. Cuturi, E. Geissler, N. Giannoukakis, K. Golab, D. A. Hafler, S. M. van Ham, J. Hester, K. Hippen, M. Di Ianni, N. Ilic, J. Isaacs, F. Issa, D. Iwaszkiewicz-Grzes, E. Jaeckel, I. Joosten, D. Klatzmann, H. Koenen, C. van Kooten, O. Korsgren, K. Kretschmer, M. Levings, N. M. Marek-Trzonkowska, M. Martinez-Llordella, D. Miljkovic, K. H. G. Mills, J. P. Miranda, C. A. Piccirillo, A. L. Putnam, T. Ritter, M. G. Roncarolo, S. Sakaguchi, S. Sanchez-Ramon, B. Sawitzki, L. Sofronic-Milosavljevic, M. Sykes, Q. Tang, M. Vives-Pi, H. Waldmann, P. Witkowski, K. J. Wood, S. Gregori, C. M. U. Hilkens, G. Lombardi, P. Lord, E. M. Martinez-Caceres and P. Trzonkowski. Minimum Information about T Regulatory Cells: A Step toward Reproducibility and Standardization. Front Immunol 8: 1844, 2017; Duggleby, R., R. D. Danby, J. A. Madrigal and A. Saudemont. Clinical Grade Regulatory CD4(+) T Cells (Tregs): Moving Toward Cellular-Based Immunomodulatory Therapies. Front Immunol 9: 252, 2018; the entire contents of each of which are incorporated herein by reference in their entireties and for all purposes.

In some cases, an scFv (e.g., of a CAR) includes a light chain variable region set forth by SEQ ID NO:34. In some cases, the scFv includes a heavy chain variable region set forth by SEQ ID NO:35. In some cases, the scFv includes the sequence set forth by SEQ ID NO:38. In some cases, the scFv includes the sequence set forth by SEQ ID NO:39.

In some cases, an scFv (e.g., of a CAR) is oriented with a light chain variable region at the N-terminus followed by a heavy chain variable region. Alternatively, In some cases, the scFv is oriented with the heavy chain variable region at the N-terminus followed by the light chain variable region.

In some cases, the light chain variable region (VL) and the heavy chain variable region (VH) of the scFv are separated by a linker. In some cases, the linker comprises the sequence set forth by SEQ ID NO:36. In some cases, the linker comprises the sequence set forth by SEQ ID NO:37.

In some cases, the scFv amino acid sequence includes the sequence set forth by SEQ ID NO:38. In some cases, the scFv amino acid sequence includes the sequence set forth by SEQ ID NO:39. In some cases, the scFv amino acid sequence includes the sequence set forth by SEQ ID NO:40. In some cases, the scFv amino acid sequence includes the sequence set forth by SEQ ID NO:41.

In some cases, the light chain variable region is covalently bound to the transmembrane region through a hinge region. In some cases, the heavy chain variable region is covalently bound to the transmembrane region through a hinge region.

In some cases, the hinge region is a human IgG Fc. In some cases, the human IgG Fc is a human IgG4 Fc. In some cases, the human IgG Fc is a human IgG1 Fc.

In some cases, the co-stimulatory domain is a CD28 intracellular co-stimulatory domain or a variant thereof, a 4-1BB intracellular co-stimulatory domain or a variant thereof, an ICOS intracellular co-stimulatory signaling domain or a variant thereof, an OX-40 intracellular co-stimulatory signaling domain or a variant thereof, a CTLA-4 intracellular co-stimulatory signaling domain or a variant thereof, a PD-1 intracellular co-stimulatory signaling domain or a variant thereof, or a GITR intracellular co-stimulatory signaling domain or a variant thereof.

In some cases, the intracellular T-cell signaling domain is a CD3ζ intracellular T-cell signaling domain.

In some cases, the scFv comprises the CDR sequences set forth by SEQ ID NOs:28, 29, 30, 31, 32, and 33.

In an aspect is provided a T lymphocyte including the recombinant protein described herein including embodiments thereof. In some cases, the T lymphocyte is a regulatory T lymphocyte (Treg) as described herein, including embodiments thereof. CAR T cells may be produced using methods well known in the art. For example, T lymphocytes isolated from a subject (e.g. patient) or donor (e.g. healthy subject) may be transduced with a nucleic acid encoding a CAR. Introduction of the nucleic acid encoding the CAR may be accomplished by viral or non-viral methods as described surpa. It should be appreciated that T lymphocytes obtained from donors (i.e. allogenic T lymphocytes) may undergo gene editing, using gene editing techniques well known in the art (e.g. CRISPR), to eliminate immunogenic proteins (e.g. native T cell receptors). Following transduction, the T lymphocytes may be activated using, for example, artificial antigen-presenting cells (APCs; e.g. engineered cell lines or antibody-coated magnetic beads). Once activated, the T lymphocytes may be induced to develop into specialized T cell subtypes (e.g. T regulatory cells) by treating with, for example, specific mixtures of cytokines. Finally, the CAR T cell population may be expanded using techniques well known in the art.

In some cases, the T lymphocyte including the recombinant protein described herein, including embodiments thereof, is an autologous T lymphocyte (i.e. taken from the subject). In some cases, the T lymphocyte including the recombinant protein described herein, including embodiments thereof, is an allogenic T lymphocyte (i.e. a T lymphocyte not obtained from the subject.) In some cases, the allogenic T lymphocyte has undergone gene editing. In some cases, the allogeneic T lymphocyte is gene edited to eliminate expression of a native T cell receptor protein.

In an aspect, an isolated nucleic acid encoding a protein (e.g. a CAR) including a single chain variable fragment (scFv) targeted to CD6 and a transmembrane domain is provided.

In an aspect, a vector including the nucleic acid (e.g., isolated nucleic acid) as provided herein including embodiments thereof is provided. In some cases, the vector is a composition of matter that comprises an isolated nucleic acid and that can be used to deliver the isolated nucleic acid to the interior of a cell. Numerous vectors are known in the art including, but not limited to, linear polynucleotides, polynucleotides associated with ionic or amphiphilic compounds, plasmids, and viruses. In some cases, the vector is an autonomously replicating plasmid or a virus. In some cases, a compound that facilitates transfer of nucleic acid into cells, such as, for example, a polylysine compound, liposome, and the like is used. Examples of viral transfer vectors include, but are not limited to, adenoviral vectors, adeno-associated virus vectors, retroviral vectors, lentiviral vectors, and the like. In some cases, the vector is a plasmid. In some cases, the vector is extrachromosomal. In some cases, the vector integrates into the genome of a cell. In some cases, the vector is a viral vector. In some cases, the virus is a lentivirus or onco-retrovirus. In some cases, the virus is a lentivirus. In some cases, the virus is an onco-retrovirus. Any suitable virus for delivery of a vector including the nucleic acid provided herein (e.g., the isolated nucleic acid) to a cell is contemplated In some cases, the vector comprises a recombinant polynucleotide comprising expression control sequences operatively linked to the nucleotide sequence to be expressed. The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. The term "lentiviral vector" refers to a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic, include but are not limited to, e.g., the LENTIVECTOR® gene delivery technology from Oxford BioMedica, the LENTIMAX™ vector system from Lentigen and the like. Nonclinical types of lentiviral vectors are also available and would be known to one skilled in the art.

In an aspect is provided a T lymphocyte including a vector provided herein, including embodiments thereof.

Methods of Treatment

The compositions provided herein, including embodiments thereof, are contemplated as effective treatment of autoimmune diseases. Thus, in an aspect is provided a method of treating an autoimmune disease (e.g., Type I diabetes, Graft-versus-Host Disease, Lupus), the method including administering to a subject in need thereof an effective amount of a T-lymphocyte (e.g., a CART-cell) provided herein including embodiments thereof.

In some cases, the autoimmune disease is associated with reduced islet cell (e.g., beta cell) function, viability, or survival. In some cases, the autoimmune disease is Type I Diabetes. In some cases, the autoimmune disease is Graft-versus-Host Disease. In some cases, the autoimmune disease includes a subject's immune system attacking the subject's islet cells (e.g., beta cells).

In some cases, the T-Lymphocyte provided herein, including embodiments thereof, suppresses CD6+ T-lymphocytes. In some cases, the T-Lymphocyte provided herein, including embodiments thereof, suppresses CD6+ B-lymphocytes.

EXAMPLES

The following examples are intended to further illustrate certain embodiments of the disclosure. The examples are put forth so as to provide one of ordinary skill in the art and are not intended to limit its scope.

Example 1: CD6-Targeted CAR Expressed in Treg

Figure 6:
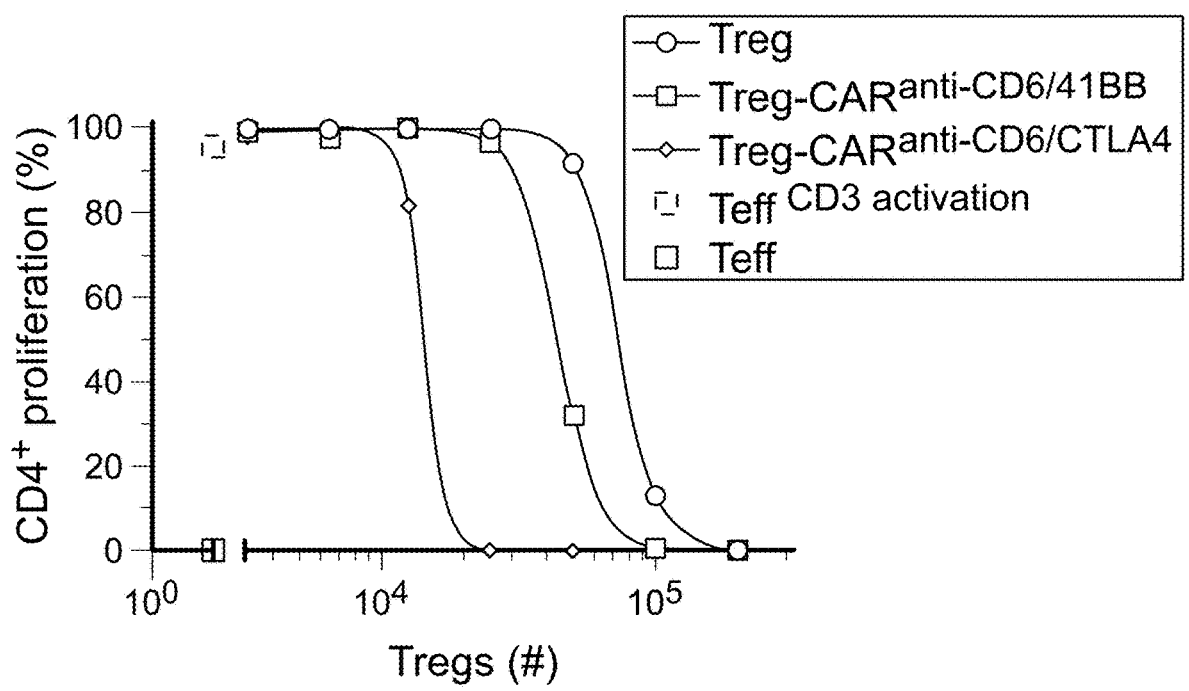
FIG. 6: Is a graph depicting inhibition of the effector T-cells (Teff) proliferation (IC50) by anti-CD6 CAR containing the CD137 (4-1BB) or the CD152 (CTLA-4) cytoplasmic domains, expressed in conventional CD4+ CD25hiCD127low/– T regulatory cells (Tregs) host. Circles, conventional Treg-MOCK:Teff-MOCK (IC50=73603); Squares, conventional Treg-CAR (anti-CD6/41BB):Teff-MOCK (IC50=43807); and Diamonds, conventional Treg-CAR (anti-CD6/CTLA4):Teff-MOCK (IC50=14286). Dark, single empty square, Teff-MOCK without stimulus and Light single empty square, Teff-MOCK with stimulus (anti-CD3 OKT3 mAb).
Figure 7:
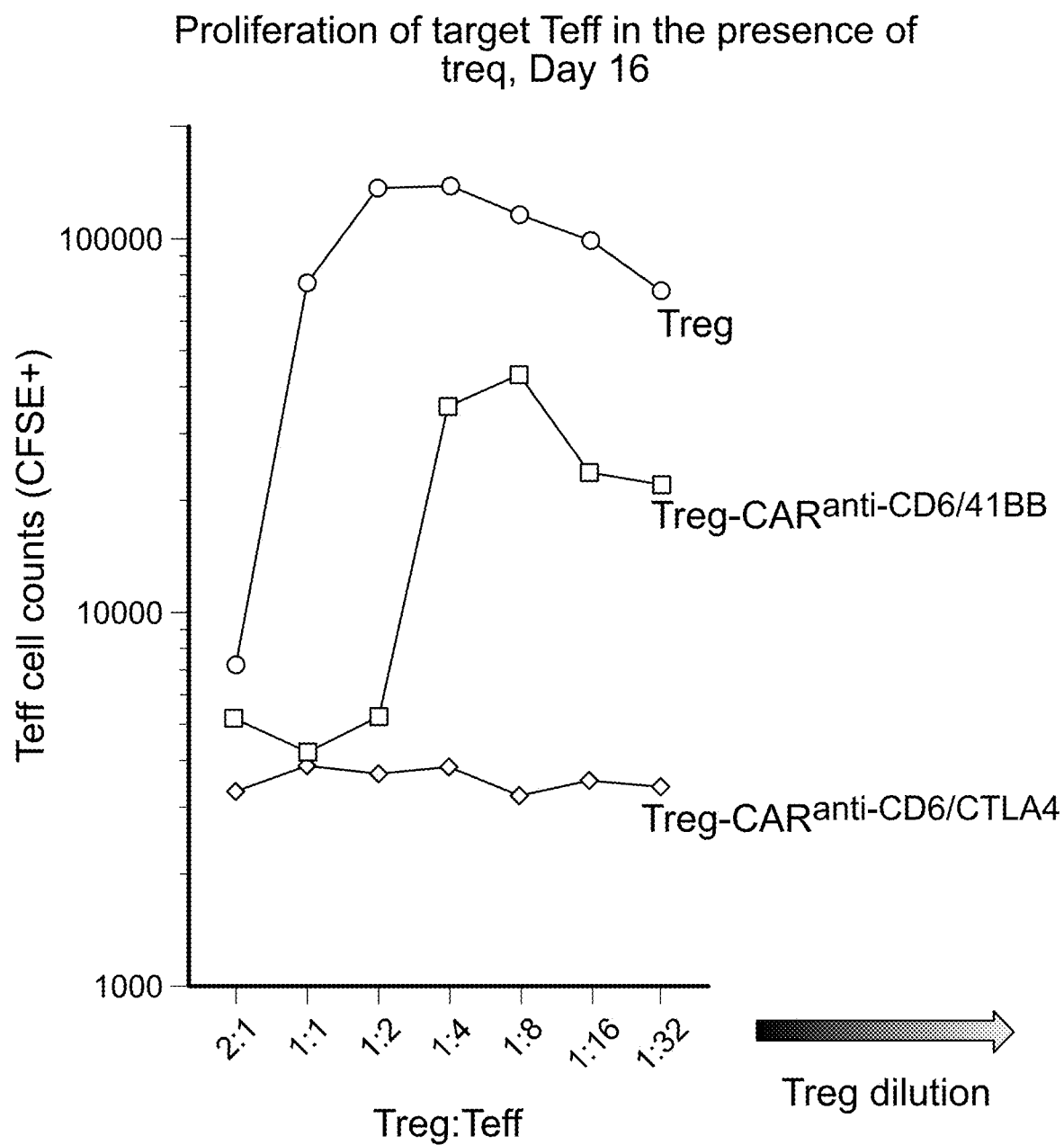
FIG. 7: Depicts the results of an experiment showing the impact of certain CD6 CAR on Teff proliferation.
Figure 8:
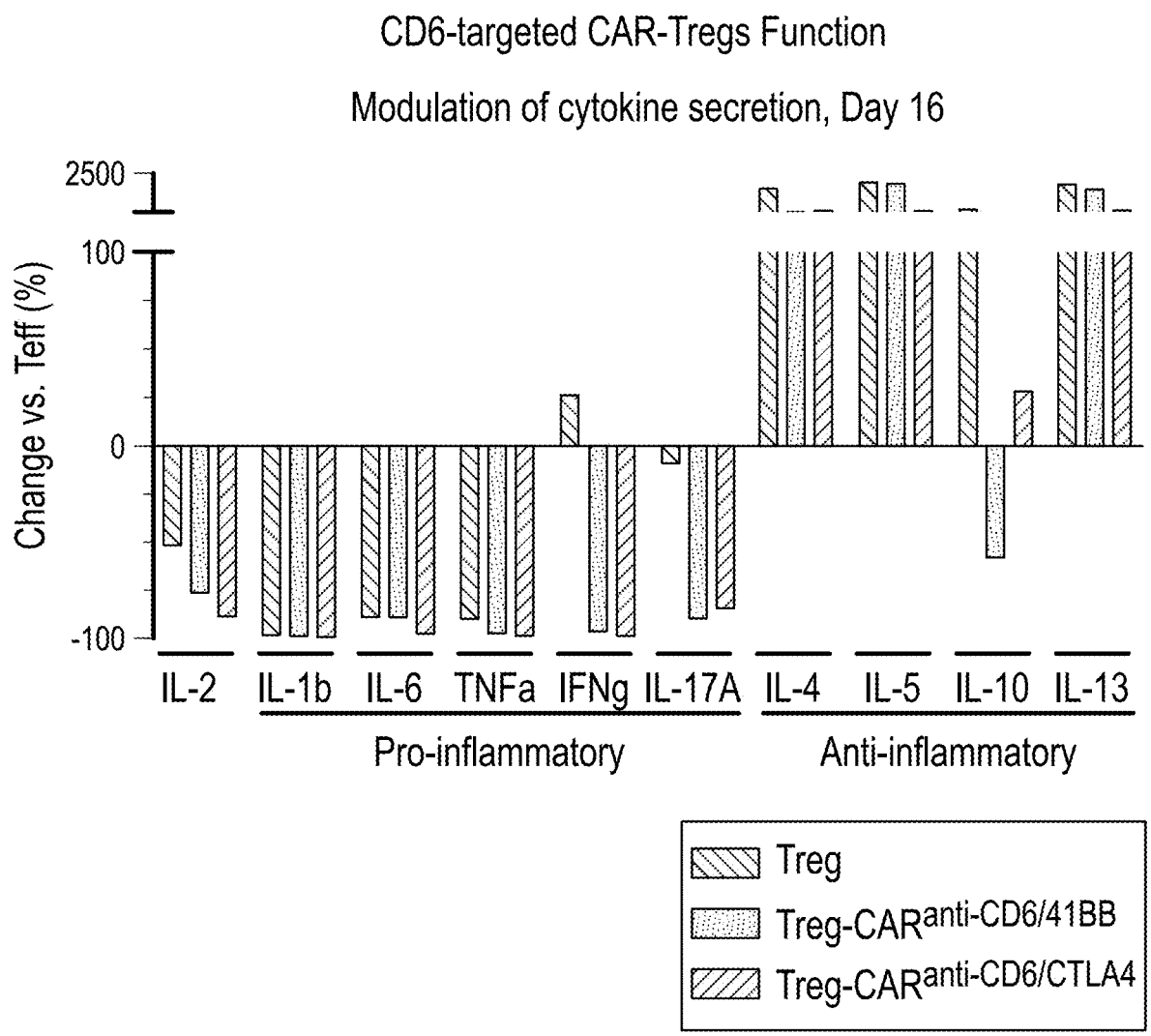
FIG. 8: Depicts the results of a study examining cytokine expression by Treg expressing certain CD6 CAR.
Figure 9:
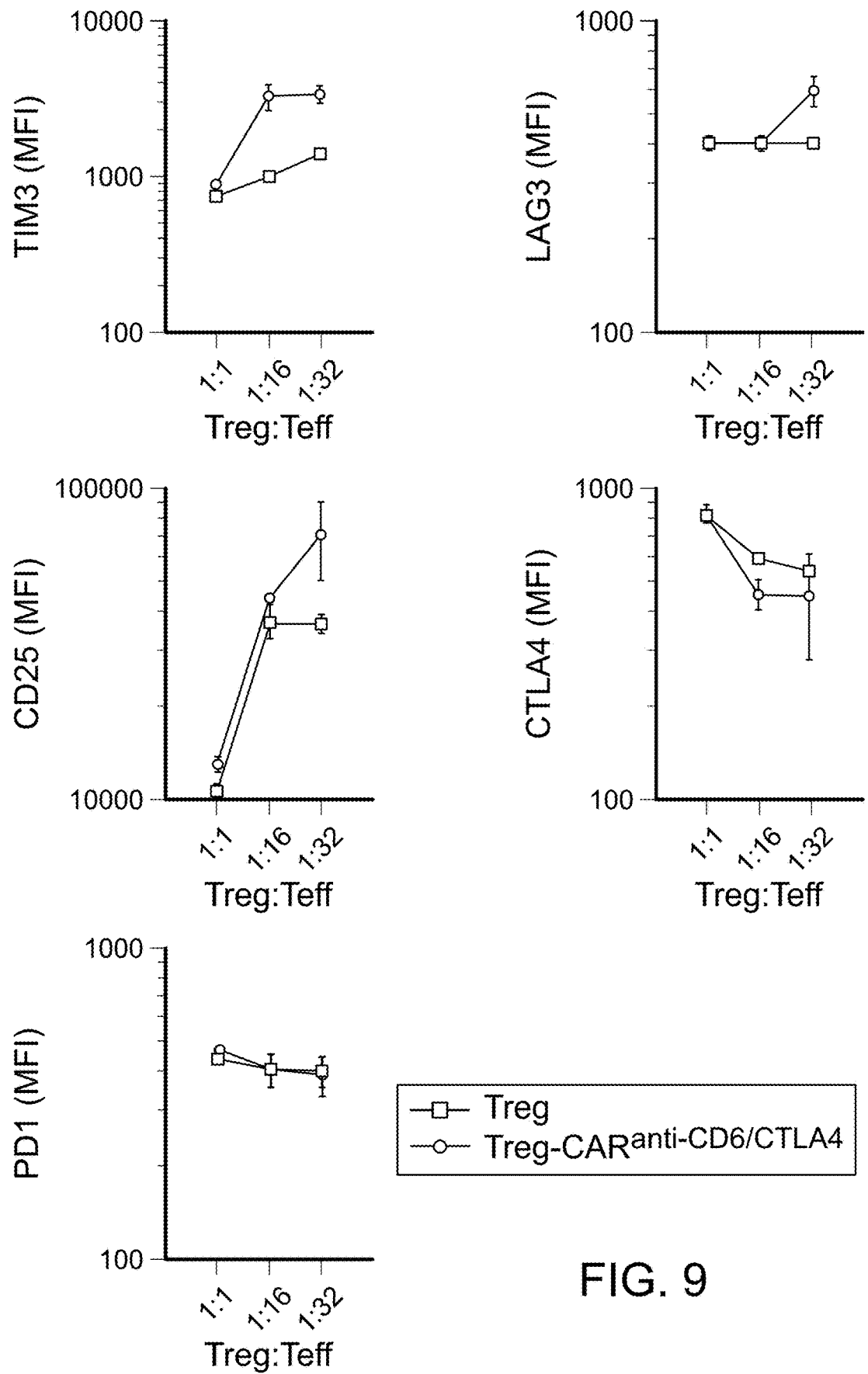
FIG. 9: Depicts the results of a study showing that Tregs expressing a CD6 CAR with a CTLA4 signaling domain can be cultured in the presence of Teff while expressing relatively low levels of exhaustion markers.

Various CAR that include an scFv derived from Itolizumab are depicted in FIG. 1 to FIG. 4. Each includes, in addition to an scFv in either the VL or VH orientation: a spacer derived from a portion of IgG4 with certain mutations, a CD4 transmembrane domain, either a CTLA4 or 4-1BB signaling domain, and a CD3 zeta signaling domain. CAR were prepared with the scFv in VH-VL or VL-VH orientations because yeast surface display technology previously suggested that a VH-VL scFv has an affinity for human CD6 that is similar to Itolizumab while a VL-VH scFv has lower affinity for human CD6 (Garner et al. (2018) *Immunology* 155:273). FIG. 5 is schematic depiction of a method used to isolate Tregs and Tregs that are $CD6^{low/-}$. Tregs can be isolated using any appropriate method (Fuchs et al. (2018) *Front Immunol.* 8:1844; Duggleby et al.)2018) *Front Immunol.* 9:252). A comparison of Treg, Treg expressing a CD6 CAR (CTLA4), and a CD6 CAR (4-1BB) shows that the CD6 CAR with CTLA4 signaling domain is superior for reducing Teff (CD4+) proliferation (FIG. 6). In addition, the CD6 CAR with CTLA4 signaling domain is superior for reducing target Teff proliferation (FIG. 7). The Treg expressing CD6 elicited anti-inflammatory cytokines (FIG. 8). As shown in FIG. 10, Tregs expressing a CD6 CAR with a CTLA4 signaling domain can be cultured in the presence of Teff while expressing relatively low levels of exhaustion markers.

Example 2: Expression of CD6-Targeted CAR

The CD6-targeted CAR can expressed in Tregs using a lentiviral vector. A suitable lentiviral vector is described in WO 2016/044811. The nucleotide sequence expressing the CAR can be in frame with a sequence encoding T2A (LEGGGEGRGSLLTCGDVEENPGPR; SEQ ID NO:71) and a sequence encoding a truncated CD19 receptor (MPP- PRLLFFLLFLTPMEVRPEEPLVVKVEEGD-
NAVLQCLKGTSDGPTQQLTWSRESPLKPF
LKLSLGLPGLGIHMRPLAIWLFIFNVSQQMGGFYL-
CQPGPPSEKAWQPGWTVNVEGSGELF RWNVSDLG-
GLGCGLKNRSSEGPSSPSGKLMSPKLYVWAKDRPEI-
WEGEPPCVPPRDSLNQS
LSQDLTMAPGSTLWLSCGVPPDSVSRG-
PLSWTHVHPKGPKSLLSLELKDDRPARDMWVME
TGLLLPRATAQDAGKYYCHRGNLTMSFHLEIT-
ARPVLWHWLLRTGGWKVSAVTLAYLIFC
LCSLVGILHLQRALVLRRKR; SEQ ID NO:73). When expressed in this manner, the CAR is coordinately expressed with a truncated CD19. This facilitates quantification of CAR-expressing cells using readily available CD19 antibodies.

FIG. 10 depicts the amino acid sequence of an alternative CD6 scFv that can replace the scFv in any of the constructs depicted on FIGS. 1-4.

| INFORMAL PARTIAL SEQUENCE LISTING |
|---|

```
SEQ ID NO: 1
MWLFEGITGLLTAALSGBPSPAPPDQLNTSSAESELWEPGERLPVRLTNGSSSCSGTVEVRL
EASWEPACGALWDSRAAEAVCRALGCGGAEAASQLAPPTPELPPPPAAGNTSVAANATLA
GAPALLCSGAEWRLCEVVEHACRSDGRRARVTCAENRALRLVDGGGACAGRVEMLEHGE
WGSVCDDTWDLEDAHVVCRQLGCGWAVQALPGLHFTPGRGPIHRDQVNCSGAEAYLWD
CPGLPGQHYCGHKEDAGAVCSEHQSWRLTGGADRCEGQVEVHFRGVWNTVCDSEWYPS
EAKVLCQSLGCGTAVERPKGLPHSLSGRMYYSCNGEELTLSNCSWRFNNSNLCSQSLAAR
VLCSASRSLHNLSTPEVPASVQTVTIESSVTVKIENKESRELMLLIPSIVLGILLLGSLIFIAFILL
RIKGKYALPVMVNHQHLPTTIPAGSNSYQPVPITIPKEVFMLPIQVQAPPPEDSDSGSDSDYE
HYDFSAQPPVALTTFYNSQRHRVTDEEVQQSRFQMPPLEEGLEELHASHIPTANPGHCITDP
PSLGPQYHPRSNSESSTSSGEDYCNSPKSKLPPWNPQVFSSERSSFLEQPPNLELAGTQPAFS
AGPPADDSSSTSSGEWYQNFQPPPQPPSEEQFGCPGSPSPQPDSTDNDDYDDISAA

SEQ ID NO: 2
MWLFEGITGLLTAALSGBPSPAPPD

][=-0987]
+LNTSSAESELWEPGERLPVRLTNGSSSCSGTVEVRLEASWEPACGALWDSRAAEAVCRAL
GCGGAEAASQLAPPTPELPPPPAAGNTSVAANATLAGAPALLCSGAEWRLCEVVEHACRS
DGRRARVTCAENRALRLVDGGGACAGRVEMLEHGEWGSVCDDTWDLEDAHVVCRQLGC
GWAVQALPGLHFTPGRGPIHRDQVNCSGAEAYLWDCPGLPGQHYCGHKEDAGAVCSEHQ
SWRLTGGADRCEGQVEVHFRGVWNTVCDSEWYPSEAKVLCQSLGCGTAVERPKGLPHSL
SGRMYYSCNGEELTLSNCSWRFNNSNLCSQSLAARVLCSASRSLHNLSTPEVPASVQTVTIE
SSVTVKIENKESRELMLLIPSIVLGILLLGSLIFIAFILLRIKGKYVFMLPIQVQAPPPEDSDSGS
DSDYEHYDFSAQPPVALTTFYNSQRHRVTDEEVQQSRFQMPPLEEGLEELHASHIPTANPG
HCITDPPSLGPQYHPRSNSESSTSSGEDYCNSPKSKLPPWNPQVFSSER
SSFLEQPPNLELAGTQPAFSGSPSPQPDSTDNDDYDDISAA

SEQ ID NO: 3
MWLFEGITGLLTAALSGBPSPAPPDQLNTSSAESELWEPGERLPVRLTNGSSSCSGTVEVRL
EASWEPACGALWDSRAAEAVCRALGCGGAEAASQLAPPTPELPPPPAAGNTSVAANATLA
GAPALLCSGAEWRLCEVVEHACRSDGRRARVTCAENRALRLVDGGGACAGRVEMLEHGE
WGSVCDDTWDLEDAHVVCRQLGCGWAVQALPGLHFTPGRGPIHRDQVNCSGAEAYLWD
CPGLPGQHYCGHKEDAGAVCSEHQSWRLTGGADRCEGQVEVHFRGVWNTVCDSEWYPS
EAKVLCQSLGCGTAVERPKGLPHSLSGRMYYSCNGEELTLSNCSWRFNNSNLCSQSLAAR
VLCSASRSLHNLSTPEVPASVQTVTIESSVTVKIENKESRELMLLIPSIVLGILLLGSLIFIAFILL
RIKGKYALPVMVNHQHLPTTIPAGSNSYQPVPITIPKEDSQRHRVTDEEVQQSRFQMPPLEE
GLEELHASHIPTANPGHCITDPPSLGPQYHPRSNSESSTSSGEDYCNSPKSKLPPWNPQVFSSE
RSSFLEQPPNLELAGTQPAFSGSPSPQPDSTDNDDYDDISAA

SEQ ID NO: 4
MLRLLLALNLFPSIQVTGNKILVKQSPMLVAYDNAVNLSWKHLCPSPLFPGPSKPFWVLVV
VGGVLACYSLLVTVAFIIFWVRSKRSRLLHSDYMNMTPRRPGPTRKHYQPYAPPRDFAAYR
S

SEQ ID NO: 5
MLRLLLALNLFPSIQVTGNKILVKQSPMLVAYDNAVNLSCKYSYNLFSREFRASLHKGLDS
AVEVCVVYGNYSQQLQVYSKTGFNCDGKLGNESVTFYLQNLYVNQTDIYFCKIEVMYPPP
YLDNEKSNGTIIHVKGKHLCPSPLFPGPSKPFWVLVVVGGVLACYSLLVTVAFIIFWVRSKR
SRLLHSDYMNMTPRRPGPTRKHYQPYAPPRDFAAYRS

SEQ ID NO: 6
MLRLLLALNLFPSIQVTGNKILVKQSPMLVAYDNAVNLSCKYSYNLFSREFRASLHKGLDS
AVEVCVVYGNYSQQLQVYSKTGFNCDGKLGNESVTFYLQNLYVNQTDIYFCKIEVMYPPP
YLDNEKSNGTIIHVKGKHLCPSPLFPGPSKPFWVLVVVGGVLACYSLLVTVAFIIFWVRSKR
SRLLHSDYMNMTPRRPGPTRKHYQPYAPPRDFAAYRS

SEQ ID NO: 7
RSKRSRGGHSDYMNMTPRRPGPTRKHYQPYAPPRDFAAYRS

SEQ ID NO: 8
RSKRSRLLHSDYMNMTPRRPGPTRKHYQPYAPPRDFAAYRS

SEQ ID NO: 9
MNRGVPFRHLLLVLQLALLPAATQGKKVVLGKKGDTVELTCTASQKKSIQFHWKNSNQIK
ILGNQGSFLTKGPSKLNDRADSRRSLWDQGNFPLIIKNLKIEDSDTYICEVEDQKEEVQLLVF
GLTANSDTHLLQGQSLTLTLESPPGSSPSVQCRSPRGKNIQGGKTLSVSQLELQDSGTWTCT
```

INFORMAL PARTIAL SEQUENCE LISTING

VLQNQKKVEFKIDIVVLAFQKASSIVYKKEGEQVEFSFPLAFTVEKLTGSGELWWQAERAS
SSKSWITFDLKNKEVSVKRVTQDPKLQMGKKLPLHLTLPQALPQYAGSGNLTLALEAKTG
KLHQEVNLVVMRATQLQKNLTCEVWGPTSPKLMLSLKLENKEAKVSKREKAVWVLNPEA
GMWQCLLSDSGQVLLESNIKVLPTWSTPVQPMALIVLGGVAGLLLFIGLGIFFCVRCRHRRR
QAERMSQIKRLLSEKKTCQCPHRFQKTCSPI

SEQ ID NO: 10
MPTPLVHPHLPISSPRVSPFPPPAFQKASSIVYKKEGEQVEFSFPLAFTVEKLTGSGELWWQA
ERASSSKSWITFDLKNKEVSVKRVTQDPKLQMGKKLPLHLTLPQALPQYAGSGNLTLALEA
KTGKLHQEVNLVVMRATQLQKNLTCEVWGPTSPKLMLSLKLENKEAKVSKREKAVWVL
NPEAGMWQCLLSDSGQVLLESNIKVLPTWSTPVQPMALIVLGGVAGLLLFIGLGIFFCVRCR
HRRRQAERMSQIKRLLSEKKTCQCPHRFQKTCSPI

SEQ ID NO: 11
MGKKLPLHLTLPQALPQYAGSGNLTLALEAKTGKLHQEVNLVVMRATQLQKNLTCEVWG
PTSPKLMLSLKLENKEAKVSKREKAVWVLNPEAGMWQCLLSDSGQVLLESNIKVLPTWST
PVQPMALIVLGGVAGLLLFIGLGIFFCVRCRHRRRQAERMSQIKRLLSEKKTCQCPHRFQKT
CSPI

SEQ ID NO: 12
MGKKLPLHLTLPQALPQYAGSGNLTLALEAKTGKLHQEVNLVVMRATQLQKNLTCEVWG
PTSPKLMLSLKLENKEAKVSKREKAVWVLNPEAGMWQCLLSDSGQVLLESNIKVLPTWST
PVQPMALIVLGGVAGLLLFIGLGIFFCVRCRHRRRQAERMSQIKRLLSEKKTCQCPHRFQKT
CSPI

SEQ ID NO: 13
MGKKLPLHLTLPQALPQYAGSGNLTLALEAKTGKLHQEVNLVVMRATQLQKNLTCEVWG
PTSPKLMLSLKLENKEAKVSKREKAVWVLNPEAGMWQCLLSDSGQVLLESNIKVLPTWST
PVQPMALIVLGGVAGLLLFIGLGIFFCVRCRHRRRQAERMSQIKRLLSEKKTCQCPHRFQKT
CSPI

SEQ ID NO: 14
KRGRKKLLYIFKQPFMRPVQTTQEEDGCSCRFPEEEEGGCEL

SEQ ID NO: 15
MGNSCYNIVATLLLVLNFERTRSLQDPCSNCPAGTFCDNNRNQICSPCPPNSFSSAGGQRTC
DICRQCKGVFRTRKECSSTSNAECDCTPGFHCLGAGCSMCEQDCKQGQELTKKGCKDCCF
GTFNDQKRGICRPWTNCSLDGKSVLVNGTKERDVVCGPSPADLSPGASSVTPPAPAREPGH
SPQIISFFLALTSTALLFLLFFLTLRFSVVKRGRKKLLYIFKQPFMRPVQTTQEEDGCSCRFPE
EEEGGCEL

SEQ ID NO: 16
MKSGLWYFFLFCLRIKVLTGEINGSANYEMFIFHNGGVQILCKYPDIVQQFKMQLLKGGQIL
CDLTKTKGSGNTVSIKSLKFCHSQLSNNSVSFFLYNLDHSHANYYFCNLSIFDPPPFKVTLTG
GYLHIYESQLCCQLKFWLPIGCAAFVVVCILGCILICWLTKKKYSSSVHDPNGEYMFMRAV
NTAKKSRLTDVTL

SEQ ID NO: 17
AVSLSKMLKKRSPLTTGVYVKMPPTEPECEKQFQPYFIPIN

SEQ ID NO: 18 (VL NA)
GACATCCAAATGACACAAAGTCCTAGCTCTCTCTCAGCAAGTGTTGGCGACCGTGTGAC
CATCACATGTAAAGCTTCAAGGGATATTCGCAGCTACCTGACTTGGTACCAACAAAAGC
CCGGAAAAGCGCCTAAAACGCTTATTTACTATGCCACCAGCCTCGCAGATGGTGTCCCC
TCCAGATTTTCTGGATCGGGATCAGGGCAAGATTATAGTCTTACGATATCGAGTCTTGA
GTCGGACGATACTGCCACATACTACTGCTTACAGCACGGGGAAAGCCCATTCACATTCG
GAAGTGGTACGAAACTCGAGATCAAACGGGCA

SEQ ID NO: 19 (VH NA)
GAAGTCCAATTGGTCGAGAGCGGAGGTGGGCTTGTTAAACCAGGAGGCAGTTTAAAAT
TATCATGTGCTGCCTCGGGTTTCAAGTTCTCGCGGTATGCTATGTCCTGGGTACGCCAA
GCACCTGGAAAGCGTTTAGAATGGGTGGCCACAATTAGTAGTGGTGGTTCATATATATA
TTATCCCGACTCCGTCAAAGGAAGGTTCACGATTTCAAGGGACAATGTGAAGAACACC
CTCTACTTACAGATGAGTAGTCTGCGTTCTGAGGATACCGCTATGTACTACTGTGCTCG
GAGAGATTACGATCTGGATTATTTCGACAGCTGGGGTCAGGGCACACTCGTTACAGTAT
CCTCG

SEQ ID NO: 20 (VH CDR1 NA)
GTCCAACTTGTTGAATCAGGTGGGGGGCTGGTCAAACCCGGGGGCTCTCTGAAACTAA
GT

SEQ ID NO: 21 (VH CDR2 NA)
TTCTCTCGGTACGCTATGTCGTGGGTCAGACAAGCGCCCGGCAAA

SEQ ID NO: 22 (VH CDR3 NA)
CGTGATTATGATCTAGACTACTTTGACTCCTGGGGTCAAGGTACGCTCGTGACGGTT

-continued

INFORMAL PARTIAL SEQUENCE LISTING

SEQ ID NO: 23
MALIVLGGVAGLLLFIGLGIFF

SEQ ID NO: 24
ATGGCCCTGATTGTGCTGGGGGGCGTCGCCGGCCTCCTGCTTTTCATTGGGCTAGGCAT
CTTCTTC

SEQ ID NO: 25
IYIWAPLAGTCGVLLLSLVIT

SEQ ID NO: 26 (Linker 18 NA)
GGGTCAACGTCGGGCGGGGGTTCCGGTGGAGGAAGTGGAGGTGGTGGAAGTTCT SEQ ID NO: 27 (Linker 20 NA)
GGCGGCGGCGGAAGTGGCGGCGGCGGCTCAGGCGGGGGGGGTTCTGGGGGCGGCGGT
TCA

SEQ ID NO: 28 (VH CDR1 AA)
VQLVESGGGLVKPGGSLKLS

SEQ ID NO: 29 (VH CDR2 AA)
FSRYAMSWVRQAPGK

SEQ ID NO: 30 (VH CDR3 AA)
RDYDLDYFDSWGQGTLVTV

SEQ ID NO: 31 (VL CDR1 AA)
CWLTKKKYSSSVHDPNGEYMFMRAVNTAKKSRLTDVTL

SEQ ID NO: 32
ALYLLRRDQRLPPDAHKPPGGGSFRTPIQEEQADAHSTLAKI

SEQ ID NO: 33 ((VL CDR3 AA)
CSRAARGTIGARRTGQPLKEDPSAVPVFSVDYGELDFQWREKTPEPPVPCVPEQTEYATIVF
PSGMGTSSPARRGSADGPRSAQPLRPEDGHCSWPL

SEQ ID NO: 34 (VL AA)
DIQMTQSPSSLSASVGDRVTITCKASRDIRSYLTWYQQKPGKAPKTLIYYATSLADGVPSRF
SGSGSGQDYSLTISSLESDDTATYYCLQHGESPFTFGSGTKLEIKRA

SEQ ID NO: 35 (VH AA)
EVQLVESGGGLVKPGGSLKLSCAASGFKFSRYAMSWVRQAPGKRLEWVATISSGGSYIYYP
DSVKGRFTISRDNVKNTLYLQMSSLRSEDTAMYYCARRDYDLDYFDSWGQGTLVTVSS

SEQ ID NO: 36 (Linker 18 AA)
GSTSGGGSGGGSGGGGSS

SEQ ID NO: 37 (Linker 20 AA)
GGGGSGGGGSGGGGSGGGGS

SEQ ID NO: 38 (Full scFv (VH-VL) linker 18)
EVQLVESGGGLVKPGGSLKLSCAASGFKFSRYAMSWVRQAPGKRLEWVATISSGGSYIYYP
DSVKGRFTISRDNVKNTLYLQMSSLRSEDTAMYYCARRDYDLDYFDSWGQGTLVTVSS
GSTSGGGSGGGSGGGSSDIQMTQSPSSLSASVGDRVTITCKASRDIRSYLTWYQQKPGKAP
KTLIYYATSLADGVPSRFSGSGSGQDYSLTISSLESDDTATYYCLQHGESPFTFGSGTKLEIK
RA SEQ ID NO: 39 (Full scFv (VH-VL) linker 20)
EVQLVESGGGLVKPGGSLKLSCAASGFKFSRYAMSWVRQAPGKRLEWVATISSGGSYIYYP
DSVKGRFTISRDNVKNTLYLQMSSLRSEDTAMYYCARRDYDLDYFDSWGQGTLVTVSS
GGGGSGGGGSGGGGSGGGGSDIQMTQSPSSLSASVGDRVTITCKASRDIRSYLTWYQQKPG
KAPKTLIYYATSLADGVPSRFSGSGSGQDYSLTISSLESDDTATYYCLQHGESPFTFGSGTKL
EIKRA SEQ ID NO: 40 (Full scFv (VL-VH) linker 18 AA)
DIQMTQSPSSLSASVGDRVTITCKASRDIRSYLTWYQQKPGKAPKTLIYYATSLADGVPSRF
SGSGSGQDYSLTISSLESDDTATYYCLQHGESPFTFGSGTKLEIKRAGSTSGGGSGGGSGGG
GSSEVQLVESGGGLVKPGGSLKLSCAASGFKFSRYAMSWVRQAPGKRLEWVATISSGGSYI
YYPDSVKGRFTISRDNVKNTLYLQMSSLRSEDTAMYYCARRDYDLDYFDSWGQGTLVTVS
S SEQ ID NO: 41 (Full scFv (VL-VH) linker 20 AA)
DIQMTQSPSSLSASVGDRVTITCKASRDIRSYLTWYQQKPGKAPKTLIYYATSLADGVPSRF
SGSGSGQDYSLTISSLESDDTATYYCLQHGESPFTFGSGTKLEIKRAGGGGSGGGGSGGGGS
GGGGSEVQLVESGGGLVKPGGSLKLSCAASGFKFSRYAMSWVRQAPGKRLEWVATISSGG
SYIYYPDSVKGRFTISRDNVKNTLYLQMSSLRSEDTAMYYCARRDYDLDYFDSWGQGTLV
TVSS

INFORMAL PARTIAL SEQUENCE LISTING

SEQ ID NO: 42 (Full scFv (VH-VL) linker 18 NA)
GAAGTCCAATTGGTCGAGAGCGGAGGTGGGCTTGTTAAACCAGGAGGCAGTTTAAAAT
TATCATGTGCTGCCTCGGGTTTCAAGTTCTCGCGGTATGCTATGTCCTGGGTACGCCAA
GCACCTGGAAAGCGTTTAGAATGGGTGGCCACAATTAGTAGTGGTGGTTCATATATATA
TTATCCCGACTCCGTCAAAGGAAGGTTCACGATTTCAAGGGACAATGTGAAGAACACC
CTCTACTTACAGATGAGTAGTCTGCGTTCTGAGGATACCGCTATGTACTACTGTGCTCG
GAGAGATTACGATCTGGATTATTTCGACAGCTGGGGTCAGGGCACACTCGTTACAGTAT
CCTCGGGGTCAACGTCGGGCGGGGGTTCCGGTGGAGGAAGTGGAGGTGGTGGAAGTTC
TGACATCCAAATGACACAAAGTCCTAGCTCTCTCTCAGCAAGTGTTGGCGACCGTGTGA
CCATCACATGTAAAGCTTCAAGGGATATTCGCAGCTACCTGACTTGGTACCAACAAAAG
CCCGGAAAAGCGCCTAAAACGCTTATTTACTATGCCACCAGCCTCGCAGATGGTGTCCC
CTCCAGATTTTCTGGATCGGGATCAGGGCAAGATTATAGTCTTACGATATCGAGTCTTG
AGTCGGACGATACTGCCACATACTACTGCTTACAGCACGGGGAAAGCCCATTCACATTC
GGAAGTGGTACGAAACTCGAGATCAAACGGGCA SEQ ID NO: 43 (Full scFv (VH-VL) linker 20 NA)
GAAGTCCAATTGGTCGAGAGCGGAGGTGGGCTTGTTAAACCAGGAGGCAGTTTAAAAT
TATCATGTGCTGCCTCGGGTTTCAAGTTCTCGCGGTATGCTATGTCCTGGGTACGCCAA
GCACCTGGAAAGCGTTTAGAATGGGTGGCCACAATTAGTAGTGGTGGTTCATATATATA
TTATCCCGACTCCGTCAAAGGAAGGTTCACGATTTCAAGGGACAATGTGAAGAACACC
CTCTACTTACAGATGAGTAGTCTGCGTTCTGAGGATACCGCTATGTACTACTGTGCTCG
GAGAGATTACGATCTGGATTATTTCGACAGCTGGGGTCAGGGCACACTCGTTACAGTAT
CCTCGGGCGGCGGCGGAAGTGGCGGCGGCGGCTCAGGCGGGGGGGGTTCTGGGGCG
GCGGTTCAGACATCCAAATGACACAAAGTCCTAGCTCTCTCTCAGCAAGTGTTGGCGAC
CGTGTGACCATCACATGTAAAGCTTCAAGGGATATTCGCAGCTACCTGACTTGGTACCA
ACAAAAGCCCGGAAAAGCGCCTAAAACGCTTATTTACTATGCCACCAGCCTCGCAGAT
GGTGTCCCCTCCAGATTTTCTGGATCGGGATCAGGGCAAGATTATAGTCTTACGATATC
GAGTCTTGAGTCGGACGATACTGCCACATACTACTGCTTACAGCACGGGGAAAGCCCA
TTCACATTCGGAAGTGGTACGAAACTCGAGATCAAACGGGCA SEQ ID NO: 44 (Full scFv (VL-VH) linker 18 NA)
GACATCCAAATGACACAAAGTCCTAGCTCTCTCTCAGCAAGTGTTGGCGACCGTGTGAC
CATCACATGTAAAGCTTCAAGGGATATTCGCAGCTACCTGACTTGGTACCAACAAAAGC
CCGGAAAAGCGCCTAAAACGCTTATTTACTATGCCACCAGCCTCGCAGATGGTGTCCCC
TCCAGATTTTCTGGATCGGGATCAGGGCAAGATTATAGTCTTACGATATCGAGTCTTGA
GTCGGACGATACTGCCACATACTACTGCTTACAGCACGGGGAAAGCCCATTCACATTCG
GAAGTGGTACGAAACTCGAGATCAAACGGGCAGGGTCAACGTCGGGCGGGGGTTCCGG
TGGAGGAAGTGGAGGTGGTGGAAGTTCTGAAGTCCAATTGGTCGAGAGCGGAGGTGGG
CTTGTTAAACCAGGAGGCAGTTTAAAATTATCATGTGCTGCCTCGGGTTTCAAGTTCTC
GCGGTATGCTATGTCCTGGGTACGCCAAGCACCTGGAAAGCGTTTAGAATGGGTGGCC
ACAATTAGTAGTGGTGGTTCATATATATATTATCCCGACTCCGTCAAAGGAAGGTTCAC
GATTTCAAGGGACAATGTGAAGAACACCCTCTACTTACAGATGAGTAGTCTGCGTTCTG
AGGATACCGCTATGTACTACTGTGCTCGGAGAGATTACGATCTGGATTATTTCGACAGC
TGGGGTCAGGGCACACTCGTTACAGTATCCTCG SEQ ID NO: 45 (Full scFv (VL-VH) linker 20 NA)
GACATCCAAATGACACAAAGTCCTAGCTCTCTCTCAGCAAGTGTTGGCGACCGTGTGAC
CATCACATGTAAAGCTTCAAGGGATATTCGCAGCTACCTGACTTGGTACCAACAAAAGC
CCGGAAAAGCGCCTAAAACGCTTATTTACTATGCCACCAGCCTCGCAGATGGTGTCCCC
TCCAGATTTTCTGGATCGGGATCAGGGCAAGATTATAGTCTTACGATATCGAGTCTTGA
GTCGGACGATACTGCCACATACTACTGCTTACAGCACGGGGAAAGCCCATTCACATTCG
GAAGTGGTACGAAACTCGAGATCAAACGGGCAGGCGGCGGCGGAAGTGGCGGCGGCG
GCTCAGGCGGGGGGGGTTCTGGGGCGGCGGTTCAGAAGTCCAATTGGTCGAGAGCGG
AGGTGGGCTTGTTAAACCAGGAGGCAGTTTAAAATTATCATGTGCTGCCTCGGGTTTCA
AGTTCTCGCGGTATGCTATGTCCTGGGTACGCCAAGCACCTGGAAAGCGTTTAGAATGG
GTGGCCACAATTAGTAGTGGTGGTTCATATATATATTATCCCGACTCCGTCAAAGGAAG
GTTCACGATTTCAAGGGACAATGTGAAGAACACCCTCTACTTACAGATGAGTAGTCTGC
GTTCTGAGGATACCGCTATGTACTACTGTGCTCGGAGAGATTACGATCTGGATTATTTC
GACAGCTGGGGTCAGGGCACACTCGTTACAGTATCCTCG SEQ ID NO: 46
MALPVTALLLPLALLLHAARPSQFRVSPLDRTWNLGETVELKCQVLLSNPTSGCSWLFQPR
GAAASPTFLLYLSQNKPKAAEGLDTQRFSGKRLGDTFVLTLSDFRRENEGYYFCSALSNSIM
YFSHFVPVFLPAKPTTTPAPRPPTPAPTIASQPLSLRPEACRPAAGGAVHTRGLDFACDIYIW
APLAGTCGVLLLSLVITLYCNHRNRRRVCKCPRPVVKSGDKPSLSARYV SEQ ID NO: 47
MALPVTALLLPLALLLHAARPSQFRVSPLDRTWNLGETVELKCQVLLSNPTSGCSWLFQPR
GAAASPTFLLYLSQNKPKAAEGLDTQRFSGKRLGDTFVLTLSDFRRENEGYYFCSALSNSIM
YFSHFVPVFLPAKPTTTPAPRPPTPAPTIASQPLSLRPEACRPAAGGAGNRRRVCKCPRPVVK
SGDKPSLSARYV

INFORMAL PARTIAL SEQUENCE LISTING

SEQ ID NO: 48
MALPVTALLLPLALLLHAARPSQFRVSPLDRTWNLGETVELKCQVLLSNPTSGCSWLFQPR
GAAASPTFLLYLSQNKPKAAEGLDTQRFSGKRLGDTFVLTLSDFRRENEGYYFCSALSNSIM
YFSHFVPVFLPAKPTTTPAPRPPTPAPTIASQPLSLRPEACRPAAGGAVHTRGLDFACDIYIW
APLAGTCGVLLLSLVITLYCNHRNRRRVCKCPRPVVKSGDKPSLSARYV

SEQ ID NO: 49
MRPRLWLLLAAQLTVLHGNSVLQQTPAYIKVQTNKMVMLSCEAKISLSNMRIYWLRQRQ
APSSDSHHEFLALWDSAKGTIHGEEVEQEKIAVFRDASRFILNLTSVKPEDSGIYFCMIVGSP
ELTFGKGTQLSVVDFLPTTAQPTKKSTLKKRVCRLPRPETQKGPLCSPITLGLLVAGVLVLL
VSLGVAIHLCCRRRRARLRFMKQKFNIVCLKISGFTTCCCFQILQMSREYGFGVLLQKDIGQ

SEQ ID NO: 50
MRPRLWLLLAAQLTVLHGNSVLQQTPAYIKVQTNKMVMLSCEAKISLSNMRIYWLRQRQ
APSSDSHHEFLALWDSAKGTIHGEEVEQEKIAVFRDASRFILNLTSVKPEDSGIYFCMIVGSP
ELTFGKGTQLSVVDFLPTTAQPTKKSTLKKRVCRLPRPETQKGLKGKVYQEPLSPNACMDT
TAILQPHRSCLTHGS

SEQ ID NO: 51
MRPRLWLLLAAQLTVLHGNSVLQQTPAYIKVQTNKMVMLSCEAKISLSNMRIYWLRQRQ
APSSDSHHEFLALWDSAKGTIHGEEVEQEKIAVFRDASRFILNLTSVKPEDSGIYFCMIVGSP
ELTFGKGTQLSVVDFLPTTAQPTKKSTLKKRVCRLPRPETQKGPLCSPITLGLLVAGVLVLL
VSLGVAIHLCCRRRRARLRFMKQPQGEGISGTFVPQCLHGYYSNTTTSQKLLNPWILKT

SEQ ID NO: 52
MRPRLWLLLAAQLTVLHGNSVLQQTPAYIKVQTNKMVMLSCEAKISLSNMRIYWLRQRQ
APSSDSHHEFLALWDSAKGTIHGEEVEQEKIAVFRDASRFILNLTSVKPEDSGIYFCMIVGSP
ELTFGKGTQLSVVDFLPTTAQPTKKSTLKKRVCRLPRPETQKGRRRRARLRFMKQPQGEGI
SGTFVPQCLHGYYSNTTTSQKLLNPWILKT

SEQ ID NO: 53
MRPRLWLLLAAQLTVLHGNSVLQQTPAYIKVQTNKMVMLSCEAKISLSNMRIYWLRQRQ
APSSDSHHEFLALWDSAKGTIHGEEVEQEKIAVFRDASRFILNLTSVKPEDSGIYFCMIVGSP
ELTFGKGTQLSVVDFLPTTAQPTKKSTLKKRVCRLPRPETQKGPLCSPITLGLLVAGVLVLL
VSLGVAIHLCCRRRRARLRFMKQLRLHPLEKCSRMDY

SEQ ID NO: 54
MRPRLWLLLAAQLTVLHGNSVLQQTPAYIKVQTNKMVMLSCEAKISLSNMRIYWLRQRQ
APSSDSHHEFLALWDSAKGTIHGEEVEQEKIAVFRDASRFILNLTSVKPEDSGIYFCMIVGSP
ELTFGKGTQLSVVDFLPTTAQPTKKSTLKKRVCRLPRPETQKGPLCSPITLGLLVAGVLVLL
VSLGVAIHLCCRRRRARLRFMKQFYK

SEQ ID NO: 55
MKWKALFTAAILQAQLPITEAQSFGLLDPKLCYLLDGILFIYGVILTALFLRVKFSRSADAPA
YQQGQNQLYNELNLGRREEYDVLDKRRGRDPEMGGKPRRKNPQEGLYNELQKDKMAEA
YSEIGMKGERRRGKGHDGLYQGLSTATKDTYDALHMQALPPR

SEQ ID NO: 56
MKWKALFTAAILQAQLPITEAQSFGLLDPKLCYLLDGILFIYGVILTALFLRVKFSRSADAPA
YQQGQNQLYNELNLGRREEYDVLDKRRGRDPEMGGKPQRRKNPQEGLYNELQKDKMAE
AYSEIGMKGERRRGKGHDGLYQGLSTATKDTYDALHMQALPPR

SEQ ID NO: 57
MLRLLLALNLFPSIQVTGNKILVKQSPMLVAYDNAVNLSWKHLCPSPLFPGPSKPFWVLVV
VGGVLACYSLLVTVAFIIFWVRSKRSRLLHSDYMNMTPRRPGPTRKHYQPYAPPRDFAAYR
S

SEQ ID NO: 58
MLRLLLALNLFPSIQVTGKHLCPSPLFPGPSKPFWVLVVVGGVLACYSLLVTVAFIIFWVRS
KRSRLLHSDYMNMTPRRPGPTRKHYQPYAPPRDFAAYRS

SEQ ID NO: 59
MLRLLLALNLFPSIQVTGNKILVKQSPMLVAYDNAVNLSCKYSYNLFSREFRASLHKGLDS
AVEVCVVYGNYSQQLQVYSKTGFNCDGKLGNESVTFYLQNLYVNQTDIYFCKIEVMYPPP
YLDNEKSNGTIIHVKGKHLCPSPLFPGPSKPFWVLVVVGGVLACYSLLVTVAFIIFWVRSKR
SRLLHSDYMNMTPRRPGPTRKHYQPYAPPRDFAAYRS

SEQ ID NO: 60
MCVGARRLGRGPCAALLLLGLGLSTVTGLHCVGDTYPSNDRCCHECRPGNGMVSRCSRSQ
NTVCRPCGPGFYNDVVSSKPCKPCTWCNLRSGSERKQLCTATQDTVCRCRAGTQPLDSYK
PGVDCAPCPPGHFSPGDNQACKPWTNCTLAGKHTLQPASNSSDAICEDRDPPATQPQETQG
PPARPITVQPTEAWPRTSQGPSTRPVEVPGGRAVAAILGLGLVLGLLGPLAILLALYLLRRD
QRLPPDAHKPPGGGSFRTPIQEEQADAHSTLAKI

INFORMAL PARTIAL SEQUENCE LISTING

SEQ ID NO: 61
MACLGFQRHKAQLNLATRTWPCTLLFFLLFIPVFCKAMHVAQPAVVLASSRGIASFVCEYA
SPGKATEVRVTVLRQADSQVTEVCAATYMMGNELTFLDDSICTGTSSGNQVNLTIQGLRA
MDTGLYICKVELMYPPPYYLGIGNGTQIYVIAKEKKPSYNRGLCENAPNRARM

SEQ ID NO: 62
MACLGFQRHKAQLNLATRTWPCTLLFFLLFIPVFCKAMHVAQPAVVLASSRGIASFVCEYA
SPGKATEVRVTVLRQADSQVTEVCAATYMMGNELTFLDDSICTGTSSGNQVNLTIQGLRA
MDTGLYICKVELMYPPPYYLGIGNGTQIYVIDPEPCPDSDFLLWILAAVSSGLFFYSFLLTAV
SLSKMLKKRSPLTTGVYVKMPPTEPECEKQFQPYFIPIN

SEQ ID NO: 63
MQIPQAPWPVVWAVLQLGWRPGWFLDSPDRPWNPPTFSPALLVVTEGDNATFTCSFSNTS
ESFVLNWYRMSPSNQTDKLAAFPEDRSQPGQDCRFRVTQLPNGRDFHMSVVRARRNDSGT
YLCGAISLAPKAQIKESLRAELRVTERRAEVPTAHPSPSPRPAGQFQTLVVGVVGGLLGSLV
LLVWVLAVICSRAARGTIGARRTGQPLKEDPSAVPVFSVDYGELDFQWREKTPEPPVPCVP
EQTEYATIVFPSGMGTSSPARRGSADGPRSAQPLRPEDGHCSWPL

SEQ ID NO: 64
MAQHGAMGAFRALCGLALLCALSLGQRPTGGPGCGPGRLLLGTGTDARCCRVHTTRCCR
DYPGEECCSEWDCMCVQPEFHCGDPCCTTCRHHPCPPGQGVQSQGKFSFGFQCIDCASGTF
SGGHEGHCKPWTDCTQFGFLTVFPGNKTHNAVCVPGSPPAEPLGWLTVVLLAVAACVLLL
TSAQLGLHIWQLRSQCMWPRETQLLLEVPPSTEDARSCQFPEEERGERSAEEKGRLGDLWV

SEQ ID NO: 65
MAQHGAMGAFRALCGLALLCALSLGQRPTGGPGCGPGRLLLGTGTDARCCRVHTTRCCR
DYPGEECCSEWDCMCVQPEFHCGDPCCTTCRHHPCPPGQGVQSQGKFSFGFQCIDCASGTF
SGGHEGHCKPWTDCCWRCRRRPKTPEAASSPRKSGASDRQRRRGGWETCGCEPGRPPGPP
TAASPSPGAPQAAGALRSALGRALLPWQQKWVQEGGSDQRPGPCSSAAAAGPCRRERETQ
SWPPSSLAGPDGVGS

SEQ ID NO: 66
MAQHGAMGAFRALCGLALLCALSLGQRPTGGPGCGPGRLLLGTGTDARCCRVHTTRCCR
DYPGEECCSEWDCMCVQPEFHCGDPCCTTCRHHPCPPGQGVQSQGKFSFGFQCIDCASGTF
SGGHEGHCKPWTDCTQFGFLTVFPGNKTHNAVCVPGSPPAEPLGWLTVVLLAVAACVLLL
TSAQLGLHIWQLRKTQLLLEVPPSTEDARSCQFPEEERGERSAEEKGRLGDLWV

SEQ ID NO: 67 (GITR co-stimulatory domain AA)
QLGLHIWQLRSQCMWPRETQLLLEVPPSTEDARSCQFPEEERGERSAEEKGR
LGDLWV SEQ ID NO: 68 (VH AA)
EVQLVESGGGLVKPGGSLKLSCAASGFKFSRYAMSWVRQTPEKRLEWVATISSGGSYI
YYPDSVKGRFTISRDNVKNTLYLQMSSLRSEDTAMYYCARRDYDLDYFDSWGQGTTL
TVSS SEQ ID NO: 69 (VL AA)
DIKMTQSPSSMYASLGERVTITCKASRDIRSYLTWYQQKPWKSPKTLIYYATSLADGVPSRF
SGSGSGQDYSLTISSLESDDTATYYCLQHGESPFTFGSGTKLEIKRA

What is claimed is:

1. A nucleic acid molecule comprising a nucleotide sequence encoding a chimeric antigen receptor (CAR) comprising:
   a single chain variable fragment targeted to CD6 comprising an amino acid sequence selected from the group consisting of SEQ ID NO: 38, 39, 40 and 41;
   a spacer comprising the amino acid sequence of SEQ ID NO: 91;
   a transmembrane domain selected from the group consisting of a CD4 transmembrane domain comprising the amino acid sequence of SEQ ID NO: 23, a CD8 transmembrane domain comprising the amino acid sequence of SEQ ID NO: 25; and a CD28 transmembrane domain comprising the amino acid sequence of SEQ ID NO: 7 or SEQ ID NO: 8;
   a CTLA4 co-stimulatory domain comprising the amino acid sequence of SEQ ID NO: 17; and
   a CD3 zeta signaling domain comprising the amino acid sequence of SEQ ID NO: 92.

2. The nucleic acid of claim 1, wherein the CAR comprises or consists of the amino acid sequence of any of SEQ ID Nos: 83-86.

3. A population of T cells comprising the nucleic acid molecule of claim 2.

4. The population of T cells of claim 3, wherein the T cells are regulatory T cells.

5. The population of T cells of claim 4, wherein at least 70%, 80% or 90% of the cells are CD4+/CD25high/CD127low/−.

6. The population of T cells of claim 4 or 5, wherein at least 70%, 80% or 90% of cells are the CD6low/−.

7. A vector comprising the nucleic acid of claim 1.

8. The vector of claim 7, wherein the vector is a viral vector.

9. A population of T cells comprising the nucleic acid molecule of claim 1.

10. The population of T cells of claim 9, wherein the T cells are regulatory T cells.

11. The population of T cells of claim 10, wherein at least 70%, 80% or 90% of the cells are CD4+/CD25high/CD127low/−.

12. The population of T cells of claim 10 or 11, wherein at least 70%, 80% or 90% of cells are the CD6low/−.

13. The nucleic acid of claim 1, wherein the transmembrane domain comprises SEQ ID NO:23.

14. The nucleic acid of claim 1, wherein the transmembrane domain comprises SEQ ID NO:25.

15. The nucleic acid of claim 1, wherein the transmembrane domain comprises SEQ ID NO:7.

16. The nucleic acid of claim 1, wherein the transmembrane domain comprises SEQ ID NO:8.

17. The nucleic acid of claim 1, wherein the CAR comprises:
   a single chain variable fragment targeted to CD6 consisting of an amino acid sequence selected from the group consisting of SEQ ID NO: 38, 39, 40 and 41;
   a spacer consisting of the amino acid sequence of SEQ ID NO: 91;

a transmembrane domain consisting of the amino acid sequence of SEQ ID NO: 23;
a CTLA4 co-stimulatory domain consisting of the amino acid sequence of SEQ ID NO: 17; and
a CD3 zeta signaling domain consisting of the amino acid sequence of SEQ ID NO: SEQ ID NO: 92.

18. The nucleic acid of claim 1, wherein the CAR comprises:
a single chain variable fragment targeted to CD6 consisting of an amino acid sequence selected from the group consisting of SEQ ID NO: 38, 39, 40 and 41;
a spacer consisting of the amino acid sequence of SEQ ID NO: SEQ ID NO: 91;
a transmembrane domain consisting of the amino acid sequence of SEQ ID NO: 25;
a CTLA4 co-stimulatory domain consisting of the amino acid sequence of SEQ ID NO: 17; and
a CD3 zeta signaling domain consisting of the amino acid sequence of SEQ ID NO: 92.

19. The nucleic acid of claim 1, wherein the CAR comprises:
a single chain variable fragment targeted to CD6 consisting of an amino acid sequence selected from the group consisting of SEQ ID NO: 38, 39, 40 and 41;
a spacer consisting of the amino acid sequence of SEQ ID NO: 91;
a transmembrane domain consisting of the amino acid sequence of SEQ ID NO: 7;
a CTLA4 co-stimulatory domain consisting of the amino acid sequence of SEQ ID NO: 17; and
a CD3 zeta signaling domain consisting of the amino acid sequence of SEQ ID NO: 92.

20. The nucleic acid of claim 1, wherein the CAR comprises:
a single chain variable fragment targeted to CD6 consisting of an amino acid sequence selected from the group consisting of SEQ ID NO: 38, 39, 40 and 41;
a spacer consisting of the amino acid sequence of SEQ ID NO: 91;
a transmembrane domain consisting of the amino acid sequence of SEQ ID NO: 8;
a CTLA4 co-stimulatory domain consisting of the amino acid sequence of SEQ ID NO: 17; and
a CD3 zeta signaling domain consisting of the amino acid sequence of SEQ ID NO: 92.

21. A chimeric antigen receptor (CAR) comprising:
a single chain variable fragment targeted to CD6 comprising an amino acid sequence selected from the group consisting of SEQ ID NO: 38, 39, 40 and 41;
a spacer comprising the amino acid sequence of SEQ ID NO: 91;
a transmembrane domain selected from the group consisting of CD4 transmembrane domain comprising the amino acid sequence of SEQ ID NO: 23, a CD8 transmembrane domain comprising the amino acid sequence of SEQ ID NO: 25, and a CD28 transmembrane domain comprising the amino acid sequence of SEQ ID NO: 7 or SEQ ID NO: 8;
a CTLA4 co-stimulatory domain comprising the amino acid sequence of SEQ ID NO: 17; and
a CD3 zeta signaling domain comprising the amino acid sequence of SEQ ID NO: 92.

22. The CAR of claim 21 comprising the amino acid sequence of any one of SEQ ID NOs: 83-86.

23. The CAR of claim 21 consisting of the amino acid sequence of any one of SEQ ID NOs: 83-86.

24. The CAR of claim 21, wherein the transmembrane domain comprises SEQ ID NO:23.

25. The CAR of claim 21, wherein the transmembrane domain comprises SEQ ID NO:25.

26. The CAR of claim 21, wherein the transmembrane domain comprises SEQ ID NO:7.

27. The CAR of claim 21, wherein the transmembrane domain comprises SEQ ID NO:8.

28. The CAR of claim 21, wherein the CAR comprises:
a single chain variable fragment targeted to CD6 consisting of an amino acid sequence selected from the group consisting of SEQ ID NO: 38, 39, 40 and 41;
a spacer consisting of the amino acid sequence of SEQ ID NO: 91;
a transmembrane domain consisting of the amino acid sequence of SEQ ID NO: 23;
a CTLA4 co-stimulatory domain consisting of the amino acid sequence of SEQ ID NO: 17; and
a CD3 zeta signaling domain consisting of the amino acid sequence of SEQ ID NO: 92.

29. The CAR of claim 21, wherein the CAR comprises:
a single chain variable fragment targeted to CD6 consisting of an amino acid sequence selected from the group consisting of SEQ ID NO: 38, 39, 40 and 41;
a spacer consisting of the amino acid sequence of SEQ ID NO: 91;
a transmembrane domain consisting the amino acid sequence of SEQ ID NO: 25;
a CTLA4 co-stimulatory domain consisting of the amino acid sequence of SEQ ID NO: 17; and
a CD3 zeta signaling domain consisting of the amino acid sequence of SEQ ID NO: 92.

30. The CAR of claim 21, wherein the CAR comprises:
a single chain variable fragment targeted to CD6 consisting of an amino acid sequence selected from the group consisting of SEQ ID NO: 38, 39, 40 and 41;
a spacer consisting of the amino acid sequence of SEQ ID NO: 91;
a transmembrane domain consisting of the amino acid sequence of SEQ ID NO: 7;
a CTLA4 co-stimulatory domain consisting of the amino acid sequence of SEQ ID NO: 17; and
a CD3 zeta signaling domain consisting of the amino acid sequence of SEQ ID NO: 92.

31. The CAR of claim 21, wherein the CAR comprises:
a single chain variable fragment targeted to CD6 consisting of an amino acid sequence selected from the group consisting of SEQ ID NO: 38, 39, 40 and 41;
a spacer consisting of the amino acid sequence of SEQ ID NO: 91;
a transmembrane domain consisting of the amino acid sequence of SEQ ID NO: 8;
a CTLA4 co-stimulatory domain consisting of the amino acid sequence of SEQ ID NO: 17; and
a CD3 zeta signaling domain consisting of the amino acid sequence of SEQ ID NO: 92.

32. A population of T cells expressing the CAR of claim 21.

33. The population of T cells of claim 32, wherein the T cells are regulatory T cells.

34. The population of T cells of claim 33, wherein at least 70%, 80% or 90% of the cells are CD4+/CD25high/CD127low/−.

35. The population of T cells of claim 33 or 34, wherein at least 70%, 80% or 90% of cells are the CD6low/−.

* * * * *